US007544678B2

(12) United States Patent
Marks et al.

(10) Patent No.: US 7,544,678 B2
(45) Date of Patent: Jun. 9, 2009

(54) ANTI-ARRYTHMIC AND HEART FAILURE DRUGS THAT TARGET THE LEAK IN THE RYANODINE RECEPTOR (RYR2)

(75) Inventors: Andrew Robert Marks, Larchmont, NY (US); Donald W. Landry, New York, NY (US); Shixian Deng, White Plains, NY (US); Zhen Zhuang Cheng, Elmhurst, NY (US)

(73) Assignee: The Trustees of Columbia University In the City of New York, New York, NY (US)

( * ) Notice: Subject to any disclaimer, the term of this patent is extended or adjusted under 35 U.S.C. 154(b) by 499 days.

(21) Appl. No.: 11/088,058

(22) Filed: Mar. 23, 2005

(65) Prior Publication Data

US 2005/0187386 A1    Aug. 25, 2005

Related U.S. Application Data

(63) Continuation of application No. 10/763,498, filed on Jan. 22, 2004, now abandoned.

(51) Int. Cl.
  *A61P 9/00*     (2006.01)
  *A61K 31/553*   (2006.01)
  *A61K 31/554*   (2006.01)
  *A61K 31/675*   (2006.01)
  *C07F 9/553*    (2006.01)
  *C07D 281/02*   (2006.01)

(52) U.S. Cl. .................................. 514/211.09; 540/552
(58) Field of Classification Search ............ 514/211.09; 540/552
See application file for complete search history.

(56) References Cited

U.S. PATENT DOCUMENTS

| 3,367,930 A | 2/1968 | Schmutz et al. |
| 3,519,647 A | 7/1970 | Krapcho |
| 4,567,254 A | 1/1986 | Kataoka et al. |
| 4,658,055 A | 4/1987 | Onuki et al. |
| 4,723,012 A | 2/1988 | Matsumoto et al. |
| 4,841,055 A | 6/1989 | Matsumoto et al. |
| 4,845,065 A | 7/1989 | Sugimori et al. |
| 4,849,535 A | 7/1989 | Naora et al. |
| 4,888,418 A | 12/1989 | Kawai et al. |
| 4,963,671 A | 10/1990 | Krapcho |
| 4,990,707 A | 2/1991 | Mais et al. |
| 5,064,810 A | 11/1991 | Askanazi et al. |
| 5,075,293 A | 12/1991 | Reifschneider et al. |
| 5,142,647 A | 8/1992 | Nakagawa et al. |
| 5,153,184 A | 10/1992 | Reifschneider et al. |
| 5,166,347 A | 11/1992 | Izawa et al. |
| 5,179,125 A | 1/1993 | Mimura et al. |
| 5,180,720 A | 1/1993 | Husa et al. |
| 5,182,272 A | 1/1993 | Hallinan et al. |
| 5,204,462 A | 4/1993 | Kobayashi et al. |
| 5,210,266 A | 5/1993 | Mimura et al. |
| 5,214,056 A | 5/1993 | Haruta et al. |
| 5,221,681 A | 6/1993 | Kabbe et al. |
| 5,223,508 A | 6/1993 | Izawa et al. |
| 5,260,286 A | 11/1993 | Lawson et al. |
| 5,272,164 A | 12/1993 | Izawa et al. |
| 5,304,380 A | 4/1994 | Miyajima et al. |
| 5,304,558 A | 4/1994 | Kaneko et al. |
| 5,304,644 A | 4/1994 | Husa et al. |
| 5,324,722 A | 6/1994 | Hagen et al. |
| 5,332,734 A | 7/1994 | Kobayashi et al. |
| 5,354,747 A | 10/1994 | Hansen, Jr. et al. |
| 5,354,758 A | 10/1994 | Lawson et al. |
| 5,387,684 A | 2/1995 | Inoue et al. |
| 5,413,929 A | 5/1995 | Ishizaki et al. |
| 5,416,066 A | 5/1995 | Kaneko et al. |
| 5,449,675 A | 9/1995 | Chandrakumar et al. |
| 5,453,282 A | 9/1995 | Kanauchi et al. |
| 5,457,182 A | 10/1995 | Wiederrecht et al. |

(Continued)

FOREIGN PATENT DOCUMENTS

EP         0467325       1/1992

(Continued)

OTHER PUBLICATIONS

Beuckelmann, D. et al. "Intracellular Calcium Handling in Isolated Ventricular Myocytes from Patients with Terminal Heart Failure." Circulation vol. 85, pp. 1046-1055 (1992).

Brillantes, Anne-Marie B. et al., "Stabilization of Calcium Release Channel (Ryanodine Receptor) Function by FK506-Binding Protein." Cell, vol. 77, pp. 513-523. (May 20, 1994).

Brillantes, et al., "Developmental and tissue-specific regulation of rabbit skeletal and cardiac muscle calcium channels involved in excitation-contraction coupline," Circ. Res., vol. 75, pp. 503-510 (1994).

Brillantes, et al., "Differences in cardiac calcium release channel (ryanodine receptor) expression in myocardium from patients with end-state heart failure caused by ischemic versus dilated cardiomyopathy," Circ. Res., vol. 71, pp. 18-26 (1992).

(Continued)

*Primary Examiner*—Brenda L Coleman
(74) *Attorney, Agent, or Firm*—Wilmer Cutler Pickering Hale and Dorr LLP

(57) ABSTRACT

The present invention provides novel 1,4-benzothiazepine intermediates and derivatives, methods for synthesizing same, and methods for assaying same. The present invention also provides methods for using these novel compounds to limit or prevent a decrease in the level of RyR2-bound FKBP12.6 in a subject; to prevent exercise-induced sudden cardiac death in a subject; and to treat or prevent heart failure, atrial fibrillation, or exercise-induced cardiac arrhythmia in a subject. The present invention further provides methods for identifying an agent that enhances binding of RyR2 and FKBP12.6, and agents identified by these methods. Additionally, the present invention provides methods for identifying agents for use in treating or preventing heart failure, atrial fibrillation, or exercise-induced cardiac arrhythmia, and in preventing exercise-induced sudden cardiac death. Also provided are agents identified by such methods.

5 Claims, 8 Drawing Sheets

U.S. PATENT DOCUMENTS

| | | |
|---|---|---|
| 5,461,047 A | 10/1995 | Hansen |
| 5,476,780 A | 12/1995 | Watanabe et al. |
| 5,478,832 A | 12/1995 | Inoue et al. |
| 5,508,293 A | 4/1996 | Okawara et al. |
| 5,523,410 A | 6/1996 | Kagara et al. |
| 5,580,866 A | 12/1996 | Housley et al. |
| 5,593,988 A | 1/1997 | Tahara et al. |
| 5,624,961 A | 4/1997 | Ban et al. |
| 5,654,001 A | 8/1997 | Kanauchi et al. |
| 5,665,881 A | 9/1997 | Inoue et al. |
| 5,719,155 A | 2/1998 | Cho et al. |
| 5,723,458 A | 3/1998 | Brieaddy et al. |
| 5,750,696 A | 5/1998 | Shibata et al. |
| 5,753,649 A | 5/1998 | Tahara et al. |
| 5,767,247 A | 6/1998 | Kaneko et al. |
| 5,780,441 A | 7/1998 | Higa et al. |
| 5,792,655 A | 8/1998 | Watanabe et al. |
| 5,807,850 A | 9/1998 | Nakamura et al. |
| 5,817,652 A | 10/1998 | Brieaddy et al. |
| 5,824,862 A | 10/1998 | Hiyoshi et al. |
| 5,859,240 A | 1/1999 | Brieaddy |
| 5,866,341 A | 2/1999 | Spinella et al. |
| 5,906,819 A | 5/1999 | Kaibuchi et al. |
| 5,910,494 A | 6/1999 | Brieaddy |
| 6,013,499 A | 1/2000 | Narumiya et al. |
| 6,111,072 A | 8/2000 | Narumiya et al. |
| 6,130,060 A | 10/2000 | Nakamura et al. |
| 6,143,784 A | 11/2000 | Greenhaff et al. |
| 6,184,352 B1 | 2/2001 | Nakamura et al. |
| 6,235,730 B1 | 5/2001 | Sato et al. |
| 6,255,472 B1 | 7/2001 | Tokino et al. |
| 6,271,353 B1 | 8/2001 | Nakamura et al. |
| 6,313,113 B1 | 11/2001 | Lohray et al. |
| 6,316,485 B1 | 11/2001 | Nakamura et al. |
| 6,338,955 B2 | 1/2002 | Oguri et al. |
| 6,348,334 B1 | 2/2002 | Nagata et al. |
| 6,362,231 B1 | 3/2002 | Sakai et al. |
| 6,391,595 B1 | 5/2002 | Kato et al. |
| 6,403,830 B2 | 6/2002 | Webber et al. |
| 6,410,561 B1 | 6/2002 | Shinkai et al. |
| 6,426,365 B1 | 7/2002 | Shinkai et al. |
| 6,465,518 B2 | 10/2002 | Hansen, Jr. et al. |
| 6,465,686 B2 | 10/2002 | Grapperhaus et al. |
| 6,489,125 B1 | 12/2002 | Marks et al. |
| 6,495,544 B2 | 12/2002 | Hansen, Jr. et al. |
| 6,500,816 B1 | 12/2002 | Ekimoto et al. |
| 6,506,745 B1 | 1/2003 | Aisaka et al. |
| 6,545,170 B2 | 4/2003 | Pitzele et al. |
| 6,562,618 B1 | 5/2003 | Tamatani et al. |
| 6,562,828 B1 | 5/2003 | Katoh et al. |
| 6,583,157 B2 | 6/2003 | McGee et al. |
| 6,586,474 B2 | 7/2003 | Webber et al. |
| 6,632,976 B1 | 10/2003 | Tomizuka et al. |
| 6,649,366 B2 | 11/2003 | Chubinskaya et al. |
| 6,660,837 B1 | 12/2003 | Kaibuchi et al. |
| 6,673,904 B2 | 1/2004 | Nishikawa et al. |
| 6,683,083 B1 | 1/2004 | Kaneko et al. |
| 6,750,255 B2 | 6/2004 | Sakai et al. |
| 6,753,346 B2 | 6/2004 | Shinkai et al. |
| 6,756,406 B2 | 6/2004 | Durley et al. |
| 6,780,608 B1 | 8/2004 | Hakamata et al. |
| 6,787,668 B2 | 9/2004 | Pitzele et al. |
| 6,803,039 B2 | 10/2004 | Tsuji et al. |
| 6,808,873 B2 | 10/2004 | Murphy et al. |
| 6,812,252 B2 | 11/2004 | Ikawa et al. |
| 6,821,987 B2 | 11/2004 | Kubo et al. |
| 6,824,973 B2 | 11/2004 | Tang et al. |
| 6,828,456 B2 | 12/2004 | Hansen, Jr. et al. |
| 6,830,896 B2 | 12/2004 | Kaneko et al. |
| 6,852,753 B2 | 2/2005 | Koeller et al. |
| 6,869,975 B2 | 3/2005 | Abe et al. |
| 6,890,531 B1 | 5/2005 | Horie et al. |
| 6,897,295 B1 | 5/2005 | Nagata et al. |
| 6,906,072 B1 | 6/2005 | Yamamoto et al. |
| 6,914,158 B2 | 7/2005 | Webber et al. |
| 6,939,895 B2 | 9/2005 | Sakai et al. |
| 6,951,889 B2 | 10/2005 | Hansen, Jr. et al. |
| 6,962,926 B2 | 11/2005 | Laborde et al. |
| 6,964,975 B2 | 11/2005 | Ueno et al. |
| 6,977,252 B1 | 12/2005 | Kaneko et al. |
| 6,989,275 B2 | 1/2006 | Waggoner |
| 6,998,469 B2 | 2/2006 | Tandon et al. |
| 7,005,450 B2 | 2/2006 | Durley et al. |
| 7,029,671 B1 | 4/2006 | Koezuka et al. |
| 7,030,225 B1 | 4/2006 | Tamatani et al. |
| 7,041,870 B2 | 5/2006 | Tomizuka et al. |
| 7,045,615 B2 | 5/2006 | Tamatani et al. |
| 7,064,194 B2 | 6/2006 | Misawa et al. |
| 7,102,013 B2 | 9/2006 | Webber et al. |
| 7,112,655 B1 | 9/2006 | Tamatani et al. |
| 7,135,466 B2 | 11/2006 | Sakai et al. |
| 7,163,952 B2 | 1/2007 | Inaba et al. |
| 7,312,044 B2 | 12/2007 | Marks |
| 7,393,652 B2 | 7/2008 | Marks |
| 2002/0042405 A1 | 4/2002 | Schuh |
| 2002/0052358 A1 | 5/2002 | Chubinskaya et al. |
| 2002/0107406 A1 | 8/2002 | Sakai et al. |
| 2002/0115831 A1 | 8/2002 | Tamatani et al. |
| 2002/0132001 A1 | 9/2002 | Garthwaite et al. |
| 2002/0151685 A1 | 10/2002 | Tamatani et al. |
| 2002/0156242 A1 | 10/2002 | Tamatani et al. |
| 2002/0199213 A1 | 12/2002 | Tomizuka et al. |
| 2003/0022911 A1 | 1/2003 | Smith et al. |
| 2003/0044845 A1 | 3/2003 | Jenkins et al. |
| 2003/0054531 A1 | 3/2003 | Gretarsdottir et al. |
| 2003/0055027 A1 | 3/2003 | Schun |
| 2003/0055087 A1 | 3/2003 | Shinkai et al. |
| 2003/0064406 A1 | 4/2003 | Kaneko et al. |
| 2003/0083472 A1 | 5/2003 | Tamatani et al. |
| 2003/0087907 A1 | 5/2003 | Kubo et al. |
| 2003/0092708 A1 | 5/2003 | Shinkai et al. |
| 2003/0124637 A1 | 7/2003 | Kaneko et al. |
| 2003/0134331 A1 | 7/2003 | Marks et al. |
| 2003/0144526 A1 | 7/2003 | Sakai et al. |
| 2003/0176485 A1 | 9/2003 | Sakai et al. |
| 2003/0181764 A1 | 9/2003 | Ikawa et al. |
| 2003/0186885 A1 | 10/2003 | Tandon et al. |
| 2003/0191323 A1 | 10/2003 | Ikawa et al. |
| 2003/0195218 A1 | 10/2003 | Koeller et al. |
| 2003/0199482 A1 | 10/2003 | Seibert et al. |
| 2003/0199701 A1 | 10/2003 | Webber et al. |
| 2003/0220310 A1 | 11/2003 | Schuh |
| 2003/0220312 A1 | 11/2003 | Schuh |
| 2003/0232855 A1 | 12/2003 | Iwamura et al. |
| 2004/0006099 A1 | 1/2004 | Katoh et al. |
| 2004/0017409 A1 | 1/2004 | Mizutani et al. |
| 2004/0048780 A1 | 3/2004 | Marks |
| 2004/0053919 A1 | 3/2004 | Chubinskaya et al. |
| 2004/0073012 A1 | 4/2004 | Tamatani et al. |
| 2004/0073957 A1 | 4/2004 | Tomizuka et al. |
| 2004/0082653 A1 | 4/2004 | Nonaka et al. |
| 2004/0120945 A1 | 6/2004 | Tamatani et al. |
| 2004/0132658 A1 | 7/2004 | Tamatani et al. |
| 2004/0132727 A1 | 7/2004 | Sakai et al. |
| 2004/0146506 A1 | 7/2004 | Tamatani et al. |
| 2004/0146991 A1 | 7/2004 | Tsuji et al. |
| 2004/0151669 A1 | 8/2004 | Tamatani et al. |
| 2004/0151718 A1 | 8/2004 | Tamatani et al. |
| 2004/0151720 A1 | 8/2004 | Tamatani et al. |
| 2004/0171613 A1 | 9/2004 | Iwamura et al. |
| 2004/0173802 A1 | 9/2004 | Yukimoto |
| 2004/0175814 A1 | 9/2004 | Kato et al. |
| 2004/0180052 A1 | 9/2004 | Tsuji et al. |
| 2004/0186178 A1 | 9/2004 | Webber et al. |

| | | |
|---|---|---|
| 2004/0192584 A1 | 9/2004 | McMahon et al. |
| 2004/0198719 A1 | 10/2004 | Laborde et al. |
| 2004/0209871 A1 | 10/2004 | Fox et al. |
| 2004/0220193 A1 | 11/2004 | Yamamoto et al. |
| 2004/0224368 A1 | 11/2004 | Marks |
| 2004/0225018 A1 | 11/2004 | Sunami et al. |
| 2004/0229781 A1 | 11/2004 | Marks et al. |
| 2004/0229788 A1 | 11/2004 | Tamatani et al. |
| 2004/0229790 A1 | 11/2004 | Tezuka et al. |
| 2004/0229803 A1 | 11/2004 | Stephenson et al. |
| 2004/0229876 A1 | 11/2004 | Kubo et al. |
| 2004/0229957 A1 | 11/2004 | Shinkai et al. |
| 2004/0235162 A1 | 11/2004 | Sato |
| 2004/0242683 A1 | 12/2004 | Urata et al. |
| 2005/0009733 A1 | 1/2005 | Stephenson et al. |
| 2005/0020668 A1 | 1/2005 | Urata et al. |
| 2005/0032210 A1 | 2/2005 | Sato et al. |
| 2005/0035939 A1 | 2/2005 | Akiyama |
| 2005/0051181 A1 | 3/2005 | Okamoto |
| 2005/0059655 A1 | 3/2005 | Garvey et al. |
| 2005/0059810 A1 | 3/2005 | Maeda et al. |
| 2005/0070543 A1 | 3/2005 | Stephenson |
| 2005/0070545 A1 | 3/2005 | Fox et al. |
| 2005/0074762 A1 | 4/2005 | Nakamura et al. |
| 2005/0113451 A1 | 5/2005 | Hansen et al. |
| 2005/0159365 A1 | 7/2005 | Serizawa et al. |
| 2005/0159403 A1 | 7/2005 | Stephenson et al. |
| 2005/0165106 A1 | 7/2005 | Webber et al. |
| 2005/0171196 A1 | 8/2005 | Fujii et al. |
| 2005/0177884 A1 | 8/2005 | Tomizuka et al. |
| 2005/0186640 A1 | 8/2005 | Marks et al. |
| 2005/0187221 A1 | 8/2005 | Matsuda et al. |
| 2005/0187386 A1 | 8/2005 | Marks et al. |
| 2005/0192259 A1 | 9/2005 | Garthwaite et al. |
| 2005/0213426 A1 | 9/2005 | Midas et al. |
| 2005/0215540 A1 | 9/2005 | Marks et al. |
| 2005/0255546 A1 | 11/2005 | Nishikawa |
| 2005/0256199 A1 | 11/2005 | Durley et al. |
| 2005/0277649 A1 | 12/2005 | DeGraffenreid et al. |
| 2006/0011375 A1 | 1/2006 | Sugimoto et al. |
| 2006/0014768 A1 | 1/2006 | Kawasaki et al. |
| 2006/0026698 A1 | 2/2006 | Tomizuka et al. |
| 2006/0030565 A1 | 2/2006 | Shinkai et al. |
| 2006/0035882 A1 | 2/2006 | Koga et al. |
| 2006/0037093 A1 | 2/2006 | Tomizuka et al. |
| 2006/0041945 A1 | 2/2006 | Robl et al. |
| 2006/0059575 A1 | 3/2006 | Kusunoki et al. |
| 2006/0078992 A1 | 4/2006 | Misawa et al. |
| 2006/0084658 A1 | 4/2006 | Yamamoto et al. |
| 2006/0100195 A1 | 5/2006 | Maruyama et al. |
| 2006/0122181 A1 | 6/2006 | Ikemoto et al. |
| 2006/0123490 A1 | 6/2006 | Kakitani et al. |
| 2006/0135506 A1 | 6/2006 | Stephenson et al. |
| 2006/0167043 A1 | 7/2006 | Iwakubo et al. |
| 2006/0185025 A1 | 8/2006 | Oshimura et al. |
| 2006/0189603 A1 | 8/2006 | Garvey et al. |
| 2006/0194767 A1 | 8/2006 | Marks et al. |
| 2006/0205731 A1 | 9/2006 | Kodama et al. |
| 2006/0211717 A1 | 9/2006 | Sakai et al. |
| 2006/0217426 A1 | 9/2006 | Eto et al. |
| 2006/0223133 A1 | 10/2006 | Tamatani et al. |
| 2006/0233902 A1 | 10/2006 | Yajima et al. |
| 2006/0258701 A1 | 11/2006 | Mitsuya et al. |
| 2006/0270705 A1 | 11/2006 | Yonemori et al. |
| 2006/0293266 A1 | 12/2006 | Marks |
| 2007/0010571 A1 | 1/2007 | Garvey et al. |
| 2007/0010670 A1 | 1/2007 | Hirata et al. |
| 2007/0049572 A1 | 3/2007 | Marks et al. |

FOREIGN PATENT DOCUMENTS

| | | |
|---|---|---|
| EP | 1147772 | 10/2001 |
| EP | 1369129 | 12/2003 |
| EP | 1439221 A1 | 7/2004 |
| EP | 1447096 | 8/2004 |
| EP | 1743895 | 1/2007 |
| FR | 2709753 | 3/1995 |
| JP | 3093419 | 4/1991 |
| JP | 4230681 | 8/1992 |
| JP | 05/271208 | 10/1993 |
| JP | 10045706 | 2/1998 |
| JP | 11199574 | 7/1999 |
| WO | WO-92/12148 | 7/1992 |
| WO | WO-92/19617 | 11/1992 |
| WO | WO-93/13082 | 11/1992 |
| WO | WO-94/11360 | 5/1994 |
| WO | WO-94/29286 | 12/1994 |
| WO | WO-96/08228 | 3/1996 |
| WO | WO-97/03986 | 2/1997 |
| WO | WO-97/17344 | 5/1997 |
| WO | WO-98/05657 | 2/1998 |
| WO | WO-98/45291 | 10/1998 |
| WO | WO-99/16758 | 4/1999 |
| WO | WO-99/26921 | 6/1999 |
| WO | WO-99/32115 | 7/1999 |
| WO | WO-01/00185 | 1/2001 |
| WO | WO-01/47510 | 7/2001 |
| WO | WO-02/08211 A1 | 1/2002 |
| WO | WO-02/14245 | 2/2002 |
| WO | WO-02/14246 | 2/2002 |
| WO | WO-02/051232 | 7/2002 |
| WO | WO-02/051838 | 7/2002 |
| WO | WO-02/053548 | 7/2002 |
| WO | WO-02056790 | 7/2002 |
| WO | WO-02/072145 | 9/2002 |
| WO | WO-03/034980 | 5/2003 |
| WO | WO-03/043655 | 5/2003 |
| WO | WO-2004/022057 | 3/2004 |
| WO | WO-2004/023030 | 3/2004 |
| WO | WO-2004/042389 A2 | 5/2004 |
| WO | WO-2004/080283 | 9/2004 |
| WO | WO-2005/002518 | 1/2005 |
| WO | WO-2005/037195 | 4/2005 |
| WO | WO-2005/094457 | 10/2005 |
| WO | WO-2005/105793 | 11/2005 |
| WO | WO-2006/071603 | 7/2006 |
| WO | WO-2006/101496 | 9/2006 |
| WO | WO-2006/101497 | 9/2006 |
| WO | WO-2007/024717 | 3/2007 |

OTHER PUBLICATIONS

Bristow, Michael R. et al. "Beta-Adrenergic Neuroeffector Abnormalities in the Failing Human Heart are Produced by Local Rather Than Systemic Mechanisms." J. Clin. Invest., vol. 89, pp. 803-815 (Mar. 1992).

Bristow, Michael R., M.D., Ph.D. et al., "Decreased Catecholamine Sensitivity and B-Adrenergic-Receptor Density in Failing Human Hearts." The New England Journal of Medicine, vol. 307, No. 4, pp. 205-211 (Jul. 22, 1982).

Cameron, Andrew M. et al. "FKBP12 Binds the Inositol 1,4,5-Trisphosphate Receptor at Leucine-Proline (1400-1401) and Anchors Calcineurin to this FK506-like Domain." Journal of Biological Chemistry, vol. 272, No. 44, pp. 27582-27588, (Oct. 31, 1997).

Catsoulacos, "Synthesis of Substituted Dihydrobenzothiazepines and Related Compounds." J Heterocyclic Chemistry, vol. 7, No. 2: pp. 409-411. (1970).

Chatrath, et al., "Beta-blocker therapy failures in symptomatic probands with genotyped long-QT syndrome," Pediatr. Cardiol., vol. 25, pp. 459-465 (2004).

Che, et al., "Reversal of P-glycoprotein mediated multidrug resistance by a newly synthesized 1,4-benzothiazipine derivative, JTV-519," Cancer Lett., vol. 187, pp. 111-119 (2002).

Chen, Ye-Guang et al., "Mechanism of TGFbeta Receptor Inhibition by FKBP12." The EMBO Journal, vol. 16, No. 13, pp. 3866-3876. (1997).

Chidsey et al. "Augmentation of Plasma Nor-epinephrine Response to Exercise in Patients with Congestive Heart Failure." N. Engl. J. Med. vol. 267, No. 13, pp. 650-654. (1962).

Choi, et al., "Spectrum and frequency of cardiac channel defects in swimming-triggered arrhythmia syndromes," Circulation, vol. 110, pp. 2119-2124 (2004).

Choi, et al., "Sudden cardiac death and channelopathies: a review of implantable defibrillator therapy," Pediatr. Clin. North Am., vol. 51, pp. 1289-1303 (2004).

Chugh et al. "Epidemiology and Natural History of Atrial Fibrillation: Clinical Implications." J. Am. Coll. Cardiol., vol. 37, No. 2, pp. 371-378. (2001).

Culligan, et al., "Drastic reduction of calsequestrin-like proteins and impaired calcium binding in dystrophic mdx muscle," J. Appl. Physiol., vol. 92, pp. 435-445 (2002).

Daoud et al. "Effect of Verapamil and Procainamide on Atrial Fibrillation-Induced Electrical Remodeling in Humans." Circulation, vol. 96, pp. 1542-1550. (1997).

Doi et al., "Propranolol prevents the Development of Heart Failure by Restoring FKBP12.60-Mediated Stabilization of Ryanodine Receptor." Circulation vol. 105, pp. 1374-1379. (2002).

Dorian, P., "Antiarrhythmic action of beta-blockers: potential mechanisms," J. Cardiovasc. Pharmacol. Therapeut., vol. 10, pp. S15-S22 (2005).

Echt et al., "Mortality and morbidity in patients receiving encainide, flecainide, or placebo," The Cardiac Arrhythmia Suppression Trial, N. Engl. J. Med., vol. 324, pp. 781-788. (1991).

Eichhorn et al. "Medical Therapy can Improve the Biological Properties of the Chronically Failing Heart. A New Era in the Treatment of Heart Failure." Circulation, vol. 94, pp. 2285-2296. (1996).

Elvan et al. "Pacing-induced Chronic Atrial Fibrillation Impairs Sinus Node Function in Dogs: Electrophysiological Remodeling." Circulation, vol. 94, pp. 2953-2960. (1996).

Exhibit A: Chemical Structures.

Fabiato, A. "Calcium-induced Release of Calcium from the Cardiac Sarcoplasmic Reticulum." Am. J. Physiol., vol. 245, pp. C1-C14. (1983).

Falk, R.H. "Atrial Fibrillation." N. Engl. J. Med., vol. 344, No. 14, pp. 1067-1078. (2001).

Farr, et al., "Sparking the failing heart," N. Engl: J. Med., vol. 351, pp. 185-187 (2004).

Fitzgerald, et al., "Reduced ryanodine receptor content in isolated neonatal cardiomyocytes compared with the intact tissue," J. Mol. Cell, Cardiol., vol. 26, pp. 1261-1265 (1994).

Fodor et al. "New Convenient Synthesis of 1,4-benzothiazepines." Tetrahedron Letters, vol. 36, No. 5, pp. 753-756. (1995).

Fozzard, H.A. "Afterdepolarizations and triggered activity." Basic Res. Cardiol., vol. 87, pp. 105-113. (1992).

Gaspo et al. "Functional Mechanisms Underlying Tachycardia-induced Sustained Atrial Fibrillation in a Chronic Dog Model." Circulation, vol. 96, pp. 4027-4035. (1997).

Gillian, et al., "Analysis of expression of the human ryanodine receptor gene in malignant hyperthermia skeletal muscle tissue," Biochem. Soc. Trans., vol. 19, pp. 46S (1991).

Gillo et al. "Calcium Influx in Induced Differentiation of Murine Erythroleukemia Cells." Blood, vol. 81, No, 3, pp. 783-792. (1993).

Go, Loewe O. et al., "Differential Regulation of Two Types of Intracellular Calcium Release Channels during End-Stage Heart Failure." J. Clin. Invest., vol. 95, pp. 888-894. (Feb. 1995).

Goette et al. "Electrical Remodeling in Atrial Fibrillation: Time Course and Mechanisms." Circulation, vol. 94, pp. 2968-2974. (1996).

Gomez, A.M. et al. "Defective Excitation-Contraction Coupling in Experimental Cardiac Hypertrophy and Heart Failure." Science, vol. 276, pp. 800-806. (May 2, 1997).

Gwathmey et al. "Abnormal Intracellular Calcium Handling in Myocardium From Patients with End-Stage Heart Failure." Circ. Res., vol. 61, pp. 70-76. (1987).

Hachida et al. "Protective effect of JTV519 on Prolonged Myocardial Preservation." Transplant Proc., vol. 31, pp. 1094. (1999).

Hachida, M. et al. "Protective Effect of JT-519, a new 1, 4-Benzothiazepine Derivative, on Prolonged Myocardial Preservation." J. Card. Surg., vol. 14, pp. 187-193. (1999).

Hain, J. et al., "Phosphorylation Modulates the Function of the Calcium Release Channel of Sarcoplasmic Reticulum from Skeletal Muscle." Biophys. J., vol. 67, pp. 1823-1833. (1994).

Hain, Jurgen et al. "Phosphorylation Modulates the Function of the Calcium Release Channel of Sarcoplasmic Reticulum from Cardiac Muscle." The Journal of Biological Chemistry, vol. 270, No. 5, pp. 2074-2081. (Feb. 3, 1995).

Haut, Donahue, et al., "Annexin V Disruption Impairs Mechanically Induced Calcium Signaling in Osteoblastic Cells," Bone, vol. 35, No. 3) pp. 656-663, (2004).

Ikemoto, et al., "Regulation of calcium release by interdomain interaction within ryanodine receptors," Front Biosci., vol. 7, pp. d671-683 (2002).

Inagaki et al. "Anti-ischemic Effect of a Novel Cardioprotective Agent, JTV 519, is mediated through Specific Activation of d-Isoform of Protein Kinase C in Rat Ventricular Myocardium." Circulation, vol. 101, pp. 797-804. (2000).

Inagaki et al. "The Cardioprotective Effects of a new 1, 4-benzothiazepine Derivative, JTV 519, on ischemia/reperfusion-induced Ca2+ Overload in Isolated Rat Hearts." Cardiovasc Drugs Ther., vol. 14, pp. 489-495. (2000).

Ishii. et al.. "JTV-519.. a new cardioprotective drug, and cariporide, synergistically improved post-ischemic contractile recovery in rat," Journal of Molecular and Cellular Cardiology, vol. 35, Issue 6, p. A29 (2002).

Ito et al. "JTV-519, a Novel Cardioprotective Agent, Improves the Contractile Recovery after Ischaemia Reperfusion in Coronary Perfused Guinea Pig Ventricular Muscles." Br. J. Pharmacol., vol. 130, No. 4, pp. 767-776. (2000).

Jayaraman, T. et al. "Regulation of the Inositol 1,4,5-Trisphosphate Receptor By Tyrosine Phosphorylation." Science, vol. 272, pp. 1492-1494. (1996.).

Jayaraman, Thottala et al. "FK506 Binding Protein Associated with the Calcium Release Channel (Ryanodine Receptor)." The Journal of Biological Chemistry, vol. 267, No. 14, pp. 9474-9477. (May 15, 1992).

Kaftan, Edward et al. "Effects of Rapamycin on Ryanodine Receptor/Ca2+-Release Channels from Cardiac Muscle." Circulation Research, vol. 78, No. 6, pp. 990-997. (Jun. 1996).

Kapiloff, M.S. et al. "mAKAP and the ryanodine receptor are part of a multi-component signaling complex on the cardiomyocyte nuclear envelope," Journal of Cell Science, vol. 114, pp. 3167-3176 (2001).

Kawabata et al. "A Novel Cardioprotective Agent, JTV-519, is abolished by Nitric Oxide Synthase Inhibitor on Myocardial Metabolism in Ischemia-Reperfused Rabbit Hearts." Hypertens Res., vol. 25, pp. 303-309. (2002).

Kawabata et al. "Effect of a Novel Cardioprotective Agent, JTV-519, on Metabolism, Contraction and Relaxation in the Ischemia-Reperfused Rabbit Heart." Jpn Circ. J., vol. 64, pp. 772-776. (2000).

Kimura, J. et al. "Effects of a Novel Cardioprotective Drug, JTV-519 on Membrane Currents of Guinea Pig Ventricular Myocytes." Jpn. J. Pharmacol., vol. 79, pp. 275-281. (1999).

Kirsch, et al., "The roles of annexins and types II and X collagen in matrix vesicle-mediated mineralization of growth plate cartilage," J. Biol. Chem., vol. 275, pp. 35577-35583 (2000).

Kobrinsky, et al., "Expressed ryanodine receptor can substitute for the inositol 1,4,5-trisphosphate receptor in *Xenopus laevis* oocytes during progesterone-induced maturation," Dev. Biol., vol. 172, pp. 531-540 (1995).

Kohno et al., "A New Cardioprotective Agent, JTV-519, Improves Defective Channel Gating of Ryanodine Receptor in Heart Failure." Am. J. Physiol Heart Circ. Physiol., vol. 284, No. 3, pp. H1035-H1042. First published Nov. 14, 2002. (Mar. 2003).

Kumagai et al. "Antiarrhythmic Effects of JTV-519, a novel Cardioprotective Drug, on Atrial Fibrillation/Flutter in a Canine Sterile Pericarditis Model." J. Cardiovasc. Electrophysiol. vol. 14, No. 8, pp. 880-884. (2003).

Laitinen, P.J. et al. "Mutations of the Cardiac Ryanodine Receptor (RyR2) Gene in Familial Polymorphic Ventricular Tachycardia." Circulation, vol. 103, pp. 485-490. (2001).

Lee, et al., "Sudden unexplained death: evaluation of those left behind," The Lancet, vol. 362, pp. 1429-1431 (2003).

Leenhardt, A. et al. "Catecholaminergic Polymorphic Ventricular Tachycardia in Children: a 7-year follow-up of 21 patients." Circulation, vol. 91, pp. 1512-1519. (1995).

Lehnart et al. "Cardiac Ryanodine Receptor Function and Regulation in Heart Disease." Ann NY Acad Sci., vol. 1015, pp. 144-159. (2004).

Lehnart, et al., "Calstabin deficiency, ryanodine receptors, and sudden cardiac death," Biochem. Biophys. Res. Commun., vol. 322, pp. 1267-1279 (2004).

Lehnart, et al., "Immunophilins and coupled gating of ryanodine receptors,"Curr. Top. Med. Chem., vol. 3, pp. 1383-1391 (2003).

Leistad et al. "Atrial Contractile Dysfunction After Short-Term Atrial Fibrillation is Reduced by Verapamil But Increased by BAY K8644." Circulation, vol. 93, pp. 1747-1754. (1996).

Lesh. et al.. "Anti-ryanodine receptor antibody binding sites in vascular and endocardial endothelium," Cir., Res., vol. 72, pp. 481-488 (1993).

Levy et al. "Long-Term Trends in the Incidence of the Survival with Heart Failure." N. Engl. J. Med., vol. 347, No. 18, pp. 1397-1402. (2002).

Manzur, et al., "A severe clinical and pathological variant of central core disease with possible autosomal recessive inheritance," Neur. Disorders, vol. 8, pp. 467-473 (1998).

Marban, E. et al. "Mechanisms of Arrhythmogenic Delayed and Early Afterpolarizations in Ferret Ventricular Muscle." J. Clin. Invest., vol. 78, pp. 1185-1192. (1986).

Marks et al. "Clinical Implications of Cardiac Ryanodine Receptor/Calcium Release Channel Mutation Linked to Sudden Cardiac Death." Circulation, vol. 106, p. 8-10. (Jul. 2, 2002).

Marks et al. "Involvement of the Cardiac Ryanodine Receptor/Calcium Release Channel in Catecholaminergic Polymorphic Ventricular Tachycardia." J. Cell. Physiol., vol. 190, pp. 1-6. First published Oct. 26, 2001 (2002).

Marks et al. "Progression of Heart Failure: Is Protein Kinase a Hyerphosphorylation of the Ryanodine Receptor a Contributing Factor?" Circulation, vol. 105, pp. 272-275 (2002).

Marks et al. "Ryanodine Receptors, FKBP12, and Heart Failure." Frontiers in Bioscience, vol. 7, pp. 970-977. (2002).

Marks et al., "A Guide for the Perplexed: Towards an Understanding of the Molecular Basis of Heart Failure." Circulation. vol. 107, pp. 1456-1459. (2003).

Marks, A.R. "Cardiac Intracellular Calcium Release Channels: Role in Heart Failure." Circ. Res., vol. 87, pp. 8-11. (2000).

Marks, A.R. "Cellular Functions of Immunophilins." Physiol. Rev., vol. 76, No. 3, pp. 631-649. (1996).

Marks, Andrew. "Ryanodine Receptors/Calcium Release Channels in Heart Failure and Sudden Cardiac Death," Journal of Molecular Cell Cardiology, vol. 33, pp. 615-624. (2001).

Marks, AR, "Arrhythmias of the heart: beyond ion channels," Nat. Medicine, vol. 9, pp. 263-264, (2003).

Marks, AR, "Calcium and the heart: a question of life and death," J. Clin. Investigation, vol. 111, pp. 597-600, (2003).

Marks, AR, "Calcium channels expressed in vascular smooth muscle," Circulation, vol. 86, pp. III61-III67 (1992).

Marks, AR, "Immunophilin modulation of calcium channel gating," Methods., vol. 9, pp. 177-187 (1996).

Marks, AR, "Intracellular calcium-release channels: regulators of cell life and death," Am. J. Phsiol., vol. 272, pp. H597-H605 (1997).

Marks, et al., "Molecular cloning and characterization of the Ryanodine receptor/junctional channel complex cDNA from skeletal muscle sarcoplasmic reticulum," Proc. Natl. Acad. Sci. U.S.A., vol. 86, pp. 8683-8687 (1989).

Marks, et al., "Regulation of ryanodine receptors via macromolecular complexes: a novel role for leucine/isoleucine zippers," Tends Cardiovasc. Med., vol. 12, pp. 166-170 (2002).

Marks, et al., "Surface topography analysis of the ryanodine receptor/junctional channel complex based on proteolysis sensitivity mapping," J. Biol. Chem., vol. 265, pp. 13143-13149 (1990).

Marks, et al., "The ryanodine receptor/junctional channel complex is regulated by growth factors in a myogenic cell line," J. Cell. Biol., vol. 114, pp. 303-312, (1991).

Maron, et al., "Recommendations for physical activity and recreational sports participation for young patients with genetic cardiovascular diseases," Circulation, vol. 109, pp. 2807-2816 (2004).

Marx et al. "Requirement of a Macromolecular signaling complex for Beta-Adrenergic Receptor Modulation of the KCNQ1/KCNE1 Potassium Channel," Science, vol. 295, pp. 496-499. (2002).

Marx et al., "Coupled Gating Between Cardiac Calcium Release Channels (Ryanodine Receptors)" Circ. Res., vol. 88, pp. 1151-1158. (2001).

Marx S.O et al., "Regulation of the Ryanodine Receptor in Heart Failure." Basic Res. Cardiol., vol. 97, Suppl. 1, pp. 1/49-1/51. (2002).

Marx, S.O. et al. "Phosphorylation-dependent Regulation of Ryanodine Receptors: A Novel Role for Leucine/Isoleucine Zippers." J. Cell. Biol., vol. 153, No. 4, pp. 699-708. (2001).

Marx, S.O. et al. "PKA Phosphorylation Dissociates FKBP12.6 from the Calcium Release Channel (Ryanodine Receptor): Defective Regulation in Failing Hearts." Cell, vol. 101, pp. 365-376. (2000).

Marx, Steven O. et al. "Coupled Gating Between Individual Skeletal Muscle Ca2+ Release Channel (Ryanodine Receptors)." Science, vol. 281, pp. 818-821. (Aug. 7, 1998).

McPhie, et al., "Structure of the hormone binding domain of human beta 1 thyroid hormone nuclear receptor: is is an alpha/beta barrel?" Biochemistry, vol. 32, pp. 7460-7465 (1993).

Morillo et al. "Chronic Rapid Atrial Pacing: Structural, Functional, and Electrophysiological Characteristics of a New Model of Sustained Atrial Fibrillation." Circulation, vol. 91, pp. 1588-1595. (1995).

Morita, et al., "Ca channel blocking activity of JTV-519, a novel protective drug to cytotoxicity," Neuroscience Research, vol. 31, Supp. 1, p. S65 (1998).

Nabauer, M. et al. "Regulation of Calcium Release is Gated by Calcium Current, Not Gating Charge, in Cardiac Myocytes." Science, vol. 244, pp. 800-803. (1989).

Nakamura, et al., "Reversal of cisplatin resistance by the 1,4-benzothiazepine derivative, JTV-519," Jpn. J. Cancer Res., vol. 92, pp. 597-602 (2001).

Nakaya et al. "Inhibitory Effects of JTV-519, a Novel Cardioprotective Drug, on Potassium Currents and Experimental Atrial Fibrillation in Guinea-Pig Hearts," British Journal of Pharmacology, vol. 131, pp. 1363-1372. (2000).

Ondrias, et al., "FKBP12 modulates gating of the ryanodine receptor/calcium release channel," Ann. N.Y. Acad. Sci., vol. 853, pp. 149-156 (1998).

Ondrias, et al., Single channel properties and calcium conductance of the cloned expressed ryanodine receptor/calcuim-release channel, Soc. Gen. Physiol, Serv., vol. 51, pp. 29-45 (1996).

Ono et al. "Altered Interaction of FKBP12.6 with Ryanodine Receptor as a Case of Abnormal Ca2+ Release in Heart Failure." Cardiovasc. Res., vol. 48, pp. 323-331. (2000).

Paul-Pletzer, et al., "Identification of a dantrolene-binding sequence on the skeletal muscle ryanodine receptor," J. Biol. Chem., vol. 277, pp. 34918-34923 (2002).

Priori, S.G. et al. "Clinical and Molecular Characterization of Patients with Catecholaminergic Polymorphic Ventricular Tachycardia." vol. 106, pp. 69-74. (2002).

Priori, S.G. et al. "Mutations in the Cardiac Ryanodine Receptor Gene (hRyR2) Underlie Catecholaminergic Polymorphic Ventricular Tachycardia." Circulation, vol. 103, pp. 196-200. (2001).

Reiken et al. "PKA Phosphorylation Activates the Calcium Release Channel (Ryanodine Receptor) in Skeletal Muscle: Defective Regulation in Heart Failure." J. Cell. Biol., vol. 160, No. 6, pp. 919-928. (2003).

Reiken et al. "Protein Kinase A Phosphorylation of the Cardiac Calcium Release Channel (Ryanodine Receptor) in Normal and Failing Hearts. Role of Phosphatases and Response to Isoproterenol." J. Biol. Chem., vol. 278, No. 1, pp. 444-453. (2003).

Reiken et al., "Beta-Blockers Restore Calcium Release Channel Function and Improve Cardiac Muscle Performance in Human Heart Failure." Circulation, vol. 107. pp. 2459-2466. (2003).

Reiken, S. et al. "PKA Phosphorylation of the Cardiac Calcium Release Channel (Ryanodine Receptor) in Normal and Failing Hearts: Role of Phosphatases and Response to Isoproterenol." J. Biol. Chem. (2002).

Rensma et al. "Length of Excitation Wave and Susceptibility to Reentrant Atrial Arrhythmias in Normal Conscious Dogs." Circ. Res., vol. 62, pp. 395-410. (1988).

Rosemblit, et al., "Intracellular calcium release channel expression during embryogenesis," Dev. Biol., vol. 206, pp. 163-177 (1999).

Schotten et al., "Electrical and contractile remodeling during the first days of atrial fibrillation go hand and hand," Circulation, vol. 107, pp. 1433-1439. (2003).

Semsarian et al., "The L-Type Calcium Channel Inhibitor Diltiazem Prevents Cardiomyopathy in a Mouse Model." J. Clin. Invest., vol. 109, No. 8, pp. 1013-1020. (2002).

Shibata, "264 W94" Current Opinion in Cardiovascular, Pulmonary, and Renal Investigational Drugs., vol. 1, No. 2, pp. 276-278. (1999).

Shinohara, "A Synthesis of Mono-and Dimethoxy -1,2,3,4—Tetrahydroisoquinolines via Pummerer Reaction: Effects of Methoxyl Groups on Intramolecular Cyclization." Chemical and Pharmaceutical Bulletin, vol. 46, No. 6, pp. 918-927. (1998).

Shiroshita-Takeshita et al., "Atrial fibrillation: basic mechanisms, remodeling and triggers," J. Interv. Card. Electrophysiol, vol. 13, pp. 181-193. (2005).

Shtifman, et al., "Interdomain interactions within ryanodine receptors regulate Ca2+ spark frequency in skeletal muscle," J. Gen. Physiol., vol. 119, pp. 15-31 (2002).

Song, Y. et al. "ATP Promotes Development of Afterdepolarizations and Triggered Activity in Cardiac Myocytes." Am. J. Physiol., vol. 267, pp. H2005-H2011. (1994).

Special Report "Preliminary Report: Effect of Encainide and Flecainide on mortality in a randomized trial of arrhythmia suppression after myocardial infraction," The New England Jour. of Med., vol. 321, No. 6, pp. 406-412. (1989).

Stevenson, W.G. et al., "Sudden death prevention in patients with advanced ventricular dysfunction," Circulation, vol. 88, pp. 2953-2961. 1993.

Sun et al., "Cellular Mechanisms of Atrial Contractile Dysfunction Caused by Sustained Atrial Tachycardia." Circulation, vol. 98, pp. 719-727. (1998).

Swan, et al., "Calcium channel antagonism reduces exercise-induced ventricular arrhythmias in catecholaminergic polymorphic ventricular tachycardia patients with RyR2 mutations," J. of Card. Electrophysiology, vol. 16, No. 2, pp. 162-166, (2005).

Swan, H. et al. "Arrhythmic Disorder Mapped to Chromosome 1q42-q43 Causes Malignant Polymorphic Ventricular Tachycardia in Structurally Normal Hearts." J. Am. Coll. Cardiol., vol. 34, No. 7, pp. 2035-2042. (1999).

Szabo et al. "Synthesis and Spectroscopic Investigation of 1,4-Benzothiazepine Derivatives." Magyar Kemiai Folyoirat, vol. 93, No. 6. pp. 269-276. (1987). (in Hungarian and English).

Szabo et al. "Synthesis and Transformation of 4,5-dihydro-1,4-benzothiazepin-3(2H)—one derivatives." Magyar Kemiai Folyoirat, vol. 93, No. 3, pp. 139-144. (1987). (in Hungarian and English).

Szabo et al. "Synthesis and Transformations of 4,5-Dihydro-1,4-benzothiazepin-3(2H)-one Derivatives1,2)." Chemische Berichte., vol. 119, No. 9, pp. 2904-2913. (1986).

Szabo, Janos et al., "Synthesis and Spectroscopic Investigations of 1,4-benzothiazepine derivatives." Can. J. Chem, vol. 65, pp. 175-181. (1987).

Tester, et al., "Compendium of cardiac channel mutations in 541 consecutive unrelated patients referred for long QT syndrome genetic testing," Heart Rhythm. vol. 2, pp. 507-517 (2005).

Tester, et al., "Targeted mutational analysis of the RyR2-encoded cardiac ryanodine receptor in sudden unexplained death: a molecular authopsy of 40 medical examiner/coroner's cases," May Clin. Proc., vol. 79, pp. 1380-1384 (2004).

Tieleman et al. "Verapamil Reduces Tachycardia-Induced Electrical Remodeling of the Atria." Circulation, vol. 95, pp. 1945-1953 (1997).

Timerman, et al., "The ryanodine receptor from canine heart sacroplasmic reticulum is associated with a novel FK-506 binding protein," Biochem. Biophys. Res. Commun., vol. 198, pp. 701-706 (1994).

Tipton, et al., "My child just fainted: no big deal or sudden-death warning?" Emerg. Med. Serv., vol. 33, pp. 41-45 (2004).

Tse et al. "JTV-519 Japan Tobacco." Curr. Opin. Investig. Drugs. vol. 2, No. 7, pp. 936-939. (2001).

Tunwell et al., "H. Sapiens mRNA for Ryanodine Receptor 2." GenBank Database, Accession No. X98330. Sep. 9, 1996.

Tunwell et al., "The Human Cardiac Muscle Ryanodine Receptor-Calcium Release Channel: Identification, Primary Structure and Topological Analysis." Biochem. J., vol. 318, pp. 477-487. (1996).

Valdivia, Hector H. et al. "Rapid Adaption of Cardiac Ryanodine Receptors: Modulation by Mg2+ and Phosphorylation." Science, vol. 267, pp. 1997-2000. (Mar. 31, 1995).

Wang, et al., "Retinoic acid stimulates annexin-mediated growth plate chondrocyte mineralization," J. Cell Biol., vol. 157, pp. 1061-1069 (2002).

Wang, W., et al., "Annexin-mediated Ca2+ influx regulates growth plate chondrocyte maturation and apoptosis," J. Biol Chem, vol. 278, pp. 3762-3769 (2003).

Wang, ZG et al., "Effects of Flecainide and Quinidine on Human Atrial Action Potentials. Role of rate-dependence and comparison with guinea pig, rabbit, and dog tissues," Circulation, Journal of the American Heart Association, vol. 82, pp. 274-283. 1990.

Ward, et al., "Defects in ryanodine receptor calcium release in skeletal muscle from post-myocardial infarct rats," Faseb J., vol. 17, pp. 1517-1519 (2003).

Wehrens et al. "FKBP12.6 Deficiency and Defective Calcium Release Channel (Ryanodine Receptor) Function Linked to Exercise Induced Sudden Cardiac Death." Cell, vol. 113, pp. 829-840. (2003).

Wehrens, et al., "Altered function and regulation of cardiac ryanodine receptors in cardiac disease," Trends Biochem. Sci., vol. 28, pp. 671-678 (2003).

Wehrens, et al., "Myocardial disease in failing hearts: defective excitation-contraction coupling," Cold Spring Harb. Symp. Quant. Biol., vol. 67, pp. 533-541 (2002).

Wijffels et al. "Atrial Fibrillation Begets Atrial Fibrillation: A Study in Awake Chronically Instrumented Goats." Circulation, vol. 92, pp. 1954-1968. (1995).

Wilde et al., "Ion Channels, the QT interval, and arrhythmias," Pacing Clin Electrophysiol, vol. 20, pp. 2048-2051. 1997.

Wit, A.L. et al. "Pathophysiologic Mechanisms of Cardiac Arrhythmias." Am. Heart. J., vol. 106, pp. 798-811. (1983).

Yamamoto et al. "Abnormal Ca2+ Release from Cardiac Sarcoplasmic Reticulum in Tachycardia-Induced Heart Failure." Cardiovasc. Res., vol. 44, pp. 146-155. (1999).

Yamamoto, et al., "Ca2+-dependent dual function of peptice C. The peptide corresponding to the Glu724-Pro760 region (the so-called determinant of excitation-contraction coupling) of the dihydropyridine receptor alpha 1 subunit II-III loop," J. Biol. Chem., vol. 277, pp. 993-1001 (2002).

Yamamoto, et al., "Peptide probe study of the critical regulatory domain of the cardiac ryanodine receptor," Biochem, Biophys. Res. Commun., vol. 291, pp. 1102-1108 (2002).

Yamamoto, et al., "Spectroscopic monitoring of local conformational changes during the intramolecular domain-domain interaction of the ryanodine receptor," Biochemistry, vol. 41, pp. 1492-1501 (2002).

Yamamoto, et al., "T-tubule depolarization-induced local events in the ryanodine receptor, as monitored with the fluorescent conformational probe incorporated by mediation of peptide A," J. Biol. Chem. vol. 277, pp. 984-992 (2002).

Yang, Jiacheng et al. "A-kinase Achoring Protein 100 (AKAP100) is Localized in Multiple Subcellular Compartments in the Adult Rat Heart." The Journal of Cell Biology, vol. 142, No. 2, pp. 511-522 (Jul. 27, 1998).

Yano et al. "Altered Stoichiometry of FKBP12.6 Versus Ryanodine Receptor as a Cause of Abnormal Ca2+ Leak Through Ryanodine Receptor in Heart Failure." Circulation, vol. 102, pp. 2131-2136. (2000).

Yano, M. et al. "FKBP12.6-Mediated Stabilization of Calcium-Release Channel (Ryanodine Receptor) as a Novel Therapeutic Strategy against Heart Failure." Circulation, vol. 107, pp. 477-484. (2003).

Yue et al., "Ionic Remodeling Underlying Action Potential Changes in a Canine Model of Atrial Fibrillation." Circ. Res., vol. 81, pp. 512-525. (1997).

Zucchi et al., "The Sarcoplasmic Reticulum Ca2+ Channel/Ryanodine Receptor: Modulation by Endogenous Effectors, Drugs, and Disease States." Pharmacological Reviews, vol. 49, No. 1, pp. 1-51. (1997).

Loughrey et al., "K201 modulates excitation-contraction coupling and spontaneous Ca2+ release in normal adult rabbit ventricular cardiomyocytes," Cardiovascular Research, vol. 76, pp. 236-246 (2007).

Supplementary European Search Report for European Patent Application No. 04756121.2, mailed Dec. 21, 2007.

Non Final Office Action mailed Aug. 7, 2001 for U.S. Appl. No. 09/568,474, filed May 10, 2000.

Non Final Office Action mailed Jan. 14, 2002 for U.S. Appl. No. 09/568,474, filed May 10, 2000.

Non Final Office Action mailed on May 4, 2004 for U.S. Appl. No. 10/288,606, filed Nov. 5, 2002.

Final Office Action mailed on Nov. 22, 2004 for U.S. Appl. No. 10/288,606, filed Nov. 5, 2002.

Non Final Office Action Mailed on Jul. 11, 2005 for U.S. Appl. No. 10/288,606, filed Nov. 5, 2002.

Final Office Action mailed on Jan. 5, 2006 for U.S. Appl. No. 10/288,606, filed Nov. 5, 2002.

Non Final Office Action mailed on Jan. 26, 2007 for U.S. Appl. No. 10/288,606, filed Nov. 5, 2002.

Final Office Action mailed on Oct. 5, 2007 for U.S. Appl. No. 10/288,606, filed Nov. 5, 2002.

Non Final Office Action mailed on Mar. 25, 2008 for U.S. Appl. No. 10/288,606, filed Nov. 5, 2002.

Non Final Office Action mailed on Feb. 27, 2007 for U.S. Appl. No. 10/680,988, filed Oct. 7, 2003.

Final Office Action mailed on Nov. 29, 2007 for U.S. Appl. No. 10/680,988, filed Oct. 7, 2003.

Non Final Office Action mailed on Mar. 19, 2008 for U.S. Appl. No. 10/680,988, filed Oct. 7, 2003.

Non Final Office Action mailed on Apr. 27, 2005 for U.S. Appl. No. 10/608,723, filed Jun. 26, 2003.

Final Office Action mailed on Dec. 29, 2005 for U.S. Appl. No. 10/608,723, filed Jun. 26, 2003.

Non Final Office Action mailed on Aug. 23, 2006 for U.S. Appl. No. 10/608,723, filed Jun. 26, 2003.

Final Office Action mailed on Feb. 16, 2007 for U.S. Appl. No. 10/608,723, filed Jun. 26, 2003.

Non Final Office Action mailed on Oct. 30, 2007 for U.S. Appl. No. 10/608,723, filed Jun. 26, 2003.

Final office Action mailed on Mar. 20, 2008 for U.S. Appl. No. 10/608,723, filed Jun. 26, 2003.

Non Final Office Action mailed on Nov. 27, 2007 for U.S. Appl. No. 10/809,089, filed Mar. 25, 2004.

Non Final Office Action mailed on May 3, 2005 for U.S. Appl. No. 10/794,218, filed Mar. 5, 2004.

Non Final Office Action mailed on Jan. 9, 2006 for U.S. Appl. No. 10/794,218, filed Mar. 5, 2004.

Final Office Action mailed on Aug. 23, 2006 for U.S. Appl. No. 10/794,218, filed Mar. 5, 2004.

Non Final Office Action mailed on Aug. 29, 2006 for U.S. Appl. No. 11/088,123, filed Mar. 23, 2005.

Final Office Action mailed on Mar. 27, 2007 for U.S. Appl. No. 11/088,123, filed Mar. 23, 2005.

Islam S., "Perspectives in Diabetes. The Ryanodine Receptor Calcium Channel of β-Cells. Molecular Regulation and Physiological Significance," Diabetes, vol. 51, pp. 1299-1309 (2002).

Johnson et al., "Ryanodine receptors in human pancreatic β cells: localization and effects on insulin secretion1," the FASEB Journal, vol. 18, pp. 878-880 (2004).

Johnson et al., "RyR2 and Calpain-10 Delineate a Novel Apoptosis Pathway in Pancreatic Islets," The Journal of Biological Chemistry, vol. 279, pp. 24794-24802 (2004).

Kang et al., "A cAMP and Ca2+ coincidence detector in support of Ca2+-induced Ca2+ release in mouse pancreatic β cells," J. Physiol, vol. 566, pp. 173-188 (2005).

Kang et al., "cAMP-regulated guanine nucleotide exchange factor II (Epac2) mediates Ca2+-induced Ca2+ release in INS-1 pancreatic β cells," Journal of Physiology, vol. 536.2, pp. 375-385 (2001).

Lehnart et al., "Phosphodiesterase 4D associates with the cardiac calcium release channel (Ryanodine Receptor) and protects from Hypertrophy and heart failure", Circulation, vol. 110, No. 17 Suppl. S, pp. 227-228 (Oct. 26, 2004).

Liu et al., "Crosstalk between the cAMP and Inositol Trisphosphate-Signalling Pathways in Pancreatis β-Cells," Archives of Biochemistry and Biophysics, vol. 334, pp. 295-302 (1996).

Mitchell et al., "Ryanodine Receptor Type I and Nicotinic Acid Adenine Dinucleotide Phosphate Receptors Mediate Ca2+ Release from Insulin-containing Vesicles in Living Pancreatic β-Cells (MIN6)," The Journal of Biological Chemistry, vol. 278, pp. 11057-11064 (2003).

Pereira et al., "Mechanisms of [Ca2+]i Transient Decrease in Cardiomyopathy of db/db Type 2 Diabetic Mice," Diabetes, vol. 55, pp. 608-615 (2006).

Shao et al., "Dyssynchronous (non-uniform) Ca2+ release in myocytes from streptozotocin-induced diabetic rats," Journal of Molecular and Cellular Cardiology, vol. 42, pp. 234-246 (2007).

Takasawa et al., "Cyclic ADP-ribose and Inositol 1,4,5-Trisphosphate as Alternate Second Messengers for Intracellular Ca2+ Mobilization in Normal and Diabetic β-Cells," The Journal of Biological Chemistry, vol. 273, pp. 2497-2500 (1998).

Varadi et al., "Dynamic Imaging of Endoplasmic Reticulm Ca2+ Concentration in Insulin-Secreting MIN6 Cells Using Recombinant Target Cameleons. Role of Sarco (endo) plasmic Reticulum Ca2+-ATPase (SERCA)-2 and Ryanodine Receptors," Diabetes, vol. 51, Suppl. 1, pp. S190-S201 (2002).

Woolcott et al., "Arachidonic acid is a physiological activator of the ryanodine receptor in pancreatic β-cells," Cell Calcium, vol. 39, pp. 529-537 (2006).

Yaras et al., "Effects of Diabetes on Ryanodine Receptor Ca Release Channel (RyR2) and Ca2+ Homeostasis in Rat Heart," Diabetes, vol. 54, pp. 3082-3088 (2005).

Yaras et al., "Restoration of Diabetes-induced abnormal local Ca2+ release in cardiomyocytes by angiotensin II receptor blockade," Am J. Physiol Heart Circ Physiol, vol. 292, pp. H912-H920 (2007).

Zhang et al., "Growth Hormone Promotes Ca2+-induces Ca2+ Release in Insulin-Secreting Cells by Ryanodine Receptor Tyrosine Phosphorylation," Molecular Endocrinology, vol. 18, pp. 1658-1669 (2004).

U.S. Appl. No. 10/763,498, filed Jan. 22, 2004, Marks et al.

"CIBIS-II, The Cardiac Insufficiency Bisoprolol Study II (CIBIS-II): A Randomized Trial." The Lancet, vol. 353, pp. 9-13, (1999).

Ahern et al., "Intramembrane Charge Movements and Excitation-Contraction Coupling Expressed by Two-Domain Fragments of the Ca2+ Channel." Proc Natl Acad Sci USA, vol. 98, No. 12, pp. 6935-6940. (2001).

Ahern et al., "Subconductance States in Single-Channel Activity of Skeletal Muscle Ryanodine Receptors After Removal of FKBP12." Biophys J, vol. 72, pp. 146-162. (1997).

Ahmmed, G.U. et al., "Changes in Ca(2+) Cycling Proteins Underlie Cardiac Action Potential Prolongation in a Pressure-Overloaded Guinea Pig Model with Cardiac Hypertrophy and Failure." Circ. Res., vol. 86, No. 5, pp. 558-570. (2000).

Baille, et al., "beta-Arrestin-mediated PDE4 cAMP phosphodiesterase recruitment regulates beta-adrenoceptor switching from Gs to Gi," Proc. Natl. Acada. Sci. USA 100, 940-945 (2003).

Barnes, P.J., "Theophylline: new perspectives for an.old drug," Am. J. Respir. Crit. Care Med. 167, 813-8 (2003).

Basso, C. et al., "Arrhythmogenic Right Ventricular Cardiomyopathy Causing Sudden Cardiac Death in Boxer Dogs: A New Animal Model of Human Disease." Circulation, vol. 109, No. 9, pp. 1180-1185. (2004).

Bennett et al. "The Pattern of Onset and Spontaneous Cessation of Atrial Fibrillation in Man." Circulation, vol. 41, pp. 981-988. (1970).

Bennett et al., "Synthesis of 2-methoxydibenzo [b,f](1,4)-thiazepin-11 (10H)-one 5,5-dioxide." Organic Preparations and Procedures International, vol. 6, No. 6, pp. 287-293. (1974).

Bezprozvanny, I. et al. "Bell-shaped Calcium Response Curves of Ins (1,4,5) $P_3$- and Calcium-gated Channels from Endoplasic Reticulum of Cerebellum." Nature, vol. 351, pp. 751-754. (1991).

Bittar, et al., "The arrhythmogeneicity of theophylline. A multivariate analysis of clinical determinates," Chest 99, 1415-1420 (1991).

Bohm, M. et al. "cAMP Concentrations, cAMP Dependent Protein Kinase Activity, and Phospholamban in Non-Failing and Failing Myocardium." Cardivasc. Res., vol. 28, No. 11, pp. 1713-1719. (1994).

Bolger, et al., "Characterization of five different proteins produced by alternatively spliced mRNAs from the human cAMP-specific phosphodiesterase PDE4D gene," Biochem. J. 328 (Pt 2), 539-48 (1997).

Boyden et al., "2APB- and JTV519 (K201)—Sensitive Micro $Ca^{2+}$ Waves in Arrythmogenic Purkinje Cells that Survive in Infarcted Canine Heart." Heart Rhythm, vol. 1, pp. 218-226. (2004).

Bristow et al., "Carvedilol Produces Dose-Related Improvements in left Ventricular Function and Survival in Subjects with Chronic Heart Failure." Circulation, vol. 94, pp. 2807-2816. (1996).

Bristow, et al., "Beta 1- and beta 2-adrenergic-receptor subpopulations in nonfailing and failing human ventricular myocardium: coupling of both receptor subtypes to muscle contraction and selective beta I-receptor down-regulation in heart failure," Circ. Res. 59, 297-309 (1986).

Burashnikov et al. "Reinduction of Atrial Fibrillation Immediately After Termination of the Arrhythmia is Mediated by Late Phase 3 Early Afterdepolarization-Induced Triggered Activity." Circulation, vol. 107, No. 2355-2360. (2003).

Callaway, C. et al., "Localization of the High and Low Affinity [$^3$H] Ryanodoine Binding Sites on the Skeletal Muscle $Ca^{2+}$ Release Channel." The Journal of Biological Chemistry, vol. 269, No. 22, pp. 15876-15884. (1994).

Carlisle Michel, et al., "PKA-phosphorylation of PDE4D3 facilitates recruitment of the mAKAP signaling complex," Biochem. J. 381, 587-592 (2004).

Cerrone, M. et al., "Bidirectional Ventricular Tachycardia and Fibrillation Elicited in a Knock-in Mouse Model Carrier of a Mutation in the Cardiac Ryanodine Receptor." Circ. Res., vol. 96, No. 10, e77-82. (2005).

Cheng, H. et al., "Amplitude Distribution of Calcium Sparks in Confocal Images: Theory and Studies with an Automatic Detection Method." Biophys J., vol. 76, pp. 606-617. (1999).

Cohn, J.N. et al. "Plasma Norepinephrine as a Guide to Prognosis in Patients with Chronic Congestive Heart Failure." N. Eng. J. Med., vol. 311, No. 13, pp. 819-823 (1984).

Conti, et al., "Cycli AMP-specific PDE4 phosphodiesterases as critical components of cyclic AMP signaling," J. Biol. Chem. 278, 5493-6 (2003).

Cranefield, P.F. "Action Potentials, Afterpotentials and Arrhythmias." Circ. Res., vol. 41, No. 4, pp. 415-423. (1977).

Dietz et al., "Epinephrine Regulation of Skeletal Muscle Glycogen Metabolism :Studies Utilizing the Perfused Rat Hindlimb Preparation." J. Biol. Chem., vol. 255, No. 6, pp. 2301-2307. (1980).

Dodge K.L., et al. "mAKAP Assembles a Protein Kinase A/PDE4 Phosphodiesterase cAMP Signaling Module." EMBO J. vol. 20, No. 8, pp. 1921-1930. (2001).

Drexler et al. "Contrasting Peripheral Short-Term and Long-Term Effects of Converting Enzyme Inhibition in Patients with Congestive Heart Failure. A Double-Blind, Placebo-Controlled Trial." Circulation, vol. 79, pp. 491-502. (1989).

Dun et al. "Chronic Atrial Fibrillation Does Not Further Decrease Outward Currents. It Increases Them." Am. J. Physiol. Heart Circ. Physiol., vol. 285, pp. H1378-H1384. (2003).

Exhibit I: Structures, 2005.

Feldman, et al., "Deficient production of cyclic AMP: pharmacologic evidence of an important cause of contractile dysfunction in patients with end-stage heart failure," Circulation 75, 331-9 (1987).

Fisher, J.D. et al. "Familial Polymorphic Ventricular Arrhythmias: A Quarter Century of Successful Medical Treatment Based on Serial Exercise-Pharmacologic Testing." J. Am. Coll. Cardiol., vol. 34, No. 7, pp. 2015-2022. (1999).

Fox, P.R., "Spontaneously Occurring Arrhythmogenic Right Ventricular Cardiomyopathy in the Domestic Cat: A New Animal Model Similar to the Human Disease." Circulation, vol. 102, No. 15, pp. 1863-1870. (2000).

Franzen, P. et al. "Cloning of a TGFβ Type I Receptor That Forms a Heteromeric Complex with the TGF beta type II receptor." Cell, vol. 75, pp. 681-692. (1993).

Franzini-Armstrong et al., "Alternate Disposition of Tetrads in Peripheral Couplings of Skeletal Muscle." Journal of Muscle Research & Cell Motility. vol. 16, pp. 319-324. (1995).

Fraser, I.D. et al. "Modulation of Ion Channels: a "current" view of AKAPs." Neuron, vol. 23, pp. 423-426. (1999).

Frazier, O.H. et al. "First Use of an Untethered, Vented Electrc Left Ventricular Assist Device for Long-Term Support." Circulation, vol. 89, pp. 2908-2914. (1994).

Gaburjakova, M. et al. "FKBP12 Binding Modulates Ryanodine Receptor Channel Gating." J. Biol. Chem., vol. 276, No. 20, pp. 16931-16935. (2001).

Giembycz, M.A., "Development status of second generation PDE4 inhibitors for asthma and COPD: the story so far," Monaldi, Arch. Chest Dis. 57, 48-64 (2002).

Gong, et al., "Persistent improvement in synaptic and cognitive functions in an Alzheimer mouse model after rolipram treatment," J. Clin. Invest. 114, 1624-1634 (2004).

Gonzalez et al. "Involvement of Multiple Intracellular Release Channels in Calcium Sparks of Skeletal Muscle." Proc. Natl Acad Sci USA, vol. 97, No. 8, pp. 4380-4385. (2000).

Gretarsdottir, et al., "The gene encoding phosphodiesterase 4D confers risk of ischemic stroke," Nat. Genet. 35, 131-8 (2003).

Gullestad et al., "Effect of Metoprolol CR/XL on Exercise Tolerance in Chronic Heart Failure—a Substudy to the MERIT-HF Trial," Eur. J. Heart Fail, vol. 3, pp. 463-468. (2001).

Hachida et al. "Significant Effect of 1,4-Benzothiazepine Derivative (K2) in Improving Myocardial Preservation." Transplantation Proceedings, vol. 29, pp. 1346-1348. (1997).

Hachida, et al., "Protective Effect of JTV519 (K201), a New 1, 4—Benzothiazepine Derivative, on Prolonged Myocardia Preservation." Transplantation Proceedings, vol. 31, pp. 996-1000. (1999).

Hara et al., "Steady-state and nonsteady State Action Potentials in Fibrillating Canine Atrium: Abnormal Rate Adaption and Its Possible Mechanisms." Cardiovasc. Res., vol. 42, pp. 455-469. (1999).

Harnick, D.J. et al. "The Human Type 1 Inositol 1,4,5-trisphosphate receptor from T Lymphocytes: Structure, Localization, and Tyrosine Phosphorylation." J. Biol. Chem., vol. 270, No. 6, pp. 2833-2840. (1995).

Harrington, D. et al. "Mechanisms of Exercise Intolerance in Congestive Heart Failure." Current Opinion in Cardiology, vol. 12, No. 3, pp. 224-232. (1997).

Hasenfuss et al., "Treatment of Heart Failure Through Stabilization of the Cardiac Ryanodine Receptor." Circulation, vol. 107, pp. 378-380. (2003).

Houslay, et al., "PDE4 cAMP phosphodiesterases: modular enzymes that orchestrate signaling cross-talk, desensitization and compartmentalization," Biochem. J. 370, 1-8 (2003).

Huse, M. et al. "Crystal Structure of the Cytoplasmic Domain of the Type 1 TGFβ Receptor in Complex With FKBP12." Cell, vol. 96, pp. 425-436. (1999).

International Search Report and Written Opinion from PCT/US04/20474, Aug. 30, 2005.

International Search Report and Written Opinion from PCT/US04/32550, Oct. 18, 2005.

International Search Report and Written Opinion from PCT/US05/009495, Mar. 14, 2006.

International Search Report and Written Opinion from PCT/US05/10055, Oct. 27, 2005.

International Search Report and Written Opinion from PCT/US05/45914, Aug. 31, 2006.

Isselbacher, Kurt J. et al. "Harrison's Principles of Internal Medicine." 13th Edition, vol. 1, pp. 1022-1024. (1994).

Jiang et al., "Abnormal $Ca^{2+}$ Release, but Normal Ryanodine Receptors, in Canine and Human Heart Failure." Circulation Research, vol. 91, pp. 1015-1022. (Nov. 29, 2002).

Jiang, D. et al. "Enhanced Basal Activity of a Cardiac $Ca^{2+}$ Release Channel (Ryanodine Receptor) Mutant Asssociated with Ventricular Tachycardia and Sudden Death." Circ. Res., vol. 91, pp. 218-225. (2002).

Jin, S.L.C. et al.: "Impaired growth and fertility of cAMP-specific phosphodiesterase PDE4D-deficient mice," PNAS, Oct. 12, 1999, vol. 96, No. 21, 11998-12003.

Kaneko et al., "Crystal Structure of Annexin V with Its Ligand K-201 as a Calcium Channel Activity Inhibitor." Journal of Molecular Biology, vol. 274, pp. 16-20. (1997).

Kaneko et al., "Inhibition of Annexin V-dependent Ca2 Movement in Large Unilamellar Vesicles by K201, a New." Biochimica et Biophysica Acta, vol. 1330, pp. 1-7. (1997).

Kaneko, N. "New 1,4-benzothiazepine Derivative, K201, Demonstrates Cardio-Protective Effects Against Sudden Cardiac Cell Death and Intracellular Calcium Blocking Action." Drug Dev. Res., vol. 33: pp. 429-438 (1994).

Kapiloff, M.S. et al. "mAKAP:an A-kinase Anchoring Protein Targeted to the Nuclear Membrane of Differentiated Myocytes." J. Cell Sci., vol. 112, pp. 2725-2736. (1999).

Katritzky, et al., "1H and 13C NMR study of tetrahydro-1, 4-benzothiazepine conformations," J. Chem. Soc. 5, 1816-1822 (2002).

Katritzky, et al., Convenient syntheses of 2, 3, 4, 5-tetrahydro-1, 4-benzothiazepines, -1, 4-benzoxazepines and -1, 4-benzodiazepines, J. Chem. Soc. 11, 592-598 (2002).

Katz et al., "Lactate Turnover at Rest and During Submaximal Excercise in Patients with Heart Failure." J. Appl. Physiol., vol. 75, No. 5, pp. 1974-1979. (1993).

Kirchhefer, U. et al. "Activity of cAMP-dependent Protein Kinase and $Ca^{2+}$/calmodulin-dependent Protein Kinase in Failing and Nonfailing Human Hearts." Cardiovasc. Res., vol. 42, pp. 254-261. (1999).

Kirsch et al., "Spark and Ember-Like Elementary $Ca^{2+}$ Release Events in Skinned Fibre of Adult Mammalian Skeletal Muscle." J. Physiol., vol. 537, No. 2, pp. 379-389. (2001).

Kiryu, K. et al. "Pathologic and Electrocardiographic Findings in Sudden Cardiac Death in Racehorses." J. Vet. Med. Sci., vol. 61, No. 8, pp. 921-928. (1999).

Kittleson, M.D. et al., "Familial Hypertrophic Cardiomyopathy in Maine Coon Cats: An Animal Model of Human Disease." Circulation, vol. 99, No. 24, pp. 3172-3180. (1999).

Klein et al., "Voltage Dependence of the Pattern and Frequency of Discrete $Ca^{2+}$ Release Events After Brief Repriming, in Frog Skeletal Muscle." Proc. Natl. Acad. Sci. USA, vol. 94, pp. 11061-11066. (1997).

Kneller et al. "Remodeling of $Ca^{2+}$—handling by Atrial Tachycardia: Evidence for a Role in Loss of Rate-Adaption." Cardiovasc. Res., vol. 54., pp. 416-426. (2002).

Kukin, M.L. et al. "Prospective, Randomized Comparison of Effect of Long-Term Treatment with Metoprolol or Carvedilol on Symptoms, Excercise, Ejection Fraction, and Oxidative Stress in Heart Failure." Circulation, vol. 99, pp. 2645-2651. (1999).

Lacampagne, A. et al., "Modulation of the Frequency of Spontaneous Sarcoplasmic Reticulum $Ca^{2+}$ Release Events ($Ca^{2+}$ Sparks) by Myoplasmic ($Mg^{2+}$) Frog Skeletal Muscle." J. Gen. Physiol. 111, pp. 207-224. (1998).

Laflamme, M.A. et al. "Gs and Adenylyl Cyclase in Transverse Tubules of Heart: Implications for cAMP-dependent signaling." Am. J. Phys., vol. 277, pp. H1841-H1848. (1999).

Lai, F.A., et al., "The Ryanodine Receptor-$Ca^{2+}$ Release Channel Complex of Skeletal Muscle Sarcoplasmic Reticulum. Evidence for a Cooperatively Coupled, Negatively Charged Homotetramer." J. Biol. Chem., vol. 264, No. 28, pp. 16776-16785. (1989).

Lamb et al., "Effects of FK506 and Rapamycin on Excitation-Contraction Coupling in Skeletal Muscle Fibres of the Rat." J Phys, vol. 494, No. 2, pp. 569-576. (1996).

Lauffenburger et al., "Receptors." Oxford University Press, Chapter 2, pp. 9-12. (1996).

Laver et al., "Inactivation of $Ca^{2+}$ Release Channels (Ryanodine Receptors RyR1 and RyR2) with Rapid Steps in [$Ca^{2+}$] and Voltage." Biophys J., vol. 74, pp. 2352-2364. (1998).

Lehnart et al. "Defective Ryanodine Receptor Interdomain Interactions May Contribute to Intracellular $Ca^{2+}$ Leak: A Novel Therapeutic Target in Heart Failure." Circulation, vol. 111, No. 25, pp. 3342-3346. (2005).

Lehnart et al., "Phosphodiesterase 4D Deficiency in the Ryanodine-Receptor Complex Promotes Heart Failure and Arrhythmias." Cells, vol. 123, No. 1, pp. 25-35. (Oct. 7, 2005).

Lehnart et al., "Sudden Death in Familial Polymorphic Ventricular Tachycardia Associated with Calcium Release Channel (Ryanodine Receptor) Leak." Circulation, vol. 109, pp. 3208-3214. (2004).

Levin, H.R. et al. "Reversal of Chronic Ventricular Dilation in Patients with End-Stage Cardiomyopathy by Prolonged Mechanical Unloading." Circulation, vol. 91, pp. 2717-2720. (1995).

Lisy et al., "New Cardioprotective Agent K201 is Natriuretic and Glomerular Filtration Rate Enhancing." Circulation, vol. 113, pp. 246-251. (2006).

Lorenz, M.C. et al. "TOR Mutations Confer Rapamycin Resistance by Preventing Interaction with FKBP12- Rapamycin." J. Biol. Chem., vol. 270, No. 46, pp. 27531-27537. (1995).

Lunde et al., "Contraction and Intracellular Ca2+ Handling in Isolated Skeletal Muscle of Rats with Congestive Heart Failure." Circ. Res., vol. 88, pp. 1299-1305. (2001).

Lunde, et al. "Contractile Properties of in Situ Perfused Skeletal Muscles from Rats with Congestive Heart Failure." J. Physiol, vol. 540, pp. 571-580. (2002).

MacDougall, L.K. et al. "Identification of the Major Protein Phosphatases in Mammalian Cardiac Muscle Which Dephosphorylate Phospholamban." Eur. J. Biochem., vol. 196, pp. 725-734. (1991).

MacFarlane et al. "Cellular Basis for Contractile Dysfunction in the Diaphragm from a Rabbit Infarct Model of Heart Failure." Am. J. Physiol. Cell Physiol., vol. 278. pp. C739-C746. (2000).

Mancini et al., "Contribution of a Skeletal Muscle Atrophy to Exercise Intolerance and Altered Muscle Metabolism in Heart Failure." Circulation, vol. 85, pp. 1364-1373 (1992).

Masumiya et al., "Localization of the 12.6 kDa FK506-binding Protein (FKBP12.6) Binding Site to the $NH_2$ - Terminal Domain of the Cardiac $Ca^{2+}$ Release Channel. (Ryanodine Receptor)." The Journal of Biological Chemistry, vol. 278, pp. 3786-3792. (2003).

McCartney, S. et al. "Cloning and Characterization of A-Kinase Anchor Protein 100 (AKAP100). A Protein That Targets A-Kinase to the Sarcoplasmic Reticulum." J. Biol. Chem., vol. 270, No. 16, pp. 9327-9333. (1995).

Meissner, G., "Ryanodine Receptor/$Ca^{2+}$ Release Channels and Their Regulation by Endogenous Effectors." Annu. Rev. Physiol., vol. 56, pp. 485-508. (1994).

Merit, H.F. "Effect of Metoprolol CR/XL in Chronic Heart Failure: Metoprotol CR/XL Randomised Intervention Trial in Congestive Heart Failure (MERIT-HF)." Lancet, vol. 353, pp. 2001-2007. (1999).

Meurs, K.M. et al., "A Cardiac Myosin Binding Protein C Mutation in the Maine Coon Cat with Familial Hypertrophic Cardiomyopathy." Hum Mol Genet, vol. 14, No. 23, pp. 3587-3593. (2005).

Meurs, KM. "Boxer Dog Cardiomyopathy: An Update." Vet Clin North Am Small Anim Pract., vol. 34, pp. 1235-1244. (2004).

Miller, K.B., "Manganese Alters Mitochodrial Integrity in the Hearts of Swine Marginally Deficient in Magnesium." Biofactors, vol. 20, No. 2, pp. 85-96. (2004).

Minotti et al., "Impaired Skeletal Muscle Function in Patients with Congestive Heart Failure. Relationship to Systemic Excercise Performance." J. Clin. Invest., vol. 88, pp. 2077-2082. (1991).

Mitchell, G.F. et al. "Measurement of Heart Rate and Q-T Interval in the Conscious Mouse." Am. J. Physiol., vol. 274, pp. H747-H751. (1998).

Moghadam, H.K. "Heritability of Sudden Death Syndrome and Its Associated Correlations to Ascites and Body Weight in Broilers." Br Poult Sci, vol. 46, No. 1, pp. 54-57. (2005).

Mohler, P.J. et al. "Ankyrin-B Mutation Causes Type 4 long-QT Cardiac Arrhythmia and Sudden Cardiac Death." Nature, vol. 421, pp. 634-639. (2003).

Moise, N.S., "Inherited Arrhythmias in the Dog: Potential Experimental Models of Cardiac Disease." Cardiovasc Res, vol. 44, No. 1, pp. 37-46. (1999).

Mongillo, et al., "Fluorescence resonance energy transfer-based analysis of cAMP dynamics in live neonatal rat cardiac myocytes reveals distinct functions of compartmentalized phosphodiesterases," Cir. Res., 95, 67-75 (2004).

Morgan, J. et al. "Abnormal Intracellular Calcium Handling: A Major Cause of Systolic and Diastolic Dysfunction in Ventricular Myocardium from Patients with heart failure." Circulation, vol. 81 (Suppl. 3), pp. III21-III32. (1990).

Moschella, M.C. et al. : Inositol 1,4,5-trisphosphate Receptor Expression in Cardiac Myocytes. J. Cell. Biol., vol. 120, No. 5, pp. 1137-1146. (1993).

Nair, et al., "Synthesis and reactions of 1, 4-benzothiazepine derivatives," IJOCAP, 7(9), 862-5 (1969).

Nakai, et al., "Functional Nonequality of the Cardiac and Skeletal Ryanodine Receptors," Proc. Natl. Acad. Sci. USA, vol. 94, pp. 1019-1022, Feb. 1997.

Nakamura, Y. et al., "Parasitic Females of Strongyloides Papillosus as a Pathogenetic Stage for Sudden Cardiac Death in Infected Lambs." J. Vet Med. Sci., vol. 56, No. 4, pp. 723-727. (1994).

Neumann, J. et al. "Increased Expression of Cardiac Phosphatases in Patients with End-Stage Heart Failure." J. Mol. Cell. Cardiol., vol. 29, pp. 265-272. (1997).

Otsu, K. et al. "Molecular Cloning of cDNA encoding the $Ca^{2+}$ release channel (Ryanodine Receptor) of Rabbit Cardiac Muscle Sarcoplasmic Reticulum." J. Biol. Chem., vol. 265, No. 23, pp. 13472-13483. (1990).

Oyama, Mark A. et al., "Genomic Expression Patterns of Cardiac Tissues from Dogs with Dilated Cardiomyopathy." AJVR, vol. 66, No. 7, pp. 1140-1155. (Jul. 2005).

Packer, et al., "Effect of oral milrinone on mortality in severe chronic heart failure. The PROMISE Study Research Group," N. Engl. J. Med. 325, 1468-75 (1991).

Perreault et al., "Alterations in Contractility and Intracellular $Ca^{2+}$ Transients in Isolated Bundles of Skeletal Muscle Fibers from Rats with Chronic Heart Failure." Circ. Res., vol. 73, No. 2, pp. 405-412. (1993).

Perry, et al., "Targeting of cyclic AMP degradation to beta 2-adrenergic receptors by beta-arrestins," Science 298, 834-6 (2002).

Pieske, et al., "Ca2+ handling and sarcoplasmic reticulum Ca2+ content in isolated failing and nonfailing human myocardium," Circ. Res. 85, 38-46 (1999).

Pogwidz, S.M. et al. "Mechanisms Underlying Spontaneous and Induced Ventricular Arrhythmias in Patients with Idiopathic Dilated Cardiomyopathy." Circulation, vol. 98, pp. 2404-2414. (1998).

Pogwidz, S.M. et al. "Arrhythmogenesis and Contractile Dysfunction in Heart Failure: Roles of Sodium-Calcium Exchange, Inward Rectifier Potassium Current, and Residual Beta-Adrenergic Responsiveness." Circ. Res., vol. 88, pp. 1159-1167. (2001).

Protas, L. et al. "Regional Dispersion of L-type Calcium Current in Ventricular Myocytes of German Shepherd Dogs with Lethal Cardiac Arrhythmias." Heart Rhythm, vol. 2, Issue. 2, pp. 172-176. (2005).

Ramirez et al., "Mathematical Analysis of Canine Atrial Action Potentials: Rate, Regional Factors and Electrical Remodeling." Am. J. Physiol. Heart Circ. Physiol., vol. 279, pp. H1767-H1785. (2000).

Regitz-Zagrosek, et al. "Myocardial Cyclic AMP and Norepinephrine Content in Human Heart Failure." Eur. Heart J, 15 Suppl. D: pp. 7-13. (1994).

Reiken et al., "A Novel Excitation-Contraction (EC) Coupling Myopathy in Heart Failure Involving Both Cardiac and Skeletal Muscles." Circulation, vol. 104, No. 17 Supplement, pp. II. 131. (Oct. 23, 2001).

Reiken et al., "Defective Skeletal Muscle Calcium Release Channel Function during Heart Failure." Circulation, vol. 106, No. 19 Supplement, pp. II-225. (2002).

Reiken, S. et al. "Beta-Adrenergic Receptor Blockers Restore Cardiac Calcium Release Channel (Ryanodine Receptor) Structure and Function in Heart Failure." Circulation, vol. 104, pp. 2843-2848. (2001).

Reiken, S. et al. "Protein Kinase A Phosphorylation of the Cardiac Calcium Release Channel (Ryanodine Receptor) in Normal and Failing Hearts. Role of Phosphatases and Response to Isoproterenol." J. Biol. Chem., vol. 278, pp. 444-453. (2003).

Reiner, G. et al., "Skeletal Muscle Sarcoplasmic Calcium Regulation and Sudden Death Syndrome in Chickens." Br Poult Sci., vol. 36, No. 4, pp. 667-675. (1995).

Richter, et al., "Splice variants of the cyclic nucleotide phosphodiesterase PDE4D are differentially expressed and regulated in rat tissue," Biochem. N. 388, 803-811 (2005).

Rios et al., "Charge Movement and the Nature of Signal Transduction in Skeletal Muscle Excitation-Contraction Coupling." Annu Rev Physiol, vol. 54, pp. 109-133. (1992).

Rios et al., "Involvement of Dihydropyridine Receptors in Excitation-Contraction Coupling in Skeletal Muscle." Nature, vol. 325, pp. 717-720. (1987).

Ruehr, et al., "Targeting the protein kinase A by muscle A kinase-anchoring protein (mAKAP) regulates phosphorylation and function of the skeletal muscle ryanodine receptor," J. Biol. Chem. 278, 24831-24836 (2003).

Schneider et al., "Voltage Dependent Charge Movement in Skeletal Muscle: A Possible Step in Excitation-Contraction Coupling." Nature, vol. 242, pp. 244-246. (1973).

Shoenmakers et al., "CHELATOR: An Improved Method for Computing Metal Ion Concentrations in Physiological Solutions." Biocomputing, vol. 12, pp. 870-879. (1992).

Sen, L.Y. et al. "Inotropic and Calcium Kinetic Effects of Calcium Channel Agonist and Antagonist in Isloated Cardiac Myocytes from Cardiomyopathic Hamsters." Circ Res, vol. 67, No. 3, pp. 599-608. (1990).

Sette, et al., "Phosphorylation and activation of a cAMP-specific phosphodiesterase by the cAMP-dependent protein kinase. Involvement of serine 54 in the enzyme activation," J. Biol. Chem. 271, 16526-34 (1996).

Sette, et al., "The ratPDE3/Ivd phosphodiesterase gene codes for multiple proteins differentially activated by cAMP-dependent protein kinase," J. Biol. Chem. 269, 18271-4 (1994).

Shannon, et al., "Elevated sarcoplasmic reticulum Ca2+ leak in intact ventricular myocytes from rabbits in heart failure," Circ. Res. 93, 592-4 (2003).

Shirokova, N. et al., "Local Calcium Release in Mammalian Skeletal Muscle." J. Physiol. vol. 512, No. 2, pp. 377-384. (1998).

Shou, W. et al. "Cardiac Defects and Altered Ryanodine Receptor Function in Mice Lacking FKBP12." Nature, vol. 391, pp. 489-492. (1998).

Sonnleitner et al., "Gating of the Skeletal Calcium Release Channel by ATP is Inhibited by Protein Phosphatase 1 but not by $Mg^{2+}$," Cell Calcium 21, No. 4, pp. 283-290. (1997).

Sorensen et al., "Excercised Blood Flow and Microvascular Distensibility in Skeletal Muscle Normalize After Heart Transplantation." Clin. Transplant, vol. 13, pp. 410-419. (1999).

Stratton et al., "Effects of Cardiac transplantation on Bioenergetic Abnormalities of Skeletal Muscle in Congestive Heart Failure." Circulation, vol. 89, pp. 1624-1631. (1994).

Suissa, et al., "Bronchodilators and acute cardiac death," Am. J. Respir. Crit. Care Med. 154, 1598-1602 (1996).

Suko et al., "Phosphorylation of Serine 2843 in Ryanodine Receptor-Calcium Release Channel of Skeletal Muscle by cAMP-, cGMP- and CaM-Dependent Protein Kinase." Bioch Biophys. Acta., vol. 1175, pp. 193-206. (1993).

Sullivan et al., "Excercise Intolerance in Patients with Chronic Heart Failure." Prog. Cardiovasc. Dis., vol. 38, No. 1, pp. 1-22. (1995).

Takeshima, H. et al. "Primary Structure and Expression from Complementary DNA of Skeletal Muscle Ryanodine Receptor." Nature, vol. 339, pp. 439-445. (1989).

Tanabe, T. et al., "Regions of the Skeletal Muscle Dihydropyridine Receptor Critical for Excitation-Contraction Coupling." Nature, vol. 346, pp. 567-569. (1990).

Tasken, et al., "Phosphodiesterase 4D and protein kinase a type Ii constitue a signaling unit in the centrosomal area," J. Biol. Chem. 276, 21999-2002 (2001).

Timerman, Anthony P. et al., "The Calcium Release Channel of Sarcoplasmic Reticulum is Modulated by FK-506- binding Protein." J. Bio. Chem., vol. 268, No. 31, p. 22992-22999. (1993).

Timmermanns et al., "Immediate Reinitiation of Atrial Fibrillation Following Internal Atrial Defibrillation." J. Cardiovasc. Electrophysiol., vol. 9, pp. 122-128. (1998).

Tsuji, N. et al., "Sudden Cardiac Death in Calves with Experimental Heavy Infection of Strongyloides Papillosus." J. Vet. Med. Sci., vol. 54, No. 6, pp. 1137-1143. (1992).

Tunwell et al., "H. Sapiens mRNA for Ryanodine Receptor 2." GenBank Database, Accession No. X98330. Sep. 9, 1996.

van Rooij, et al., "MCIPI overexpression suppresses left ventricular remodeling and sustains cardiac function after mycardial infarction," Circ. Res. 94, e18-26 (2004).

Verde, et al., "Characterization of the cyclic nucleotide phosphodiesterase subtypes involved in the regulation of the L-type Ca2+ current in rat ventricular myocytes," Br. J. Pharmacol. 127, 65-74 (1999).

Vest, J.A. et al., "Defective Cardiac Ryanodine Receptor Regulation During Atrial Fibrillation." Circulation. vol. 111, No. 16, pp. 2025-2032. (2005).

Vignola, A.M., "PDE4 inhibitors in COPD—a more sselective approach to treatment," Respir. Med. 98, 495-503 (2004).

von Altrock, A., "Sudden Deaths in Fattening Herds on taking Blood Samples- Experiences from the Practice." Berl Munch Tierarztl Wschr, vol. 112, pp. 86-90. (1999).

Wang et al. "Regional and Functional Factors Determining Induction and Maintenance of Atrial Fibrillation in Dogs." Am. J. Physiol., vol. 271, pp. H148-H158. (1996).

Wang, et al., "Cloning and characterization of novel PDE4D isoforms PDE4D6 and PDE4D7," Cell. Signal. 15, 883-891 (2003).

Wang, J. et al. "Physical Training Alters the Pathogenesis of Pacing-Induced Heart Failure Through Endothelium-Mediated Mechanisms in Awake Dogs." Circulation, vol. 96, pp. 2683-2692. (1997).

Wehrens et al. "Ca2+/Calmodulin-Dependent Protein Kinase II Phosphorylation Regulates the Cardiac Ryanodine Receptor." Circ. Res., vol. 94, No. 6. pp. e61-e70. (Apr. 2004).

Wehrens et al. "Enhancing Calstabin Binding to Ryanodine Receptors Improves Cardiac and Skeletal Muscle Function in Heart Failure." Proc Natl Acad Sci USA, vol. 102, No. 27, pp. 9607-9612. (Jul. 5, 2005).

Wehrens et al., "Enhancing Calstabin Binding to Ryanodine Receptors Improves Cardiac and Skeletal Muscle Function in Heart Failure." PNAS, vol. 102, No. 27, pp. 9607-9612. (2005).

Wehrens et al., "Molecular Determinants of Altered Contractility in Heart Failure." Ann Med., vol. 36, Suppl. 1, pp. 70-80. (2004).

Wehrens et al., "Novel Therapeutic Approaches for Heart Failure by Normalizing Calcium Cycling." Nature Reviews Drug Discovery., vol. 3, pp. 565-573. (2004).

Wehrens et al., "Protection from Cardiac Arrhythmia Through Ryanodine Receptor-Stabilizing Protein Calstabin2." Science, vol. 304, pp. 292-296. (Apr. 2004).

Wehrens et al., "Ryanodine Receptor-Targeted Anti-Arrhythmic Therapy." Ann N. Y. Acad. Sci., vol. 1047, pp. 366-375. (2005).

Wehrens et al. "Sudden Unexplained Death Caused by Cardiac Ryanodine Receptor (RyR2) Mutations." Mayo Clin Proc., vol. 79, No. 11, pp. 1367-1371. (Nov. 2004).

Wehrens, et al., "Intracellular Calcium Release Channels and Cardiac Disease," Annu. Rev. Physiol. (2004).

Wellens et al., "Atrioverter: An Implantable Device for the Treatment of Atrial fibrillation." Circulation, vol. 98, pp. 1651-1656. (1998).

Westphal, R.S. et al. "Regulation of NMDA Receptors by an Associated Phosphatase-Kinase Signaling Complex." Science, vol. 285, pp. 93-96. (1999).

Wilson, et al. "Exertional Fatigue Due to Skeletal Muscle Dysfunction in Patients with Heart Failure." Circulation, vol. 87, pp. 470-475. (1993).

Wilson, J.R. "Exercise Intolerance in Heart Failure. Importance of Skeletal Muscle." Circulation, vol. 91, pp. 559-561. (1995).

Xiang, Y. et al.: "Phosphodiesterase 4D is required for $\beta_2$adrenoceptor subtype-specific signaling in cardiac myocytes," PNAS, Jan. 18, 2005, vol. 102, No. 3, 909-914.

Xin, H.B. et al. "Oestrogen Protects FKBP12.6 Null Mice from Cardiac Hypertrophy." Nature, vol. 416, pp. 334-337. (2002).

Yamamoto-Hino, M. et al. "Cloning and Characterization of Human Type 2 and Type 3 Inositol 1,4,5-trisphosphate Receptors." Receptor Channels, vol. 2, pp. 9-22. (1994).

Yamawaza, et al., "Subtype Specificity of the Ryanodine Receptor for $Ca^{2+}$ Signal Amplification in the Excitation-Contraction Coupling," The EMBO Journal, vol. 15, No. 22, pp. 6172-6177, 1996.

Yano et al., "RyR-Bound FKBP12.6 and the Modulation." Journal Clinical Calcium, vol. 11, No. 6, pp. 743-748. (Jun. 11, 2001).

Yu et al., "Tachycardia-induced Change of Atrial Refractory Period in Humans: Rate Dependency and Effects of Antiarrhythmic Drugs." Circulation, vol. 97, pp. 2331-2337. (1998).

Zaccolo, et al., "Discrete micro domains with high concentration of cAMP in stimulated rat neonatal cardiac myocytes," Science 295, 1711-5 (2002).

Marks et al. Phosphodiesterase 4D deficiency in the ryanodine-receptor complex promotes heart failure and arrhythmias Cell. Oct. 7, 2005;123(1):25-35. (Abstract only).

Marks et al. Ryanodine receptor-targeted anti-arrhythmic therapy. Ann N Y Acad Sci. Jun. 2005;1047:366-75. (Abstract only).

Marks et al. Defective ryanodine receptor interdomain interactions may contribute to intercellular Ca2+ leak: a novel therapeutic target in heart failure. Circulation. Jun. 28, 2005;111(25):3342-6. (No abstract available).

Marks et al.Enhancing calstabin binding to ryanodine receptors improves cardiac and skeletal muscle function in heart failure. Proc Natl Acad Sci U S A. Jul. 5, 2005;102(27):9607-12 (Abstract only).

Marks et al. Defective cardiac ryanodine receptor regulation during atrial fibrillation. Circulation. Apr. 26, 2005;111(16):2025-32 (Abstract only).

Marks et al Sudden unexplained death caused by cardiac ryanodine receptor (RyR2) mutations. Mayo Clin Proc. Nov. 2004;79(11):1367-71. (No abstract available).

Marks et al.Cardiac ryanodine receptor function and regulation in heart disease. Ann N Y Acad Sci. May 2004;1015:144-59 (Abstract only).

Marks et al. Molecular determinants of altered contractility in heart failure. Ann Med. 2004;36 Suppl 1:70-80 (Abstract only).

Marks et al. Ca2+/calmodulin-dependent protein kinase II phosphorylation regulates the cardiac ryanodine receptor. Circ Res. Apr. 2, 2004;94(6):e61-70.

Marks et al. Protein kinase A phosphorylation of the cardiac calcium release channel (ryanodine receptor) in normal and failing hearts. Role of phosphatases and response to isoproterenol. J Biol Chem. Jan. 3, 2003;278(1):444-53.

Gailly, "New Aspects of Calcium signaling in skeletal muscle cells: implications in Duchenne muscular Dystrophy," Biochemica et Biophysica Acta, vol. 1600, pp. 38-44 (2002).

International Preliminary Report on Patentability from International Application PCT/US2005/010055, mailed Oct. 4, 2007.

International Preliminary Report on Patentability from International Application PCT/US2005/010056, mailed Oct. 4, 2007.

International Search Report and Written Opinion from International Patent Application No PCT/US06/32405, Dec. 7, 2007.

LaFerla, "Calcium Dyshomeostasis and Intracellular signalling in Alzheimer's disease," Nature Reviews, vol. 3, pp. 862-872 (Nov. 2002).

Mackenzie et all, "The Role of inositol 1,4,5-trisphosphate receptors in Ca2+ signalling and the generation of arrhythmias in rat atrila myocytes," J. Physiol., vol. 541, pp. 395-409 (2002).

Taur et al., "The Cardiac Ryanodine Receptor (RyR2) and its Role in Heart Disease," Cardiology in Review, vol. 13, No. 3, pp. 142-146 (2005).

Ackerman, MJ, "Cardiac channelopathies: it's in the genes," Nat. Med., vol. 10, pp. 463-464 (2004).

Alvarez et al. "Late Post Myocardial Infarcation Induces a Tetradotoxin-Resistant Na+ Current in Rat Cardiomyocytes." J. Mol. Cell Cardiol, vol. 32, pp. 1169-1179. (2000).

Antos et al. "Dilated Cardiomyopathy and Sudden Death Resulting from Constitute Activation of Protein Kinase A." Circ. Res., vol. 89, pp. 997-1004. (2001).

Bangur, et al., "Mutational analysis of the D1/E1 core helices and the conserved N-terminal region of yeast transcription factor IIB (TFIIB): identification of an N-terminal mutant that stabilizes TATA-binding protein-TFIIB-DNA complexes," Mol. Cell Biol., vol. 17, pp. 6784-6793 (1997).

Barbone et al. "Comparison of Right and Left Ventricular Responses to Left Ventricular Assist Device Support in Patients with Severe Heart Failure: A Primary Role of Mechanical Unloading Underlying Reverse Remodeling." Circulation, vol. 104, pp. 670-675, Aug. 7, 2001.

Behr, et al., "Cardiological assessment of first-degree relatives in sudden arrhythmic death syndrome," The Lancet, vol. 362, 1457-59 (2003).

Bennett, J.A. et al. "Identification and Characterization of the Murine FK506 Binding Protein (FKBP) 12.6 gene." Mamm. Genome, vol. 9, pp. 1069-1071. (1998).

Bidasee et al., "Chronic Diabetes Increases Advanced Glycation End Products on Cardiac Ryanodine Receptors/Calcium-Release Channels," Diabetes, vol. 52, pp. 1825-1836, Jul. 2003.

Bidasee et al., "Diabetes Increases Formation of Advanced Glycation End Products on Sarco (endo) plasmic Reticulum Ca2+-ATPase," Diabetes, vol. 53, pp. 463-473 (2004).

Bruton et al., "Ryanodine receptors of pancreatic β-cells mediate a distinct context-dependent signal for insulin secretion," the FASEB Journal, vol. 17, pp. 301-303 (2003).

Buijs et al., "β-Adrenergic activation reveals impaired cardia calcium handling at early stage of diabetes," Life Sciences, vol. 76, pp. 1083-1098 (2005).

Dyachok et al., "Ca2+-induced Ca2+ release by activation of inositol 1,4,5-trisphosphate receptors in primary pancreatic β-cells," Cell Calcium, vol. 36, pp. 1-9 (2004).

Dyachok et al., "Ca2+-induced Ca2+ Release via Inositol 1,4,5-trisphosphate Receptors Is Amplified by Protein Kinase and Triggers Exocytosis in Pancreatic β-Cells," The Journal of Biological Chemistry, vol. 279, No. 44, pp. 45455-45461 (2004).

Eisner et al., "The Ryanodine Receptor: Cause or Consequence of Diabetic Heart Failure ?.," J. Moll Cell Cardiol, vol. 32, pp. 1377-1378 (2000).

Holz et al., "cAMP-dependent Mobilization of Intracellular Ca2+ Stores by Activation of Ryanodine Receptors in Pancreatic β-Cells," The Journal of Biological Chemistry, vol. 274, pp. 14147-14156 (1999).

International Preliminary Report on Patentability from International Application PCT/US2005/045914, mailed Jun. 28, 2007.

International Search Report and Written Opinion from PCT/US2005/10056, Jun. 5, 2007.

Islam et al., "Effects of caffeine on cytoplasmic free Ca2+ concentration in pancreatic β-cells are mediated by interaction with ATP-sensitive K+ channels and L-type voltage-gated Ca2+ channels but not ryanodine receptor," Biochem. J., vol. 306, pp. 679-686 (1995).

Islam et al., "In situ activation of the type 2 ryanodine receptor in pacreatic beta cells requires cAMP-dependent phosphorylation," Proc. Natl. Acad. Sci. USA, vol. 95, pp. 6145-6150 (1998).

Kiriyama et al. Effects of JTV-519, a novel anti-ischaemic drug on the delayed rectifier K+ current in guinea-pig ventricular myocytes., Naunyn Schmiedebergs Arch Pharmacol. 361(6): 646-653, 2000.

International Search Report and Written Opinion for International Patent Application No. PCT/US04/06971, mailed Jun. 25, 2008.

Non Final Office action mailed on Sep. 4, 2008 for U.S. Appl. No. 10/809,089 filed Mar. 25, 2004.

Tomaselli et al., "What causes Suddent Death in Heart Failure ?," Circulation Research, vol. 95 (8), pp. 754-763 (2004).

Salama et al., "Mouse models of long QT syndrome," J. Physiol 578 (1); pp. 43-53 (2006).

International Search Report and Written Opinion for International Patent Application No. PCT/US07/09715, mailed Aug. 21, 2008.

International Search Report and Written Opinion for International Patent Application No. PCT/US07/18147, mailed Sep. 8, 2008.

International Search Report and Written Opinion for International Patent Application No. PCT/US07/18138, mailed Aug. 26, 2008.

Giordano et al., "Rapamycin antagonizes NF-KappaB nuclear translocation activated by TNF-alpha in primary vascular smooth muscle cells and enhances apoptosis," Am J. Physiol Heart circu Physiol, vol. 290, pp. 2459-2465, (2006).

International Search Report an Written opinion mailed Aug. 14, 2008, for International Application No. PCT/US07/09289 filed Apr. 13, 2007.

International Search Report and Written Opinion mailed Oct. 28, 2008 for International Patent Application No. PCT/US07/12936 filed Jun. 1, 2007.

Non Final Office Action mailed Oct. 20, 2008 for U.S. Appl. No. 11/212,309, filed Aug. 25, 2005.

Non Final Office Action mailed Oct. 20, 2008 for U.S. Appl. No. 11/212,413, filed Aug. 25, 2005.

Zahradka et al., "Activation of MMP-2 in response to vascular injury is mediated by phosphatidylinositol 3-kinase-Dependent expression of MT1-MMP," Am J. Physiol Heart Circ. Physiol, vol. 287, pp. H2861-H2870 (2004).

International Search Report and Written Opinion mailed Jan. 10, 2008 for International Patent Application No. PCT/US07/12969 filed Jun. 1, 2007.

Non Final Office Action mailed Sep. 17, 2008 for U.S. Appl. No. 11/305,528, filed Dec. 16, 2005.

S4

S7

S-20

S-24

S-25

S-26

S-27

S36

ANTI-ARRYTHMIC AND HEART FAILURE DRUGS THAT TARGET THE LEAK IN THE RYANODINE RECEPTOR (RYR2)

CROSS-REFERENCE TO RELATED APPLICATIONS

This Application is a Continuation of U.S. patent application Ser. No. 10/763,498, filed on Jan. 22, 2004, now abandoned, the contents of which are hereby incorporated by reference thereto.

STATEMENT OF GOVERNMENT INTEREST

This invention was made with government support under NIH Grant No. PO1 HL 67849-01. As such, the United States government has certain rights in this invention.

BACKGROUND OF THE INVENTION

Despite advances in treatment, congestive heart failure remains an important cause of mortality in Western countries. Heart failure affects 5 million individuals in the United States alone, and is characterized by a 5-year mortality rate of ~50% (Levy et al., Long-term trends in the incidence of and survival with heart failure. *N. Engl. J Med.*, 347:1397-402, 2002). An important hallmark of heart failure is reduced myocardial contractility (Gwathmey et al., Abnormal intracellular calcium handling in myocardium from patients with end-stage heart failure. *Circ. Res.*, 61:70-76, 1987).

In healthy heart muscle, and other striated muscle, calcium-release channels on the sarcoplasmic reticulum (SR), including ryanodine receptors (RyRs), facilitate coupling of the action potential to a muscle cell's contraction (i.e., excitation-contraction (EC) coupling). Contraction is initiated when calcium ($Ca^{2+}$) is released from the SR into the surrounding cytoplasm. In heart failure, contractile abnormalities result, in part, from alterations in the signaling cascade that allows the cardiac action potential to trigger contraction. In particular, in failing hearts, the amplitude of the whole-cell $Ca^{2+}$ transient is decreased (Beuckelmann et al., Intracellular calcium handling in isolated ventricular myocytes from patients with terminal heart failure. *Circ.*, 85:1046-55, 1992; Gomez et al., Defective excitation-contraction coupling in experimental cardiac hypertrophy and heart failure. *Science*, 276:800-06, 1997), and the duration prolonged (Beuckelmann et al., Intracellular calcium handling in isolated ventricular myocytes from patients with terminal heart failure. *Circ.*, 85:1046-55, 1992).

Cardiac arrhythmia, a common feature of heart failure, results in many of the deaths associated with the disease. Atrial fibrillation (AF) is the most common cardiac arrhythmia in humans, and represents a major cause of morbidity and mortality (Chugh et al., Epidemiology and natural history of atrial fibrillation: clinical implications. *J. Am. Coll. Cardiol.*, 37:371-78, 2001; Falk, R. H., Atrial fibrillation. *N. Engl. J. Med.*, 344:1067-78, 2001). Despite AF's clinical importance, the molecular mechanisms underlying this arrhythmia are poorly understood, and treatment options are limited.

It is well established that structural and electrical remodeling—including shortening of atrial refractoriness, loss of rate-related adaptation of refractoriness (Wijffels et al., Atrial fibrillation begets atrial fibrillation: a study in awake chronically instrumented goats. *Circulation*, 92:1954-68, 1995; Morillo et al., Chronic rapid atrial pacing: structural, functional, and electrophysiological characteristics of a new model of sustained atrial fibrillation. *Circulation*, 91:1588-95, 1995; Elvan et al., Pacing-induced chronic atrial fibrillation impairs sinus node function in dogs: electrophysiological remodeling. *Circulation*, 94:2953-60, 1996; Gaspo et al., Functional mechanisms underlying tachycardia-induced sustained atrial fibrillation in a chronic dog model. *Circulation*, 96:4027-35, 1997), and shortening of the wavelength of re-entrant wavelets—accompany sustained tachycardia (Rensma et al., Length of excitation wave and susceptibility to reentrant atrial arrhythmias in normal conscious dogs. *Circ. Res.*, 62:395-410, 1988). This remodeling is likely important in the development, maintenance and progression of atrial fibrillation.

Previous studies suggest that calcium handling may play a role in electrical remodeling in atrial fibrillation (Sun et al., Cellular mechanisms of atrial contractile dysfunction caused by sustained atrial tachycardia. *Circulation*, 98:719-27, 1998; Goette et al., Electrical remodeling in atrial fibrillation: time course and mechanisms. *Circulation*, 94:2968-74, 1996; Daoud et al., Effect of verapamil and procainamide on atrial fibrillation-induced electrical remodeling in humans. *Circulation*, 96:1542-50, 1997; Yu et al., Tachycardia-induced change of atrial refractory period in humans: rate dependency and effects of antiarrhythmic drugs. *Circulation*, 97:2331-37, 1998; Leistad et al., Atrial contractile dysfunction after short-term atrial fibrillation is reduced by verapamil but increased by BAY K8644. *Circulation*, 93:1747-54, 1996; Tieleman et al., Verapamil reduces tachycardia-induced electrical remodeling of the atria. *Circulation*, 95:1945-53, 1997). However, regulation of RyR2 during atrial fibrillations has not previously been reported.

Approximately 50% of all patients with heart disease die from fatal cardiac arrhythmias. In some cases, a ventricular arrhythmia in the heart may be rapidly fatal—a phenomenon referred to as "sudden cardiac death" (SCD). Fatal ventricular arrhythmias (and SCD) may also occur in young, otherwise-healthy individuals who are not known to have structural heart disease. In fact, ventricular arrhythmia is the most common cause of sudden death in otherwise-healthy individuals.

Catecholaminergic polymorphic ventricular tachycardia (CPVT) is an inherited disorder in individuals with structurally-normal hearts. It is characterized by stress-induced ventricular tachycardia—a lethal arrhythmia that may cause SCD. In subjects with CPVT, physical exertion and/or stress induce bidirectional and/or polymorphic ventricular tachycardias that lead to SCD in the absence of detectable structural heart disease (Laitinen et al., Mutations of the cardiac ryanodine receptor (RyR2) gene in familial polymorphic ventricular tachycardia. *Circulation*, 103:485-90, 2001; Leenhardt et al., Catecholaminergic polymorphic ventricular tachycardia in children: a 7-year follow-up of 21 patients. *Circulation*, 91:1512-19, 1995; Priori et al., Clinical and molecular characterization of patients with catecholaminergic polymorphic ventricular tachycardia. *Circulation*, 106:69-74, 2002; Priori et al., Mutations in the cardiac ryanodine receptor gene (hRyR2) underlie catecholaminergic polymorphic ventricular tachycardia. *Circulation*, 103:196-200, 2001; Swan et al., Arrhythmic disorder mapped to chromosome 1q42-q43 causes malignant polymorphic ventricular tachycardia in structurally normal hearts. *J. Am. Coll. Cardiol.*, 34:2035-42, 1999).

CPVT is predominantly inherited in an autosomal-dominant fashion. Individuals with CPVT have ventricular arrhythmias when subjected to exercise, but do not develop arrhythmias at rest. Linkage studies and direct sequencing have identified mutations in the human RyR2 gene, on chromosome 1q42-q43, in individuals with CPVT (Laitinen et al., Mutations of the cardiac ryanodine receptor (RyR2) gene in familial polymorphic ventricular tachycardia. *Circulation*, 103:485-90, 2001; Priori et al., Mutations in the cardiac ryanodine receptor gene (hRyR2) underlie catecholaminergic polymorphic ventricular tachycardia. *Circulation*, 103:196-200, 2001; Swan et al., Arrhythmic disorder mapped to chromosome 1q42-q43 causes malignant polymorphic ventricular tachycardia in structurally normal hearts. *J. Am. Coll. Cardiol.*, 34:2035-42, 1999).

There are three types of ryanodine receptors, all of which are highly-related $Ca^{2+}$ channels: RyR1, RyR2, and RyR3. RyR1 is found in skeletal muscle, RyR2 is found in the heart, and RyR3 is located in the brain. The type 2 ryanodine receptor (RyR2) is the major $Ca^{2+}$-release channel required for EC coupling and muscle contraction in cardiac striated muscle.

RyR2 channels are packed into dense arrays in specialized regions of the SR that release intracellular stores of $Ca^{2+}$, and thereby trigger muscle contraction (Marx et al., Coupled gating between individual skeletal muscle $Ca^{2+}$ release channels (ryanodine receptors). *Science*, 281:818-21, 1998). During EC coupling, depolarization of the cardiac-muscle cell membrane, in phase zero of the action potential, activates voltage-gated $Ca^{2+}$ channels. In turn, $Ca^{2+}$ influx through these channels initiates $Ca^{2+}$ release from the SR via RyR2, in a process known as $Ca^{2+}$-induced $Ca^{2+}$ release (Fabiato, A., Calcium-induced release of calcium from the cardiac sarcoplasmic reticulum. *Am. J. Physiol.*, 245 :C1-C14, 1983; Nabauer et al., Regulation of calcium release is gated by calcium current, not gating charge, in cardiac myocytes. *Science*, 244:800-03, 1989). The RyR2-mediated, $Ca^{2+}$-induced $Ca^{2+}$ release then activates the contractile proteins which are responsible for cardiac muscle contraction.

RyR2 is a protein complex comprising four 565,000-dalton RyR2 polypeptides in association with four 12,000-dalton FK506 binding proteins (FKBPs), specifically FKBP12.6 (calstabin). FKBPs are cis-trans peptidyl-prolyl isomerases that are widely expressed and serve a variety of cellular functions (Marks, A. R., Cellular functions of immunophilins. *Physiol. Rev.*, 76:631-49, 1996). FKBP12 proteins are tightly bound to, and regulate the function of, the skeletal ryanodine receptor, RyR1 (Brillantes et al., Stabilization of calcium release channel (ryanodine receptor) function by FK506-binding protein. *Cell*, 77:513-23, 1994; Jayaraman et al., FK506 binding protein associated with the calcium release channel (ryanodine receptor). *J. Biol. Chem.*, 267:9474-77, 1992); the cardiac ryanodine receptor, RyR2 (Kaftan et al., Effects of rapamycin on ryanodine receptor/Ca(2+)-release channels from cardiac muscle. *Circ. Res.*, 78:990-97, 1996); a related intracellular $Ca^{2+}$-release channel, known as the type 1 inositol 1,4,5-triphosphate receptor (IP3R1) (Cameron et al., FKBP12 binds the inositol 1,4,5-trisphosphate receptor at leucine-proline (1400-1401) and anchors calcineurin to this FK506-like domain. *J. Biol. Chem.*, 272:27582-88, 1997); and the type I transforming growth factor β (TGFβ) receptor (TβRI)(Chen et al., Mechanism of TGFbeta receptor inhibition by FKBP12. *EMBO J.*, 16:3866-76, 1997). FKBP12.6 binds to the RyR2 channel (one molecule per RyR2 subunit), stabilizes RyR2-channel function (Brillantes et al., Stabilization of calcium release channel (ryanodine receptor) function by FK506-binding protein. *Cell*, 77:513-23, 1994), and facilitates coupled gating between neighboring RyR2 channels (Marx et al., Coupled gating between individual skeletal muscle $Ca^{2+}$ release channels (ryanodine receptors). *Science*, 281:818-21, 1998), thereby preventing aberrant activation of the channel during the resting phase of the cardiac cycle.

Phosphorylation of cardiac RyR2 by protein kinase (PKA) is an important part of the "fight or flight" response that increases cardiac EC coupling gain by augmenting the amount of $Ca^{2+}$ released for a given trigger (Marks, A. R., Cardiac intracellular calcium release channels: role in heart failure. *Circ. Res.*, 87:8-11, 2000). This signaling pathway provides a mechanism by which activation of the sympathetic nervous system, in response to stress, results in increased cardiac output required to meet the metabolic demands of the stress responses. Upon binding of catecholamines, β1- and β2-adrenergic receptors activate adenylyl cyclase via a stimulatory G-protein, $G\alpha_S$. Adenylyl cyclase increases intracellular cAMP levels, which activate the cAMP-dependent PKA. PKA phosphorylation of RyR2 increases the open probability of the channel by dissociating calstabin2 (FKBP12.6) from the channel complex. This, in turn, increases the sensitivity of RyR2 to $Ca^{2+}$-dependent activation (Hain et al., Phosphorylation modulates the function of the calcium release channel of sarcoplasmic reticulum from cardiac muscle. *J. Biol. Chem.*, 270:2074-81, 1995; Valdivia et al., Rapid adaptation of cardiac ryanodine receptors: modulation by $Mg^{2+}$ and phosphorylation. *Science*, 267:1997-2000, 1995; Marx et al., PKA phosphorylation dissociates FKBP12.6 from the calcium release channel (ryanodine receptor): defective regulation in failing hearts. *Cell*, 101:365-76, 2000).

Failing hearts (e.g., in patients with heart failure and in animal models of heart failure) are characterized by a maladaptive response that includes chronic hyperadrenergic stimulation (Bristow et al., Decreased catecholamine sensitivity and beta-adrenergic-receptor ensity in failing human hearts. *N. Engl. J. Med.*, 307:205-11, 1982). The pathogenic significance of this stimulation in heart failure is supported by therapeutic strategies that decrease beta-adrenergic stimulation and left ventricular myocardial wall stress, and potently reverse ventricular remodeling (Barbone et al., Comparison of right and left ventricular responses to left ventricular assist device support in patients with severe heart failure: a primary role of mechanical unloading underlying reverse remodeling. *Circulation*, 104:670-75, 2001; Eichhom and Bristow, Medical therapy can improve the biological properties of the chronically failing heart. A new era in the treatment of heart failure. *Circulation*, 94:2285-96, 1996). In heart failure, chronic beta-adrenergic stimulation is associated with the activation of beta-adrenergic receptors in the heart, which, through coupling with G-proteins, activate adenylyl cyclase and thereby increase intracellular cAMP concentration. cAMP activates cAMP-dependent PKA, which has been shown to induce hyperphosphorylation of RyR2. Thus, chronic heart failure is a chronic hyperadrenergic state (Chidsey et al., Augmentation of plasma norepinephrine response to exercise in patients with congestive heart failure. *N. Engl. J. Med.*, 267:650, 1962) which results in several pathologic consequences, including PKA hyperphosphorylation of RyR2 (Marx et al., PKA phosphorylation dissociates FKBP12.6 from the calcium release channel (ryanodine receptor): defective regulation in failing hearts. *Cell*, 101: 365-76, 2000).

The PKA hyperphosphorylation of RyR2 has been proposed as a factor contributing to depressed contractile function and arrhythmogenesis in heart failure (Marks et al., Progression of heart failure: is protein kinase a hyperphosphorylation of the ryanodine receptor a contributing factor? *Circulation*, 105:272-75, 2002; Marx et al., PKA phosphorylation dissociates FKBP12.6 from the calcium release channel (ryanodine receptor): defective regulation in failing hearts. *Cell*, 101:365-76, 2000). Consistent with this hypothesis, PKA hyperphosphorylation of RyR2 in failing hearts has been demonstrated in vivo, both in animal models and in patients with heart failure undergoing cardiac transplantation (Antos et al., Dilated cardiomyopathy and sudden death resulting from constitutive activation of protein kinase A. *Circ. Res.*, 89:997-1004, 2001; Marx et al., PKA phosphorylation dissociates FKBP12.6 from the calcium release channel (ryanodine receptor): defective regulation in failing hearts. *Cell*, 101:365-76, 2000; Ono et al., Altered interaction of FKBP12.6 with ryanodine receptor as a cause of abnormal $Ca^{2+}$ release in heart failure. *Cardiovasc. Res.*, 48:323-31, 2000; Reiken et al., Beta-adrenergic receptor blockers restore cardiac calcium release channel (ryanodine receptor) structure and function in heart failure. *Circulation*, 104:2843-48, 2001; Semsarian et al., The L-type calcium channel inhibitor diltiazem prevents cardiomyopathy in a mouse model. *J. Clin. Invest.*, 109:1013-20, 2002; Yano et al., Altered stoichiometry of FKBP12.6 versus ryanodine receptor as a cause of abnormal $Ca^{2+}$ leak through ryanodine receptor in heart failure. *Circulation*, 102:2131-36, 2000).

In failing hearts, the hyperphosphorylation of RyR2 by PKA induces the dissociation of the regulatory FKBP12.6 subunit from the RyR2 channel (Marx et al., PKA phosphorylation dissociates FKBP12.6 from the calcium release channel (ryanodine receptor): defective regulation in failing hearts. *Cell*, 101:365-76, 2000). This causes marked changes in the biophysical properties of the RyR2 channel. Such changes are evidenced by increased open probability (Po), due to an increased sensitivity to $Ca^{2+}$-dependent activation (Brillantes et al., Stabilization of calcium release channel (ryanodine receptor) function by FK506-binding protein. *Cell*, 77:513-23, 1994; Kaftan et al., Effects of rapamycin on ryanodine receptor/$Ca^{2+}$-release channels from cardiac muscle. *Circ. Res.*, 78:990-97, 1996); destabilization of the channel, resulting in subconductance states; and impaired coupled gating of the channels, resulting in defective EC coupling and cardiac dysfunction (Marx et al., Coupled gating between individual skeletal muscle $Ca^{2+}$ release channels (ryanodine receptors). *Science*, 281:818-21, 1998). Thus, PKA-hyperphosphorylated RyR2 is very sensitive to low-level $Ca^{2+}$ stimulation, and this manifests itself as an SR $Ca^{2+}$ leak through the hyperphosphorylated channel.

The maladaptive response to stress in heart failure results in depletion of FKBP12.6 from the channel macromolecular complex. This leads to a shift to the left in the sensitivity of RyR2 to $Ca^{2+}$-induced $Ca^{2+}$ release, resulting in channels that are more active at low-to-moderate [$Ca^{2+}$] (Marx et al., PKA phosphorylation dissociates FKBP12.6 from the calcium release channel (ryanodine receptor): defective regulation in failing hearts. *Cell*, 101:365-76, 2000; Yamamoto et al., Abnormal $Ca^{2+}$ release from cardiac sarcoplasmric reticulum in tachycardia-induced heart failure. *Cardiovasc. Res.*, 44:146-55, 1999; Yano et al., Altered stoichiometry of FKBP12.6 versus ryanodine receptor as a cause of abnormal $Ca^{2+}$ leak through ryanodine receptor in heart failure. *Circulation*, 102:2131-36, 2000). Over time, the increased "leak" through RyR2 results in resetting of the SR $Ca^{2+}$ content to a lower level, which in turn reduces EC coupling gain and contributes to impaired systolic contractility (Marx et al., PKA phosphorylation dissociates FKBP12.6 from the calcium release channel (ryanodine receptor): defective regulation in failing hearts. *Cell*, 101:365-76, 2000).

Additionally, a subpopulation of RyR2 that are particularly "leaky" can release SR $Ca^{2+}$ during the resting phase of the cardiac cycle, diastole. This results in depolarizations of the cardiomyocyte membrane known as delayed after-depolarizations (DADs), which are known to trigger fatal ventricular cardiac arrhythmias (Wehrens et al., FKBP12.6 deficiency and defective calcium release channel (ryanodine receptor) function linked to exercise-induced sudden cardiac death. *Cell*, 113:829-40, 2003).

In structurally-normal hearts, a similar phenomenon may be at work. Specifically, it is known that exercise and stress induce the release of catecholamines that activate beta-adrenergic receptors in the heart. Activation of the beta-adrenergic receptors leads to hyperphosphorylation of RyR2 channels. Evidence also suggests that the hyperphosphorylation of RyR2 resulting from beta-adrenergic-receptor activation renders mutated RyR2 channels more likely to open in the relaxation phase of the cardiac cycle, increasing the likelihood of arrhythmias.

Cardiac arrhythmias are known to be associated with SR $Ca^{2+}$ leaks in structurally-normal hearts. In these cases, the most common mechanism for induction and maintenance of ventricular tachycardia is abnormal automaticity. One form of abnormal automaticity, known as triggered arrhythmia, is associated with aberrant release of SR $Ca^{2+}$, which initiates DADs (Fozzard, H. A., Afterdepolarizations and triggered activity. *Basic Res. Cardiol.*, 87:105-13, 1992; Wit and Rosen, Pathophysiologic mechanisms of cardiac arrhythmias. *Am. Heart J.*, 106:798-811, 1983). DADs are abnormal depolarizations in cardiomyocytes that occur after repolarization of a cardiac action potential. The molecular basis for the abnormal SR $Ca^{2+}$ release that results in DADs has not been fully elucidated. However, DADs are known to be blocked by ryanodine, providing evidence that RyR2 may play a key role in the pathogenesis of this aberrant $Ca^{2+}$ release (Marban et al., Mechanisms of arrhythmogenic delayed and early afterdepolarizations in ferret ventricular muscle. *J. Clin. Invest.*, 78:1185-92, 1986; Song and Belardinelli, ATP promotes development of afterdepolarizations and triggered activity in cardiac myocytes. *Am. J. Physiol.*, 267:H2005-11, 1994).

In view of the foregoing, it is clear that leaks in RyR2 channels are associated with a number of pathological states—in both diseased hearts and structurally-normal hearts. Accordingly, methods to repair the leaks in RyR2 could prevent heart failure, and fatal arrhythmias and fibrillations, in millions of patients.

JTV-519 (4-[3-(4-benzylpiperidin-1-yl)propionyl]-7-methoxy-2,3,4,5-tetrahydro-1,4-benzothiazepine monohydrochloride; also known as k201 or ICP-Calstan 100), a derivative of 1,4-benzothiazepine, is a new modulator of calcium-ion channels. In addition to regulating $Ca^{2+}$ levels in myocardial cells, JTV-519 also modulates the $Na^+$ current and the inward-rectifier $K^+$ current in guinea pig ventricular cells, and inhibits the delayed-rectifier $K^+$ current in guinea pig atrial cells. Studies have shown that JTV-519 has a strong cardioprotective effect against catecholamine-induced myocardial injury, myocardial-injury-induced myofibrillar overcontraction, and ischemia/reperfusion injury. In experimental myofibrillar overcontraction models, JTV-519 demonstrated greater cardioprotective effects than propranolol, verapamil, and diltiazem. Experimental data also suggest that JTV-519 effectively prevents ventricular ischemia/reperfusion by reducing the level of intracellular $Ca^{2+}$ overload in animal models.

SUMMARY OF THE INVENTION

The present invention is based upon the surprising discovery that RyR2 is a target for treating and preventing heart failure and cardiac arrhythmias, including atrial fibrillations and cardiac arrhythmias that cause exercise-induced sudden cardiac death (SCD). As described herein, the inventors made mutant RyR2 channels with 7 different CPVT mutations, and studied their functions. All 7 mutants had functional defects that resulted in channels that became leaky (a calcium leak) when stimulated during exercise. The inventors' study is the first to identify a mechanism by which the SR calcium leak causes DADs. Remarkably, the defect in the mutant CPVT channels made the channels look like the leaky channels in the hearts of patients with end-stage heart failure—a disorder characterized by a high incidence of fatal cardiac arrhythmias. Therefore, the inventors demonstrate herein that the mechanism for the VT in CPVT is the same as the mechanism for VT in heart failure.

The inventors also disclose herein that the drug JTV-519 (k201 or ICP-Calstan 100), a member of the 1,4 benzothiazepine family of compounds, repairs the leak in RyR2 channels. As the inventors show herein, JTV-519 enhances binding of FKBP12.6 to PKA-phosphorylated RyR2, and to mutant RyR2s that otherwise have reduced affinity for, or do not bind to, FKBP12.6. This action of JTV-519 fixes the leak in RyR2 that triggers fatal cardiac arrhythmias (cardiac death) and that contributes to atrial/ventricular fibrillations and heart muscle dysfunction in heart failure.

Accordingly, in one aspect, the present invention provides novel 1,4-benzothiazepine intermediates and derivatives, as well as methods for synthesizing same, and methods for assaying for same. In certain embodiments, these novel 1,4-benzothiazepine intermediates and derivatives include:

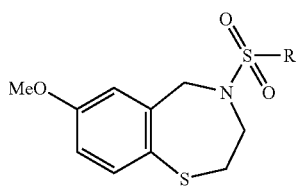

(a)

wherein R=aryl, alkenyl, alkyl, —$(CH_2)_nNR'_2$, or —$(CH_2)_nSR'$, and n=0, 1, 2, or 3, and R'=alkyl or cycloalkyl;

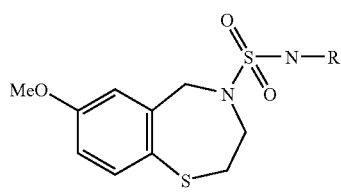

(b)

wherein R=aryl, alkyl, —$(CH_2)_nNR'_2$, or —$(CH_2)_nSR'$, and n=0, 1, 2, or 3, and R'=alkyl or cycloalkyl;

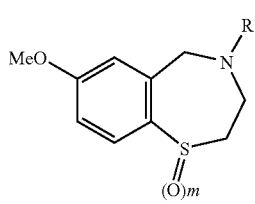

(c)

wherein R=CO$(CH_2)_nXR'_2$, $SO_2(CH_2)_nXR'_2$, or $SO_2NH(CH_2)_nXR'_2$, and X=N or S, and n=1, 2, or 3, and R'=alkyl or cycloalkyl; and wherein m=1 or 2;

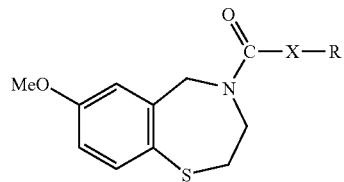

(d)

wherein R=aryl, alkyl, —$(CH_2)_nNR'_2$, —$(CH_2)_nSR'$, and n=0, 1, 2, or 3, and R'=alkyl or cycloalkyl; and wherein X=NH or O; and

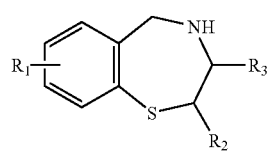

(e)

wherein $R_1$=OR', SR', NR', alkyl, or halide, at position 2, 3, 4, or 5 on the phenyl ring, and R'=alkyl, aryl, or H; wherein $R_2$=H, alkyl, or aryl; and wherein $R_3$=H, alkyl, or aryl. Additional embodiments may include the following compounds: S7, S-20, S-25, S-27, and S36 (set forth in FIG. 8).

Also provided are uses of the novel 1,4-benzothiazepine compounds in methods for limiting or preventing a decrease in the level of RyR2-bound FKBP12.6 in a subject; in methods for treating or preventing heart failure, atrial fibrillation, or exercise-induced cardiac arrhythmia in a subject; and in methods for preventing exercise-induced sudden cardiac death in a subject.

In a further aspect, the present invention provides a method for identifying an agent that enhances binding of RyR2 and FKBP12.6, comprising the steps of: (a) obtaining or generating a source of RyR2; (b) exposing the RyR2 to FKBP12.6, in the presence of a candidate agent; and (c) determining if the agent enhances the binding of RyR2 and FKBP12.6. In certain embodiments, the RyR2 may be unphosphorylated, PKA-phosphorylated, or PKA-hyperphosphorylated. Also provided are an agent identified by this method, and uses of the agent in methods for limiting or preventing a decrease in the level of RyR2-bound FKBP12.6 in a subject; in methods for treating or preventing heart failure, atrial fibrillation, or exercise-induced cardiac arrhythmia in a subject; and in methods for preventing exercise-induced sudden cardiac death in a subject.

In still another aspect, the present invention provides a method for identifying an agent for enhancing the binding of RyR2 and FKBP12.6, comprising the steps of: (a) obtaining or generating a source of FKBP12.6; (b) exposing the FKBP12.6 to RyR2, in the presence of a candidate agent; and (c) determining if the agent enhances the binding of RyR2 and FKBP12.6. In certain embodiments, the RyR2 may be unphosphorylated, PKA-phosphorylated, or PKA-hyperphosphorylated. Also provided are an agent identified by this method, and uses of the agent in methods for limiting or preventing a decrease in the level of RyR2-bound FKBP12.6 in a subject; in methods for treating or preventing heart failure, atrial fibrillation, or exercise-induced cardiac arrhythmia in a subject; and in methods for preventing exercise-induced sudden cardiac death in a subject.

Additional aspects of the present invention will be apparent in view of the description which follows.

application of 1 µM JTV-519 (left panel) or 1 µM JTV-S36 (right panel). The voltage-clamp protocol is shown below the current traces. Currents were elicited during 400-msec depolarization to +80 mV, from a holding potential of −90 mV. It should be noted that, upon the 400-msec depolarization (which mimics the human action potential duration (APD)), hERG channels pass very little outward current, because they rapidly inactivate. Tail currents marked by circles in current traces were elicited by return of the membrane potential to −40 mV, in the recovery from inactivation through the open state. Because the tail current is a major contributor to control of the APD, effects of the drugs were evaluated by tail currents at −40 mV: JTV-519=83% block; JTV-S36=39% block.

Figure 4:
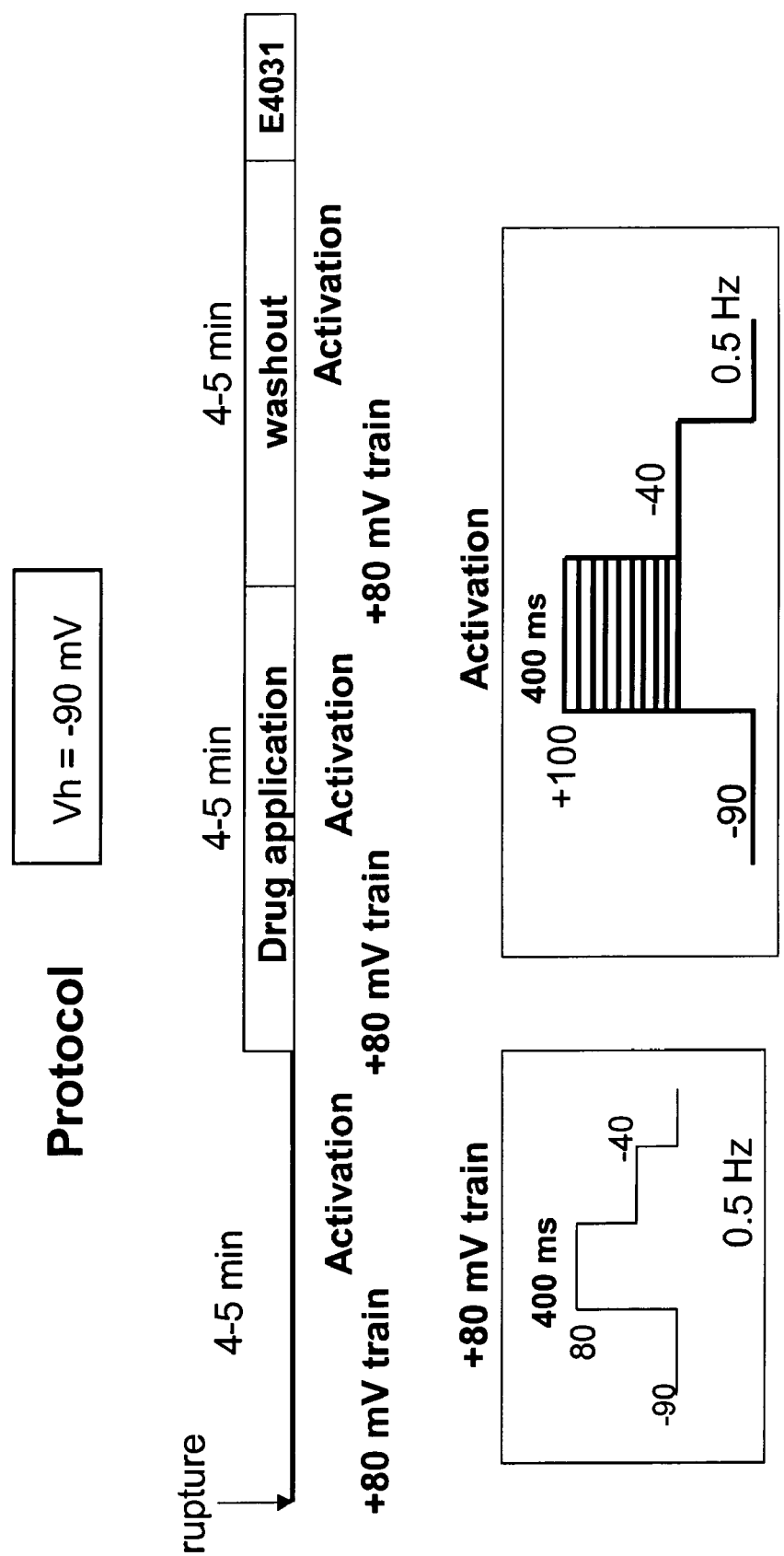
FIG. 4 demonstrates the experimental protocol used to test effects of the inventors' novel JTV-519-related compounds (disclosed herein) on hERG-channel current. Whole-cell patch-clamp experiments were carried out with physiological solutions at room temperature, in CHO cells transfected with hERG channel. Voltage-clamp protocols are shown in the lower panels. In vehicle, 0.1% DMSO in the external solution was applied with the same time-protocol as that shown in the upper panel.
Figure 5:
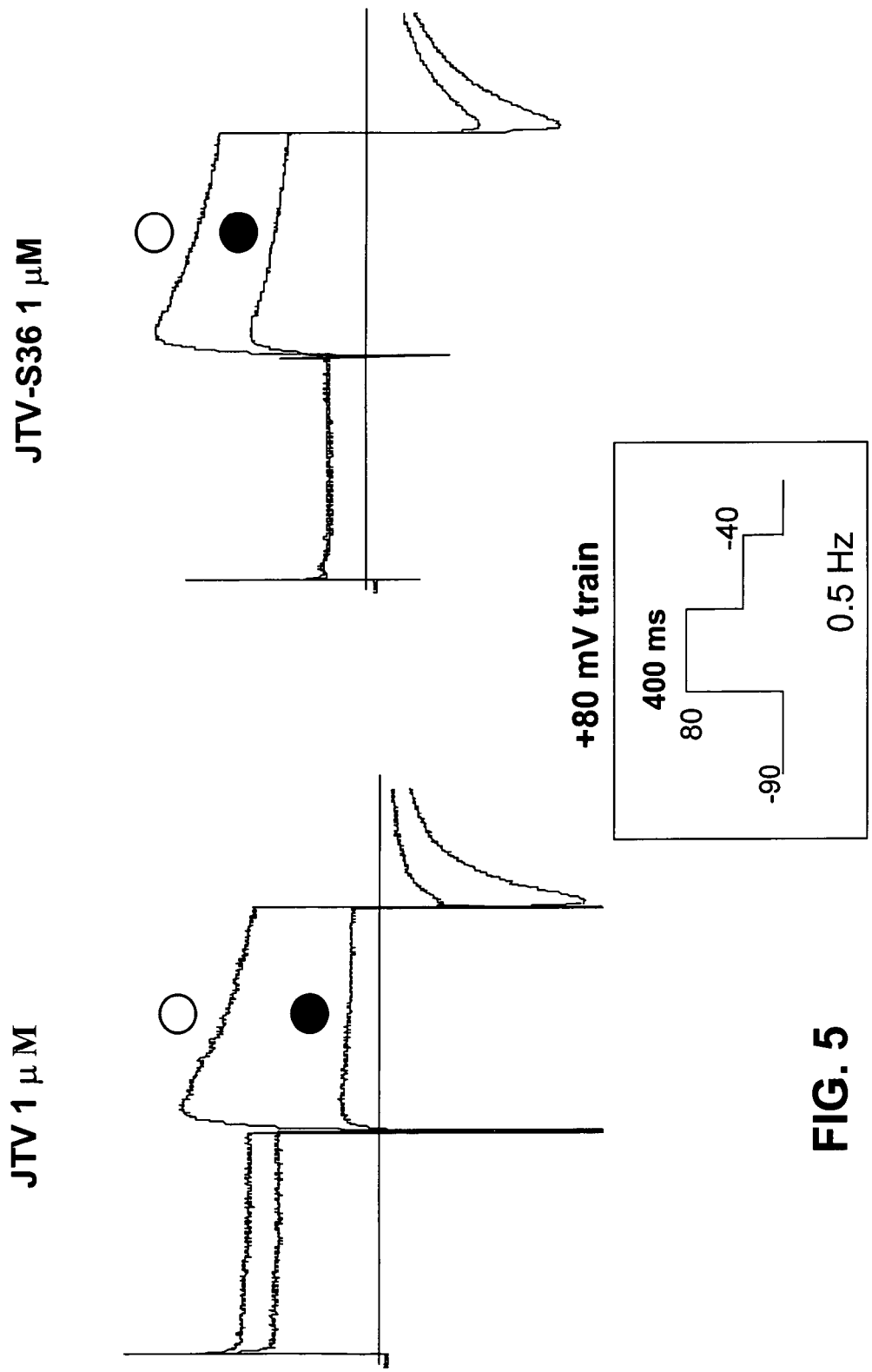
FIG. 5 illustrates the effects of JTV-519 and the inventors' novel JTV-519-related compound, S36 (disclosed herein), on hERG-channel currents elicited by 80-mV depolarization. Representative hERG-channel currents (I(Kr)) were recorded from CHO cells before (open circle) and after (closed circle)
Figure 6:
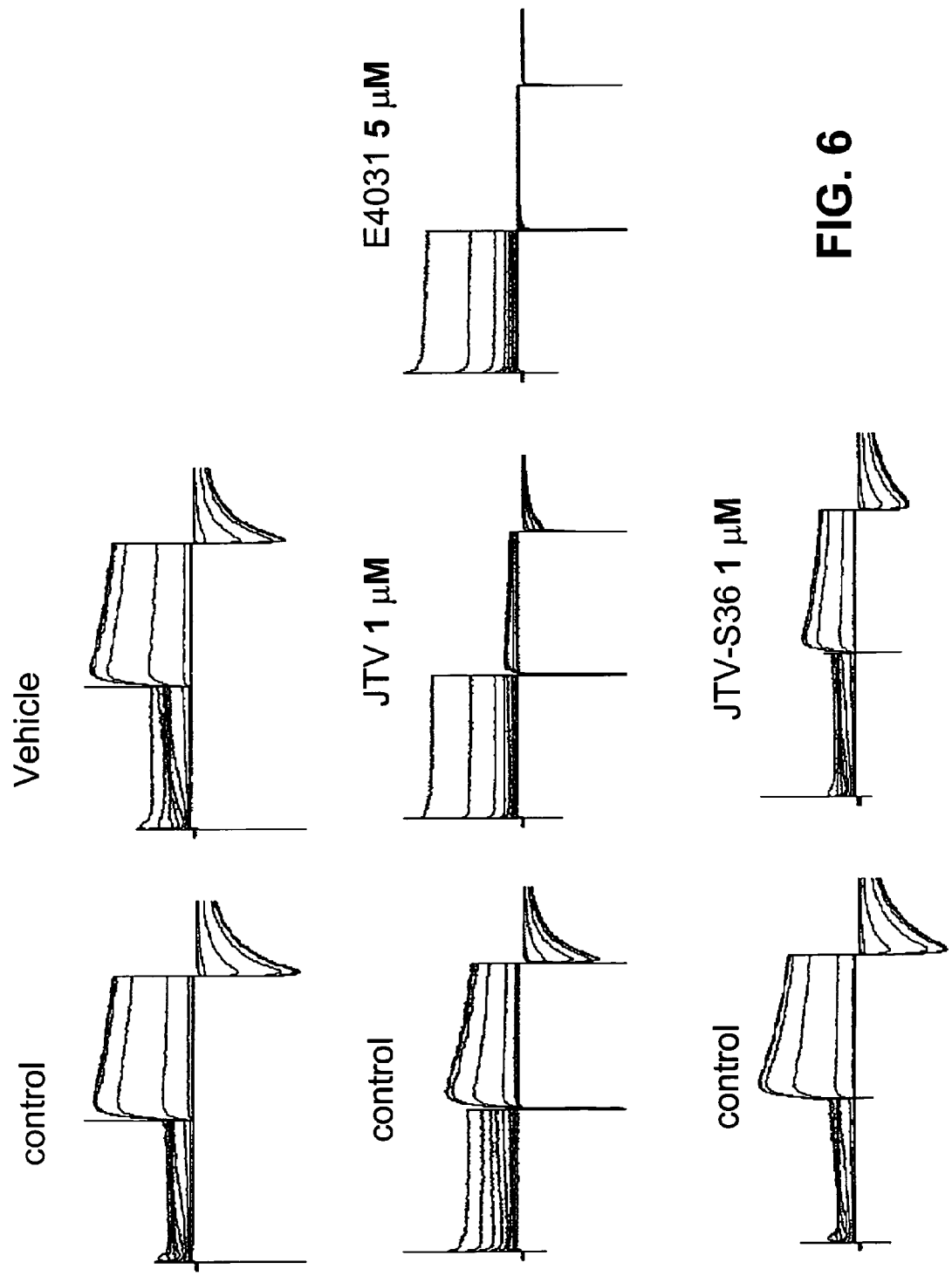

FIG. 6 shows effects of JTV-519, E4031, and the inventors' novel JTV-519-related compound, S36 (disclosed herein), on activation of hERG-channel currents (traces). Representative hERG-channel I-V relationships are shown before (control, left panels) and after (central panels) application of 0.1% DMSO (vehicle; upper central panel), 1 µM JTV-519 (middle central panel), and 1 µM JTV-S36 (lower central panel). The right panel shows that 5 µM E4031 (a class III anti-arrhythmic drug known to block hERG channels) completely blocked hERG-channel currents. (Note the tail currents at −40 mV). The voltage-clamp protocol is set forth in FIG. 4, as an I-V relationship.

Figure 7:
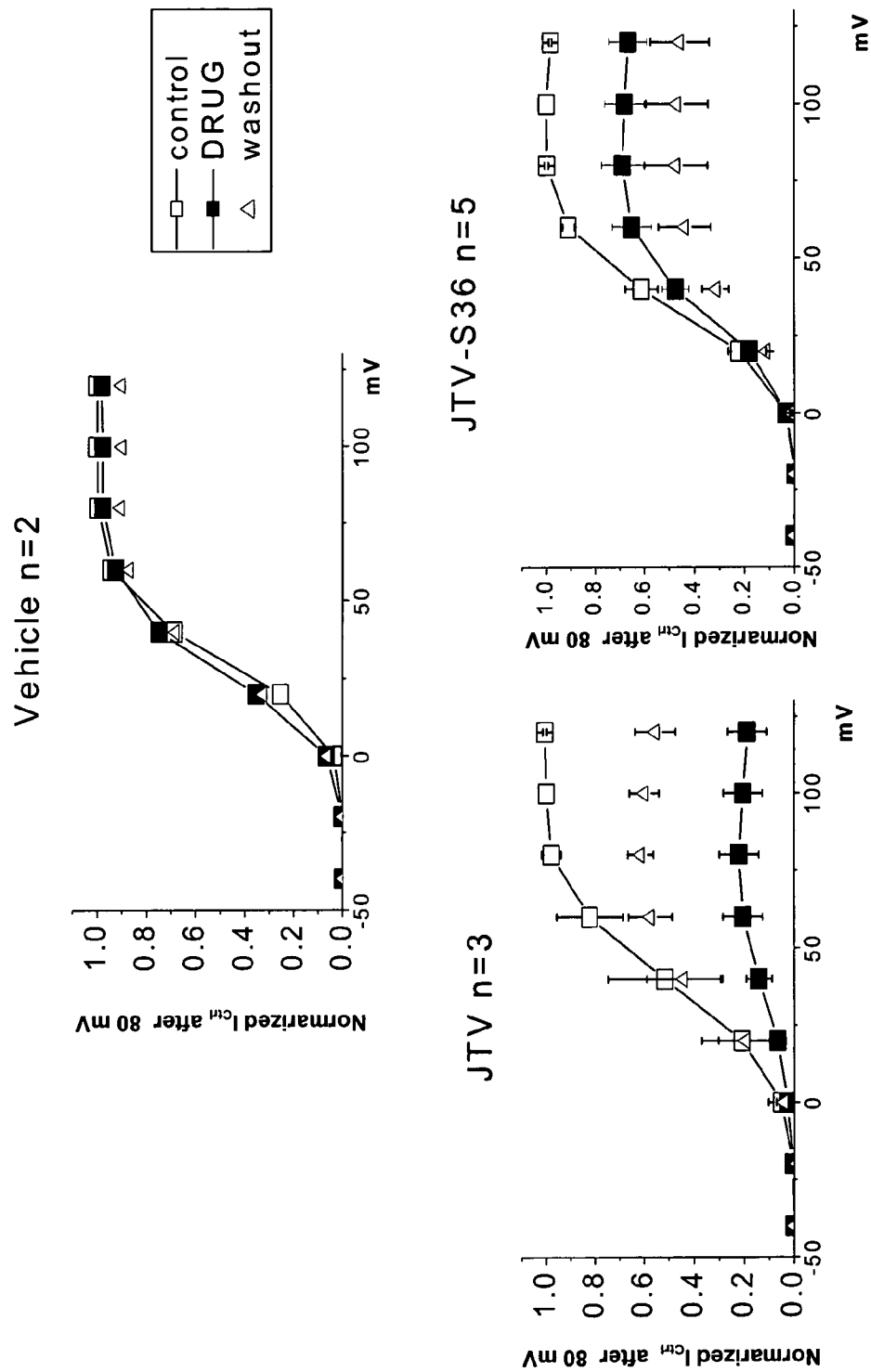

FIG. 7 demonstrates effects of JTV-519 and the inventors' novel JTV-519-related compound, S36 (disclosed herein), on activation of hERG-channel currents. The hERG-channel I-V relationships are shown for peak tail currents (activation) before (open squares) and after (closed squares) application of 0.1% DMSO (vehicle; upper panel, 1 µM JTV-519 (lower left panel), and 1 µM JTV-S36 (lower right panel). Washout of the drugs is depicted with open triangles. The voltage-clamp protocol is set forth in FIG. 4, as an I-V relationship. It should be noted that JTV-S36 did not block hERG currents at negative potentials (0 mV; 20 mV depolarization) showing voltage-dependent block of I(Kr).

Figure 8:
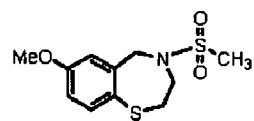
Figure 8:
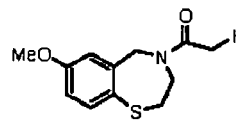
Figure 8:
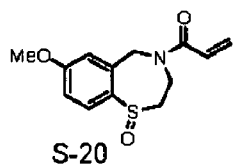
Figure 8:
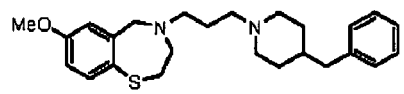
Figure 8:
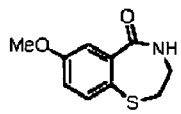
Figure 8:
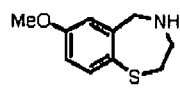
Figure 8:
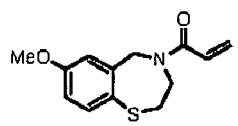
Figure 8:
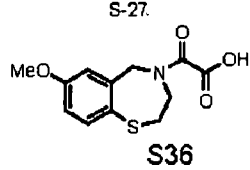

FIG. 8 shows the structures of the derivatives.

DETAILED DESCRIPTION OF THE INVENTION

As discussed above, catecholaminergic polymorphic ventricular tachycardia (CPVT) is an inherited disorder in individuals with structurally-normal hearts. It is characterized by stress-induced ventricular tachycardia, a lethal arrhythmia that may cause sudden cardiac death (SCD). Mutations in RyR2 channels, located on the sarcoplasmic reticulum (SR), have been linked to CPVT. To determine the molecular mechanism underlying the fatal cardiac arrhythmias in CPVT, the inventors studied CPVT-associated mutant RyR2 channels (e.g., S2246L, R2474S, N4104K, R4497C).

All individuals with CPVT have exercise-induced cardiac arrhythmias. The inventors previously showed that exercise-induced arrhythmias and sudden death (in patients with CPVT) result from a reduced affinity of FKBP12.6 for RyR2. Herein, the inventors have demonstrated that exercise activates RyR2 as a result of phosphorylation by adenosine 3',5'-monophosphate (cAMP)-dependent protein kinase (PKA). Mutant RyR2 channels, which had normal function in planar lipid bilayers under basal conditions, were more sensitive to activation by PKA phosphorylation—exhibiting increased activity (open probability) and prolonged open states, as compared with wild-type channels. In addition, PKA-phosphorylated mutant RyR2 channels were resistant to inhibition by $Mg^{2+}$, a physiological inhibitor of the channel, and showed reduced binding to FKBP12.6 (which stabilizes the channel in the closed state). These findings indicate that, during exercise, when the RyR2 are PKA-phosphorylated, the mutant CPVT channels are more likely to open in the relaxation phase of the cardiac cycle (diastole), increasing the likelihood of arrhythmias triggered by SR $Ca^{2+}$ leak. Since heart failure is a leading cause of death worldwide, methods to repair the leak in RyR2 could prevent fatal arrhythmias in millions of patients.

The inventors have further demonstrated herein that JTV-519, a benzothiazepine derivative, prevents lethal ventricular arrhythmias in mice heterozygous for the FKBP12.6 gene. JTV-519 reduced the open probability of RyR2, isolated from $FKBP12.6^{+/-}$ mice that died following exercise, by increasing the affinity of FKBP12.6 for PKA-phosphorylated RyR2. Moreover, JTV-519 normalized gating of CPVT-associated mutant RyR2 channels by increasing FKBP12.6 binding affinity. These data indicate that JTV-519 may prevent fatal ventricular arrhythmias by increasing FKBP12.6-RyR2 binding affinity.

Novel Methods of Treatment and Prevention

In accordance with the foregoing, the present invention provides a method for limiting or preventing a decrease in the level of RyR2-bound FKBP12.6 in cells of a subject. As used herein, "FKBP12.6" includes both an "FKBP12.6 protein" and an "FKBP12.6 analogue". Unless otherwise indicated herein, "protein" shall include a protein, protein domain, polypeptide, or peptide, and any fragment thereof. An "FKBP12.6 analogue" is a functional variant of the FKBP12.6 protein, having FKBP12.6 biological activity, that has 60% or greater amino-acid-sequence homology with the FKBP12.6 protein. As further used herein, the term "FKBP12.6 biological activity" refers to the activity of a protein or peptide that demonstrates an ability to associate physically with, or bind with, unphosphorylated or non-hyperphosphorylated RyR2 (i.e., binding of approximately two fold, or, more preferably, approximately five fold, above the background binding of a negative control), under the conditions of the assays described herein, although affinity may be different from that of FKBP12.6.

In addition, as used herein, "RyR2" includes both an "RyR2 protein" and an "RyR2 analogue". An "RyR2 analogue" is a functional variant of the RyR2 protein, having RyR2 biological activity, that has 60% or greater amino-acid-sequence homology with the RyR2 protein. As used herein, the term "RyR2 analogue" includes RyR1—the skeletal-muscle isoform of RyR2. The RyR2 of the present invention may be unphosphorylated, phosphorylated (e.g., by PKA), or hyperphosphorylated (e.g., by PKA). As further used herein, the term "RyR2 biological activity" refers to the activity of a protein or peptide that demonstrates an ability to associate physically with, or bind with, FKBP12.6 (i.e., binding of approximately two fold, or, more preferably, approximately five fold, above the background binding of a negative control), under the conditions of the assays described herein, although affinity may be different from that of RyR2.

As described above, the cardiac ryanodine receptor, RyR2, is a protein complex comprising four 565,000-dalton RyR2 proteins in association with four 12,000-dalton FKBP12.6 proteins. FK506 binding proteins (FKBPs) are cis-trans peptidyl-prolyl isomerases that are widely expressed, and serve a variety of cellular functions. FKBP12.6 protein is tightly bound to, and regulates the function of, RyR2. FKBP12.6 binds to the RyR2 channel, one molecule per RyR2 subunit, stabilizes RyR2-channel function, and facilitates coupled gating between neighboring RyR2 channels, thereby preventing aberrant activation of the channel during the resting phase of the cardiac cycle. Accordingly, as used herein, the term "RyR2-bound FKBP12.6" includes a molecule of an FKBP12.6 protein that is bound to an RyR2 protein subunit or a tetramer of FKBP12.6 that is in association with a tetramer of RyR2.

In accordance with the method of the present invention, a "decrease" in the level of RyR2-bound FKBP12.6 in cells of a subject refers to a detectable decrease, diminution, or reduction in the level of RyR2-bound FKBP12.6 in cells of the subject. Such a decrease is limited or prevented in cells of a subject when the decrease is in any way halted, hindered, impeded, obstructed, or reduced by the administration of JTV-519 (as described below), such that the level of RyR2-bound FKBP12.6 in cells of the subject is higher than it would otherwise be in the absence of JTV-519.

The level of RyR2-bound FKBP12.6 in a subject may be detected by standard assays and techniques, including those readily determined from the known art (e.g., immunological techniques, hybridization analysis, immunoprecipitation, Western-blot analysis, fluorescence imaging techniques, and/or radiation detection, etc.), as well as any assays and detection methods disclosed herein. For example, protein may be isolated and purified from cells of a subject using standard methods known in the art, including, without limitation, extraction from the cells (e.g., with a detergent that solubilizes the protein) where necessary, followed by affinity purification on a column, chromatography (e.g., FTLC and HPLC), immunoprecipitation (with an antibody), and precipitation (e.g., with isopropanol and a reagent such as Trizol). Isolation and purification of the protein may be followed by electrophoresis (e.g., on an SDS-polyacrylamide gel). A decrease in the level of RyR2-bound FKBP12.6 in a subject, or the limiting or prevention thereof, may be determined by comparing the amount of RyR2-bound FKBP12.6 detected prior to the administration of JTV-519 (in accordance with methods described below) with the amount detected a suitable time after administration of JTV-519.

In the method of the present invention, a decrease in the level of RyR2-bound FKBP12.6 in cells of a subject may be limited or prevented, for example, by inhibiting dissociation of FKBP12.6 and RyR2 in cells of the subject; by increasing binding between FKBP12.6 and RyR2 in cells of the subject; or by stabilizing the RyR2-FKBP12.6 complex in cells of a subject. As used herein, the term "inhibiting dissociation" includes blocking, decreasing, inhibiting, limiting, or preventing the physical dissociation or separation of an FKBP12.6 subunit from an RyR2 molecule in cells of the subject, and blocking, decreasing, inhibiting, limiting, or preventing the physical dissociation or separation of an RyR2 molecule from an FKBP12.6 subunit in cells of the subject. As further used herein, the term "increasing binding" includes enhancing, increasing, or improving the ability of phosphorylated RyR2 to associate physically with FKBP12.6 (e.g., binding of approximately two fold, or, more preferably, approximately five fold, above the background binding of a negative control) in cells of the subject, and enhancing, increasing, or improving the ability of FKBP12.6 to associate physically with phosphorylated RyR2 (e.g., binding of approximately two fold, or, more preferably, approximately five fold, above the background binding of a negative control) in cells of the subject. Additionally, in the method of the present invention, a decrease in the level of RyR2-bound FKBP12.6 in cells of a subject may be limited or prevented by directly decreasing the level of phosphorylated RyR2 in cells of the subject, or by indirectly decreasing the level of phosphorylated RyR2 in the cells (e.g., by targeting an enzyme (such as PKA) or another endogenous molecule that regulates or modulates the functions or levels of phosphorylated RyR2 in the cells). Preferably, the level of phosphorylated RyR2 in the cells is decreased by at least 10% in the method of the present invention. More preferably, the level of phosphorylated RyR2 is decreased by at least 20%.

In accordance with the method of the present invention, a decrease in the level of RyR2-bound FKBP12.6 is limited or prevented in a subject, particularly in cells of a subject. The subject of the present invention may be any animal, including amphibians, birds, fish, mammals, and marsupials, but is preferably a mammal (e.g., a human; a domestic animal, such as a cat, dog, monkey, mouse, or rat; or a commercial animal, such as a cow or pig). Additionally, the subject of the present invention is a candidate for exercise-induced cardiac arrhythmia. Exercise-induced cardiac arrhythmia is a heart condition (e.g., a ventricular fibrillation or ventricular tachycardia, including any that leads to sudden cardiac death) that develops during/after a subject has undergone physical exercise. A "candidate" for exercise-induced cardiac arrhythmia is a subject who is known to be, or is believed to be, or is suspected of being, at risk for developing cardiac arrhythmia during/after physical exercise. Examples of candidates for exercise-induced cardiac arrhythmia include, without limitation, an animal/person known to have catecholaminergic polymorphic ventricular tachycardia (CPVT); an animal/person suspected of having CPVT; and an animal/person who is known to be, or is believed to be, or is suspected of being, at risk for developing cardiac arrhythmia during/after physical exercise, and who is about to exercise, is currently exercising, or has just completed exercise. As discussed above, CPVT is an inherited disorder in individuals with structurally-normal hearts. It is characterized by stress-induced ventricular tachycardia—a lethal arrhythmia that may cause sudden cardiac death. In subjects with CPVT, physical exertion and/or stress induce bidirectional and/or polymorphic ventricular tachycardias that lead to sudden cardiac death (SCD) in the absence of detectable structural heart disease. Individuals with CPVT have ventricular arrhythmias when subjected to exercise, but do not develop arrhythmias at rest.

In the method of the present invention, the cells of a subject are preferably striated muscle cells. A striated muscle is a muscle in which the repeating units (sarcomeres) of the contractile myofibrils are arranged in registry throughout the cell, resulting in transverse or oblique striations that may be observed at the level of a light microscope. Examples of striated muscle cells include, without limitation, voluntary (skeletal) muscle cells and cardiac muscle cells. In a preferred embodiment, the cell used in the method of the present invention is a human cardiac muscle cell. As used herein, the term "cardiac muscle cell" includes cardiac muscle fibers, such as those found in the myocardium of the heart. Cardiac muscle fibers are composed of chains of contiguous heart-muscle cells, or cardiomyocytes, joined end to end at intercalated disks. These disks possess two kinds of cell junctions: expanded desmosomes extending along their transverse portions, and gap junctions, the largest of which lie along their longitudinal portions.

In the method of the present invention, a decrease in the level of RyR2-bound FKBP12.6 is limited or prevented in cells of a subject by administering JTV-519 to the subject; this would also permit contact between cells of the subject and JTV-519. JTV-519 (4-[3-(4-benzylpiperidin-1-yl)propionyl]-7-methoxy-2,3,4,5-tetrahydro- 1,4-benzothiazepine monohydrochloride), also known as k201, is a derivative of 1,4-benzothiazepine, and a modulator of calcium-ion channels. In addition to regulating $Ca^{2+}$ levels in myocardial cells, JTV-519 modulates the $Na^+$ current and the inward-rectifier $K^+$ current in guinea pig ventricular cells, and inhibits the delayed-rectifier K$^+$ current in guinea pig atrial cells. FK506 and rapamycin are drugs that may be used to design other compounds that stabilize RyR2-FKBP12.6 binding in cells of a subject who is a candidate for exercise-induced cardiac arrhythmia. FK506 and rapamycin both dissociate FKBP12.6 from RyR2. It is possible to design and/or screen for compounds that are structurally related to these drugs, but have the opposite effects.

In the method of the present invention, JTV-519 may be administered to a subject by way of a therapeutic composition, comprising JTV-519 and a pharmaceutically-acceptable carrier. The pharmaceutically-acceptable carrier must be "acceptable" in the sense of being compatible with the other ingredients of the composition, and not deleterious to the recipient thereof. The pharmaceutically-acceptable carrier employed herein is selected from various organic or inorganic materials that are used as materials for pharmaceutical formulations, and which may be incorporated as analgesic agents, buffers, binders, disintegrants, diluents, emulsifiers, excipients, extenders, glidants, solubilizers, stabilizers, suspending agents, tonicity agents, vehicles, and viscosity-increasing agents. If necessary, pharmaceutical additives, such as antioxidants, aromatics, colorants, flavor-improving agents, preservatives, and sweeteners, may also be added. Examples of acceptable pharmnaceutical carriers include carboxymethyl cellulose, crystalline cellulose, glycerin, gum arabic, lactose, magnesium stearate, methyl cellulose, powders, saline, sodium alginate, sucrose, starch, talc, and water, among others.

The pharmaceutical formulations of the present invention may be prepared by methods well-known in the pharmaceutical arts. For example, the JTV-519 may be brought into association with a carrier or diluent, as a suspension or solution. Optionally, one or more accessory ingredients (e.g., buffers, flavoring agents, surface active agents, and the like) also may be added. The choice of carrier will depend upon the route of administration.

JTV-519 may be administered to a subject by contacting target cells (e.g., cardiac muscle cells) in vivo in the subject with the JTV-519. JTV-519 may be contacted with (e.g., introduced into) cells of the subject using known techniques utilized for the introduction and administration of proteins, nucleic acids, and other drugs. Examples of methods for contacting the cells with (i.e., treating the cells with) JTV-519 include, without limitation, absorption, electroporation, immersion, injection, introduction, liposome delivery, transfection, transfusion, vectors, and other drug-delivery vehicles and methods. When the target cells are localized to a particular portion of a subject, it may be desirable to introduce the JTV-519 directly to the cells, by injection or by some other means (e.g., by introducing the JTV-519 into the blood or another body fluid). The target cells may be contained in heart tissue of a subject, and may be detected in heart tissue of the subject by standard detection methods readily determined from the known art, examples of which include, without limitation, immunological techniques (e.g., immunohistochemical staining), fluorescence imaging techniques, and microscopic techniques.

Additionally, the JTV-519 of the present invention may be administered to a human or animal subject by known procedures, including, without limitation, oral administration, parenteral administration, and transdermal administration. Preferably, the JTV-519 is administered parenterally, by epifascial, intracapsular, intracranial, intracutaneous, intrathecal, intramuscular, intraorbital, intraperitoneal, intraspinal, intrastemal, intravascular, intravenous, parenchymatous, subcutaneous, or sublingual injection, or by way of catheter.

In one embodiment, the agent is administered to the subject by way of targeted delivery to cardiac muscle cells via a catheter inserted into the subject's heart.

For oral administration, a JTV-519 formulation may be presented as capsules, tablets, powders, granules, or as a suspension. The formulation may have conventional additives, such as lactose, mannitol, corn starch, or potato starch. The formulation also may be presented with binders, such as crystalline cellulose, cellulose derivatives, acacia, corn starch, or gelatins. Additionally, the formulation may be presented with disintegrators, such as corn starch, potato starch, or sodium carboxymethylcellulose. The formulation also may be presented with dibasic calcium phosphate anhydrous or sodium starch glycolate. Finally, the formulation may be presented with lubricants, such as talc or magnesium stearate.

For parenteral administration (i.e., administration by injection through a route other than the alimentary canal), JTV-519 may be combined with a sterile aqueous solution that is preferably isotonic with the blood of the subject. Such a formulation may be prepared by dissolving a solid active ingredient in water containing physiologically-compatible substances, such as sodium chloride, glycine, and the like, and having a buffered pH compatible with physiological conditions, so as to produce an aqueous solution, then rendering said solution sterile. The formulation may be presented in unit or multi-dose containers, such as sealed ampoules or vials. The formulation may be delivered by any mode of injection, including, without limitation, epifascial, intracapsular, intracranial, intracutaneous, intrathecal, intramuscular, intraorbital, intraperitoneal, intraspinal, intrasternal, intravascular, intravenous, parenchymatous, subcutaneous, or sublingual, or by way of catheter into the subject's heart.

For transdermal administration, JTV-519 may be combined with skin penetration enhancers, such as propylene glycol, polyethylene glycol, isopropanol, ethanol, oleic acid, N-methylpyrrolidone, and the like, which increase the permeability of the skin to the JTV-519, and permit the JTV-519 to penetrate through the skin and into the bloodstream. The JTV-519/enhancer composition also may be further combined with a polymeric substance, such as ethylcellulose, hydroxypropyl cellulose, ethylene/vinylacetate, polyvinyl pyrrolidone, and the like, to provide the composition in gel form, which may be dissolved in a solvent, such as methylene chloride, evaporated to the desired viscosity, and then applied to backing material to provide a patch.

In accordance with the method of the present invention, JTV-519 may be administered to the subject (and JTV-519 may be contacted with cells of the subject) in an amount effective to limit or prevent a decrease in the level of RyR2-bound FKBP12.6 in the subject, particularly in cells of the subject. This amount may be readily determined by the skilled artisan, based upon known procedures, including analysis of titration curves established in vivo, and methods and assays disclosed herein. A suitable amount of JTV-519 effective to limit or prevent a decrease in the level of RyR2-bound FKBP12.6 in the subject may range from about 5 mg/kg/day to about 20 mg/kg/day, and/or may be an amount sufficient to achieve plasma levels ranging from about 300 ng/ml to about 1000 ng/ml. Preferably, the amount of JTV-519 ranges from about 10 mg/kg/day to about 20 mg/kg/day.

In one embodiment of the present invention, the subject has not yet developed exercise-induced cardiac arrhythmia. In this case, the amount of JTV-519 effective to limit or prevent a decrease in the level of RyR2-bound FKBP12.6 in the subject may be an amount of JTV-519 effective to prevent exercise-induced cardiac arrhythmia in the subject. Cardiac arrhythmia is a disturbance of the electrical activity of the heart that manifests as an abnormality in heart rate or heart rhythm. As used herein, an amount of JTV-519 "effective to prevent exercise-induced cardiac arrhythmia" includes an amount of JTV-519 effective to prevent the development of the clinical impairment or symptoms of the exercise-induced cardiac arrhythmia (e.g., palpitations, fainting, ventricular fibrillation, ventricular tachycardia, and sudden cardiac death). The amount of JTV-519 effective to prevent exercise-induced cardiac arrhythmia in a subject will vary depending upon the particular factors of each case, including the type of exercise-induced cardiac arrhythmia, the subject's weight, the severity of the subject's condition, and the mode of administration of the JTV-519. This amount may be readily determined by the skilled artisan, based upon known procedures, including clinical trials, and methods disclosed herein. In a preferred embodiment, the amount of JTV-519 effective to prevent the exercise-induced cardiac arrhythmia is an amount of JTV-519 effective to prevent exercise-induced sudden cardiac death in the subject. In another preferred embodiment, the JTV-519 prevents exercise-induced cardiac arrhythmia and exercise-induced sudden cardiac death in the subject.

Because of its ability to stabilize RyR2-bound FKBP12.6, and maintain and restore balance in the context of dynamic PKA phosphorylation and dephosphorylation of RyR2, JTV-519 may also be useful in treating a subject who has already started to experience clinical symptoms of exercise-induced cardiac arrhythmia. If the symptoms of arrhythmia are observed in the subject early enough, JTV-519 might be effective in limiting or preventing a further decrease in the level of RyR2-bound FKBP12.6 in the subject.

Accordingly, in still another embodiment of the present invention, the subject has been exercising, or is currently exercising, and has developed exercise-induced cardiac arrhythmia. In this case, the amount of JTV-519 effective to limit or prevent a decrease in the level of RyR2-bound FKBP12.6 in the subject may be an amount of JTV-519 effective to treat exercise-induced cardiac arrhythmia in the subject. As used herein, an amount of JTV-519 "effective to treat exercise-induced cardiac arrhythmia" includes an amount of JTV-519 effective to alleviate or ameliorate the clinical impairment or symptoms of the exercise-induced cardiac arrhythmia (e.g., palpitations, fainting, ventricular fibrillation, ventricular tachycardia, and sudden cardiac death). The amount of JTV-519 effective to treat exercise-induced cardiac arrhythmia in a subject will vary depending upon the particular factors of each case, including the type of exercise-induced cardiac arrhythmia, the subject's weight, the severity of the subject's condition, and the mode of administration of the JTV-519. This amount may be readily determined by the skilled artisan, based upon known procedures, including clinical trials, and methods disclosed herein. In a preferred embodiment, the JTV-519 treats exercise-induced cardiac arrhythmia in the subject.

The present invention further provides a method for treating exercise-induced cardiac arrhythmia in a subject. The method comprises administering JTV-519 to the subject in an amount effective to treat exercise-induced cardiac arrhythmia in the subject. A suitable amount of JTV-519 effective to treat exercise-induced cardiac arrhythmia in the subject may range from about 5 mg/kg/day to about 20 mg/kg/day, and/or may be an amount sufficient to achieve plasma levels ranging from about 300 ng/ml to about 1000 ng/ml. The present invention also provides a method for preventing exercise-induced cardiac arrhythmia in a subject. The method comprises administering JTV-519 to the subject in an amount effective to prevent exercise-induced cardiac arrhythmia in the subject. A suitable amount of JTV-519 effective to prevent exercise-induced cardiac arrhythmia in the subject may range from about 5 mg/kg/day to about 20 mg/kg/day, and/or may be an amount sufficient to achieve plasma levels ranging from about 300 ng/ml to about 1000 ng/ml. Additionally, the present invention provides a method for preventing exercise-induced sudden cardiac death in a subject. The method comprises administering JTV-519 to the subject in an amount effective to prevent exercise-induced sudden cardiac death in the subject. A suitable amount of JTV-519 effective to prevent exercise-induced sudden cardiac death in the subject may range from about 5 mg/kg/day to about 20 mg/kg/day, and/or may be an amount sufficient to achieve plasma levels ranging from about 300 ng/ml to about 1000 ng/ml.

In various embodiments of the above-described methods, the exercise-induced cardiac arrhythmia in the subject is associated with VT. In preferred embodiments, the VT is CPVT. In other embodiments of these methods, the subject is a candidate for exercise-induced cardiac arrhythmia, including candidates for exercise-induced sudden cardiac death.

In view of the foregoing methods, the present invention also provides use of JTV-519 in a method for limiting or preventing a decrease in the level of RyR2-bound FKBP12.6 in a subject who is a candidate for exercise-induced cardiac arrhythmia. The present invention also provides use of JTV-519 in a method for treating or preventing exercise-induced cardiac arrhythmia in a subject. Furthermore, the present invention provides use of JTV-519 in a method for preventing exercise-induced sudden cardiac death in a subject.

As discussed above and presented herein, the inventors' data show that protein kinase A (PKA) phosphorylation of the cardiac ryanodine receptor, RyR2, on serine 2809 activates the channel by releasing the FK506 binding protein, FKBP12.6. In failing hearts (including human hearts and animal models of heart failure), RyR2 is PKA-hyperphosphorylated, resulting in defective channels that have decreased amounts of bound FKBP12.6, and have increased sensitivity to calcium-induced activation. The net result of these changes is that the RyR2 channels are "leaky". These channel leaks can result in a depletion of intracellular stores of calcium to such an extent that there is no longer enough calcium in the sarcoplasmic reticulum (SR) to provide a strong stimulus for muscle contraction. This results in weak contraction of heart muscle. As a second consequence of the channel leaks, RyR2 channels release calcium during the resting phase of the heart cycle known as "diastole". This release of calcium during diastole can trigger the fatal arrhythmias of the hearts (e.g., ventricular tachycardia and ventricular fibrillation) that cause sudden cardiac death (SCD).

The inventors have also shown that treatment of heart failure with a mechanical pumping device, referred to as a left ventricular assist device (LVAD), which puts the heart at rest and restores normalized function, is associated with a reduction in the PKA hyperphosphorylation of RyR2, and normalized function of the channel. Furthermore, the inventors have shown that treatment of dogs (who have pacing-induced heart failure) with beta-adrenergic blockers (beta blockers) reverses the PKA hyperphosphorylation of RyR2. Beta blockers inhibit the pathway that activates PKA. The conclusion which may be drawn from the results of the inventors' work is that PKA phosphorylation of RyR2 increases the activity of the channel, resulting in the release of more calcium into the cell for a given trigger (activator) of the channel.

As further disclosed herein, the inventors have established that exercise-induced sudden cardiac death is associated with an increase in phosphorylation of RyR2 proteins (particularly CPVT-associated RyR2 mutant proteins) and a decrease in the level of RyR2-bound FKBP12.6. It is possible to use this mechanism to design effective drugs for preventing exercise-induced sudden cardiac death. A candidate agent having the ability to limit or prevent a decrease in the level of RyR2-bound FKBP12.6 may, as a consequence of this limiting or preventive activity, have an effect on an RyR2-associated biological event, thereby preventing exercise-induced sudden cardiac death.

Accordingly, the present invention further provides a method for identifying an agent for use in preventing exercise-induced sudden cardiac death. The method comprises the steps of: (a) obtaining or generating a culture of cells containing RyR2; (b) contacting the cells with a candidate agent; (c) exposing the cells to one or more conditions known to increase phosphorylation of RyR2 in cells; and (d) determining if the agent limits or prevents a decrease in the level of RyR2-bound FKBP12.6 in the cells. As used herein, an "agent" shall include a protein, polypeptide, peptide, nucleic acid (including DNA or RNA), antibody, Fab fragment, $F(ab')_2$ fragment, molecule, compound, antibiotic, drug, and any combination(s) thereof. An agent that limits or prevents a decrease in the level of RyR2-bound FKBP12.6 may be either natural or synthetic, and may be an agent reactive with (i.e., an agent that has affinity for, binds to, or is directed against) RyR2 and/or FKBP12.6. As further used herein, a cell "containing RyR2" is a cell (preferably, a cardiac muscle cell) in which RyR2, or a derivative or homologue thereof, is naturally expressed or naturally occurs. Conditions known to increase phosphorylation of RyR2 in cells include, without limitation, PKA.

In the method of the present invention, cells may be contacted with a candidate agent by any of the standard methods of effecting contact between drugs/agents and cells, including any modes of introduction and administration described herein. The level of RyR2-bound FKBP12.6 in the cell may be measured or detected by known procedures, including any of the methods, molecular procedures, and assays known to one of skill in the art or described herein. In one embodiment of the present invention, the agent limits or prevents a decrease in the level of RyR2-bound FKBP12.6 in the cells.

As disclosed herein, RyR2 has been implicated in a number of biological events in striated muscle cells. For example, it has been shown that RyR2 channels play an important role in EC coupling and contractility in cardiac muscle cells. Therefore, it is clear that preventive drugs designed to limit or prevent a decrease in the level of RyR2-bound FKBP12.6 in cells, particularly cardiac muscle cells, may be useful in the regulation of a number of RyR2-associated biological events, including EC coupling and contractility. Thus, once the candidate agent of the present invention has been screened, and has been determined to have a suitable limiting or preventive effect on decreasing levels of RyR2-bound FKBP12.6, it may be evaluated for its effect on EC coupling and contractility in cells, particularly cardiac muscle cells. It is expected that the preventive agent of the present invention will be useful for preventing exercise-induced sudden cardiac death.

Accordingly, the method of the present invention may further comprise the steps of: (e) contacting the candidate agent with a culture of cells containing RyR2; and (f) determining if the agent has an effect on an RyR2-associated biological event in the cells. As used herein, an "RyR2-associated biological event" includes a biochemical or physiological process in which RyR2 levels or activity have been implicated. As disclosed herein, examples of RyR2-associated biological events include, without limitation, EC coupling and contractility in cardiac muscle cells. According to this method of the present invention, a candidate agent may be contacted with one or more cells (preferably, cardiac muscle cells) in vitro. For example, a culture of the cells may be incubated with a preparation containing the candidate agent. The candidate agent's effect on an RyR2-associated biological event then may be assessed by any biological assays or methods known in the art, including immunoblotting, single-channel recordings and any others disclosed herein.

The present invention is further directed to an agent identified by the above-described identification method, as well as a pharmaceutical composition comprising the agent and a pharmaceutically-acceptable carrier. The agent may be useful for preventing exercise-induced sudden cardiac death in a subject, and for treating or preventing other RyR2-associated conditions. As used herein, an "RyR2-associated condition" is a condition, disease, or disorder in which RyR2 level or activity has been implicated, and includes an RyR2-associated biological event. The RyR2-associated condition may be treated or prevented in the subject by administering to the subject an amount of the agent effective to treat or prevent the RyR2-associated condition in the subject. This amount may be readily determined by one skilled in the art. In one embodiment, the present invention provides a method for preventing exercise-induced sudden cardiac death in a subject, by administering the agent to the subject in an amount effective to prevent the exercise-induced sudden cardiac death in the subject.

The present invention also provides an in vivo method for identifying an agent for use in preventing exercise-induced sudden cardiac death. The method comprises the steps of: (a) obtaining or generating an animal containing RyR2; (b) administering a candidate agent to the animal; (c) exposing the animal to one or more conditions known to increase phosphorylation of RyR2 in cells; and (d) determining if the agent limits or prevents a decrease in the level of RyR2-bound FKBP12.6 in the animal. The method may further comprise the steps of: (e) administering the agent to an animal containing RyR2; and (f) determining if the agent has an effect on an RyR2-associated biological event in the animal. Also provided is an agent identified by this method; a pharmaceutical composition comprising this agent; and a method for preventing exercise-induced sudden cardiac death in a subject, by administering this agent to the subject in an amount effective to prevent the exercise-induced sudden cardiac death in the subject.

The inventors' work has demonstrated that compounds which block PKA activation would be expected to reduce the activation of the RyR2 channel, resulting in less release of calcium into the cell. Compounds that bind to the RyR2 channel at the FKBP12.6 binding site, but do not come off the channel when the channel is phosphorylated by PKA, would also be expected to decrease the activity of the channel in response to PKA activation or other triggers that activate the RyR2 channel. Such compounds would also result in less calcium release into the cell. In view of these findings, the present invention further provides additional assays for identifying agents that may be useful in preventing exercise-induced sudden cardiac death, in that they block or inhibit activation of RyR2.

By way of example, the diagnostic assays of the present invention may screen for the release of calcium into cells via the RyR2 channel, using calcium-sensitive fluorescent dyes (e.g., Fluo-3, Fura-2, and the like). Cells may be loaded with the fluorescent dye of choice, then stimulated with RyR2 activators to determine whether or not compounds added to the cell reduce the calcium-dependent fluorescent signal (Brillantes et al., Stabilization of calcium release channel (ryanodine receptor) function by FK506-binding protein. *Cell*, 77:513-23, 1994; Gillo et al., Calcium entry during induced differentiation in murine erythroleukemia cells. *Blood*, 81:783-92, 1993; Jayaraman et al., Regulation of the inositol 1,4,5-trisphosphate receptor by tyrosine phosphorylation. *Science*, 272:1492-94, 1996). Calcium-dependent fluorescent signals may be monitored with a photomultiplier tube, and analyzed with appropriate software, as previously described (Brillantes et al., Stabilization of calcium release channel (ryanodine receptor) function by FK506-binding protein. *Cell*, 77:513-23, 1994; Gillo et al., Calcium entry during induced differentiation in murine erythroleukemia cells. *Blood*, 81:783-92, 1993; Jayaraman et al., Regulation of the inositol 1,4,5-trisphosphate receptor by tyrosine phosphorylation. *Science*, 272:1492-94, 1996). This assay can easily be automated to screen large numbers of compounds using multiwell dishes.

To identify compounds that inhibit the PKA-dependent activation of RyR2-mediated intracellular calcium release, an assay may involve the expression of recombinant RyR2 channels in a heterologous expression system, such as Sf9, HEK293, or CHO cells (Brillantes et al., Stabilization of calcium release channel (ryanodine receptor) function by FK506-binding protein. *Cell*, 77:513-23, 1994). RyR2 could also be co-expressed with beta-adrenergic receptors. This would permit assessment of the effect of compounds on RyR2 activation, in response to addition of beta-adrenergic receptor agonists.

The level of PKA phosphorylation of RyR2 which correlates with the degree of heart failure may also be assayed, and then used to determine the efficacy of compounds designed to block the PKA phosphorylation of the RyR2 channel. Such an assay may be based on the use of antibodies that are specific for the RyR2 protein. For example, the RyR2-channel protein may be immunoprecipitated, and then back-phosphorylated with PKA and [gamma$^{32}$P]-ATP. The amount of radioactive [$^{32}$P] label that is transferred to the RyR2 protein may be then measured using a phosphorimager (Marx et al., PKA phosphorylation dissociates FKBP12.6 from the calcium release channel (ryanodine receptor): defective regulation in failing hearts. *Cell*, 101:365-76, 2000).

Another assay of the present invention involves use of a phosphoepitope-specific antibody that detects RyR2 that is PKA phosphorylated on Ser 2809. Immunoblotting with such an antibody can be used to assess efficacy of therapy for heart failure and cardiac arrhythmias. Additionally, RyR2 S2809A and RyR2 S2809D knock-in mice may be used to assess efficacy of therapy for heart failure and cardiac arrhythmias. Such mice further provide evidence that PKA hyperphosphorylation of RyR2 is a contributing factor in heart failure and cardiac arrhythmias, by showing that the RyR2 S2809A mutation inhibits heart failure and arrhythmias, and that the RyR2 S2809D mutation worsens heart failure and arrhythmias.

Novel Compounds Methods of Synthesizing Same and Uses of Same 1,4-benzothiazepine derivatives, particularly 2,3,4,5-tetrahydro-1,4-benzothiazepine derivatives, are important building blocks in the preparation of biologically-active molecules, including JTV-519. The inventors have developed a novel process for preparing 1,4-benzothiazepine intermediate compounds, such as 7-methoxy-2,3,4,5-tetrahydro-1,4-benzothiazepine. The inventors' process utilizes readily-available and inexpensive starting materials, and provides high yields of key 1,4-benzothiazepine intermediates.

In the early 1990s, Kaneko et al. (U.S. Pat. No. 5,416,066; WO 92/12148; JP4230681) disclosed that JTV-519 could be prepared by reacting 7-methoxy-2,3,4,5-tetrahydro-1,4-benzothiazepine (a 1,4-benzothiazepine intermediate) with acryloyl chloride, and then reacting the resulting product with 4-benzyl piperidine.

Two processes for the preparation of 7-methoxy-2,3,4,5-tetrahydro-1,4-benzothiazepine and similar compounds have been previously reported in the literature. The first process, disclosed by Kaneko et al. (U.S. Pat. No. 5,416,066), involved a synthetic route of six steps that started with 2,5-dihydroxybenzoic acid. In this process, 2,5-dihydroxybenzoic acid was selectively methylated with dimethyl sulfate. The resulting compound was then reacted with dimethylthiocarbamoyl chloride for 20 h, and then subjected to high temperature (270° C.) for 9 h. The product of this step was refluxed with sodium methoxide in methanol for 20 h. The product of the reflux step was then reacted with 2-chloroethylamine, under basic conditions and at a high temperature, to produce a cyclized amide. The cyclized amide was reduced with LiAlH$_4$ to yield 7-methoxy-2,3,4,5-tetrahydro-1,4-benzothiazepine (a 1,4-benzothiazepine intermediate).

The second process for the preparation of 7-methoxy-2,3,4,5-tetrahydro-1,4-benzothiazepine was disclosed by Hitoshi in a Japanese patent (JP 10045706). This process started with 2-bromo-5-methoxy benzaldehyde. The bromide was substituted with NaSMe, and the resulting product was oxidized with chlorine, followed by reflux in water, to yield disulfide dialdehyde. The dialdehyde was treated with 2-chloroethylamine, and the resulting product was reduced with a reducing agent, such as NaBH$_4$. The resulting compound was cyclized to give 7-methoxy-2,3,4,5-tetrahydro-1,4-benzothiazepine.

Initially, the inventors attempted to prepare the 1,4-benzothiazepine intermediate, 7-methoxy-2,3,4,5-tetrahydro-1,4-benzothiazepine, using the methods described above. However, they found that the first process, described by Kaneko et al. (U.S. Pat. No. 5,416,066), involved synthetic steps of high temperature and long reaction time. Additionally, the inventors discovered that the thio group in the third thiolated intermediate was easily oxidized by air to a disulfide compound, making it impossible to synthesize the subsequent cyclized product. The inventors also determined that the process described by Hitoshi (JP 10045706) involved Cl$_2$, and that another patented method for the preparation of the first intermediate, apart from the substitution of bromide with NaSMe, had to be used.

To overcome the foregoing problems, the inventors developed a novel process for making 7-methoxy-2,3,4,5-tetrahydro-1,4-benzothiazepine from readily-available and inexpensive starting materials. The inventors' process simplifies isolation and purification steps, and can be used to prepare various 1,4-benzothiazepine intermediates, including 7-methoxy-2,3,4,5-tetrahydro-1,4-benzothiazepine and other compounds having the general structure shown in formula:

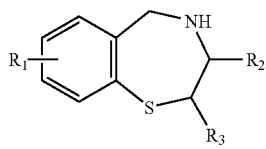

R1 = n-MeO, n-MeS, n-alkyl, n = 6,7,8,9
R2 = alkyl
R3 = alkyl

This process may also be used to prepare JTV-519.

Accordingly, in view of the foregoing, the present invention provides a method for the synthesis of a compound having formula:

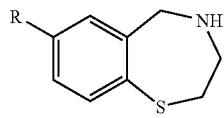

wherein R=OR', SR', NR', alkyl, or halide and R'=alkyl, aryl, or H, and wherein R can be at position 2, 3, 4, or 5, said method comprising the steps of:
(a) treating a compound having formula:

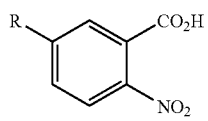

wherein R is as defined above, with a reducing agent, in the presence of an optional catalyst, to form a compound having formula:

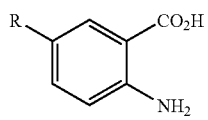

wherein R is as defined above;
(b) treating the compound formed in step (a) with a diazotizing agent and a disulfide, to form a compound having formula:

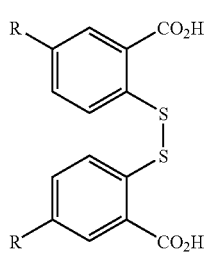

wherein R is as defined above;
(c) treating the compound formed in step (b) with an activating agent and chloroethylamine, to form a compound having formula:

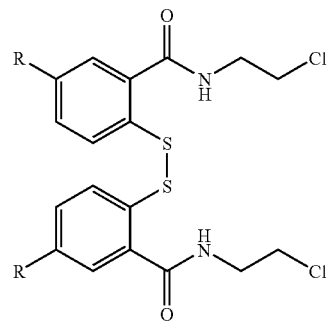

wherein R is as defined above;
(d) treating the compound formed in step (c) with a reducing agent and a base, to form a compound having formula:

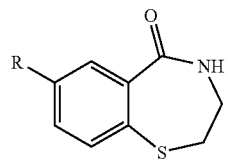

wherein R is as defined above; and
(e) treating the compound formed in step (d) with a reducing agent, to form a compound having formula:

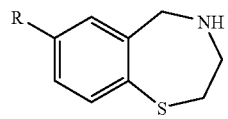

wherein R is as defined above.

In accordance with the method of the present invention, the reducing agent in step (a) may be $H_2$. Additionally, the diazotizing agent in step (b) may be $NaNO_2$, and the disulfide in step (b) may be $Na_2S_2$. Furthermore, the chloride in step (c) may be $SOCl_2$. The reducing agent in step (d) may be trimethylphosphine ($PMe_3$), while the base in step (d) is triethyl amine. In another embodiment, the reducing agent in step (e) is $LiAlH_4$.

The present invention further provides a method for the synthesis of a compound of having formula:

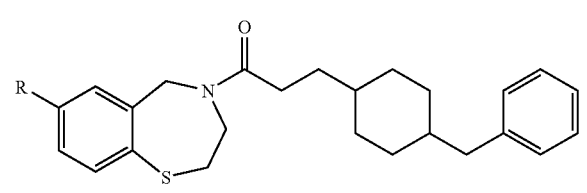

wherein R=OR', SR', NR', alkyl, or halide and R'=alkyl, aryl, or H, and wherein R can be at position 2, 3, 4, or 5, said method comprising the step of:

(a) treating a compound having formula:

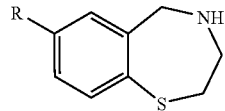

wherein R is as defined above, with 3-bromopropionic chloride and a compound having formula:

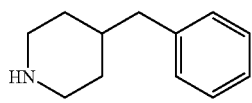

to form a compound having formula:

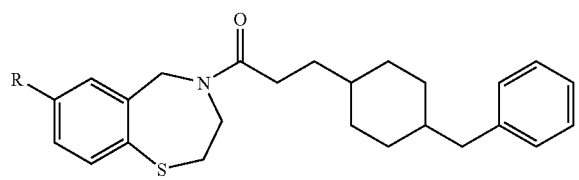

wherein R is as defined above.

By way of example, a compound having the formula:

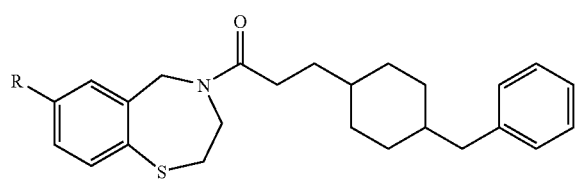

wherein R=OR', SR', NR', alkyl, or halide and R'=alkyl, aryl, or H, and wherein R can be at position 2, 3, 4, or 5, may be synthesized as follows:

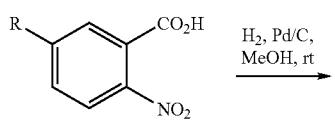

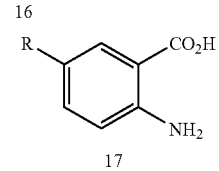

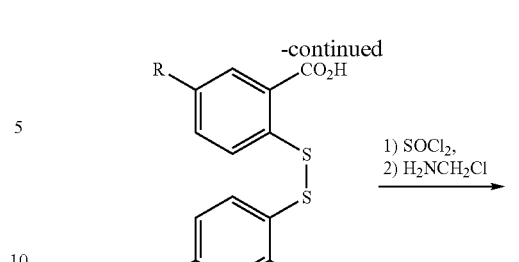

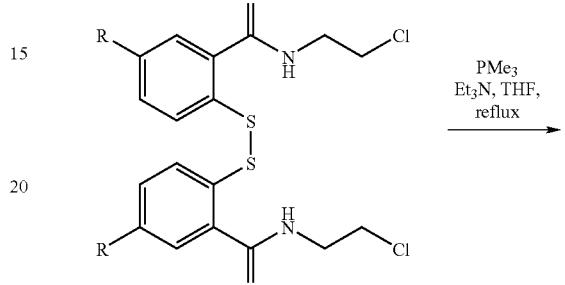

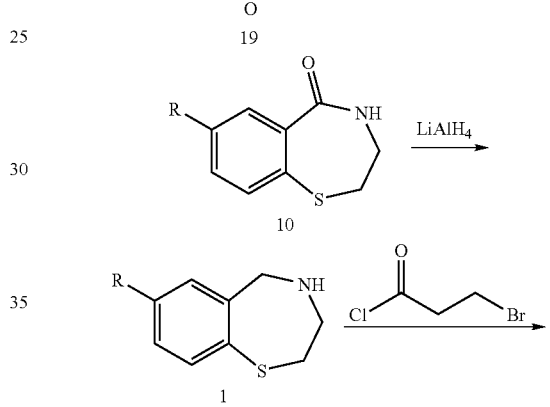

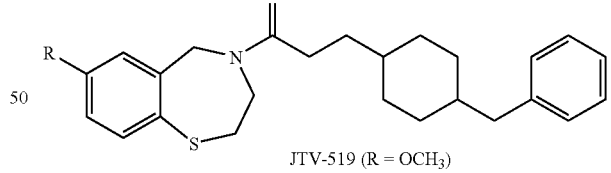

JTV-519 (R = OCH$_3$)

R = OR', SR', NR', alkyl, halides; R' = alkyl, H
R can be at positions 2, 3, 4, or 5

By way of example, and as shown in Example 7 and Scheme 1 below, 7-methoxy-2,3,4,5-tetrahydro-1,4-benzothiazepine may be prepared from 2-nitro-5-methoxybenzoic acid as follows. The nitro group of 2-nitro-5-methoxybenzoic acid is reduced, using H$_2$ with Pd/C as a catalyst, to give 2-amino-5-methoxybenzoic acid. 2-amino-5-methoxybenzoic acid may be diazotized with NaNO$_2$, and then treated with Na$_2$S$_2$, to provide a stable disulfide compound. Without further purification, the stable disulfide compound may be treated with SOCl$_2$, and then reacted with 2-chloroethylamine, in the presence of Et$_3$N, to give an amide. The amide compound may then be converted to a cyclized compound via a one-pot procedure, as follows. A reducing reagent (such as trimethylphosphine or triphenylphosphine) and a base (such as triethylamine) may be added to a solution of the amide compound in THF (tetrahydrofuran). The resulting reaction mixture may then be refluxed for 3 h. The reducing agent (trimethylphosphine or triphenylphine) cleaves the disulfide (S—S) to its monosulfide (—S), which, in situ, undergoes intramolecular cyclization with the chloride to yield a cyclized amide. The cyclized amide may then be reduced with LiAlH4 to yield the 1,4-benzothiazepine intermediate, 7-methoxy-2,3,4,5-tetrahydro-1,4-benzothiazepine.

JTV-519 may then be prepared from 7-methoxy-2,3,4,5-tetrahydro-1,4-benzothiazepine by reacting the 7-methoxy-2,3,4,5-tetrahydro-1,4-benzothiazepine with 3-bromopropionic chloride, and then reacting the resulting compound with 4-benzyl piperidine.

The present invention further provides a composition, comprising radio-labeled JTV-519. Labeling of JTV-519 may be accomplished using one of a variety of different radioactive labels known in the art. The radioactive label of the present invention may be, for example, a radioisotope. The radioisotope may be any isotope that emits detectable radiation, including, without limitation, $^{35}S$, $^{125}I$, $^{3}H$, or $^{14}C$. Radioactivity emitted by the radioisotope can be detected by techniques well known in the art. For example, gamma emission from the radioisotope may be detected using gamma imaging techniques, particularly scintigraphic imaging.

By way of example, and as shown in Example 8 and Scheme 2 below, radio-labeled JTV-519 may be prepared as follows. JTV-519 may be demethylated at the phenyl ring using BBr3. The resulting phenol compound may then be re-methylated with a radio-labeled methylating agent (such as $^{3}H$-dimethyl sulfate) in the presence of a base (such as NaH) to provide $^{3}H$-labeled JTV-519.

The present invention further provides novel 1,4-benzothiazepine intermediates and derivatives, including 2,3,4,5-tetrahydro-1,4-benzothiazepenes that are similar to JTV-519. By way of example, the present invention provides compounds having the following formulas:

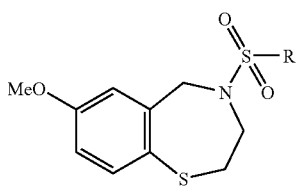

wherein R=aryl, alkenyl, alkyl, —(CH$_2$)$_n$NR'$_2$, or —(CH$_2$)$_n$SR', and n=0, 1, 2, or 3, and R'=alkyl or cycloalkyl;

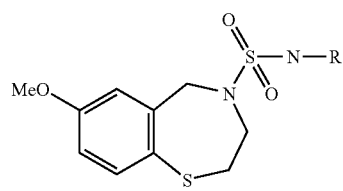

wherein R=aryl, alkyl, —(CH$_2$)$_n$NR'$_2$, or —(CH$_2$)$_n$SR', and n=0, 1, 2, or 3, and R'=alkyl or cycloalkyl;

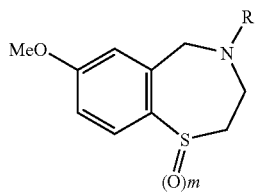

wherein R=CO(CH$_2$)$_n$XR'$_2$, SO$_2$(CH$_2$)$_n$XR'$_2$, or SO$_2$NH(CH$_2$)$_n$XR'$_2$, and X=N or S, and n=1, 2, or 3, and R'=alkyl or cycloalkyl; and wherein m=1 or 2; and

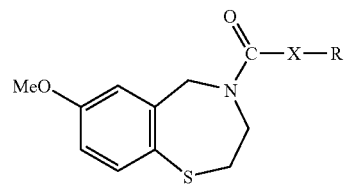

wherein R=aryl, alkyl, —(CH$_2$)$_n$NR'$_2$, —(CH$_2$)$_n$SR', and n=0, 1, 2, or 3, and R'=alkyl or cycloalkyl; and wherein X=NH or O. Also provided are additional 2,3,4,5-tetrahydro-1,4-benzothiazepine compounds having formula:

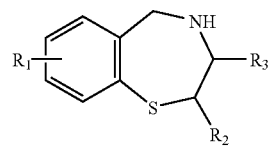

wherein R$_1$=OR', SR', NR', alkyl, or halide, at position 2, 3, 4, or 5 on the phenyl ring, and R'=alkyl, aryl, or H; wherein R$_2$=H, alkyl, or aryl; and wherein R$_3$=H, alkyl, or aryl.

Examples of the inventors' novel 1,4-benzothiazepine compounds include, without limitation, S7, S-20, S-25, S-27, and S36. Preferably, the compound is S36. Structures for S7, S-20, S-25, S-27, and S36 may be found in FIG. 8. These and any other novel compounds of the present invention may be associated with a pharmaceutically-acceptable carrier, as described above, so as to form a pharmaceutical composition.

The inventors' novel 1,4-benzothiazepine compounds share functional characteristics with JTV-519. For example, like JTV-519 (mwt=423), compound S36 (mwt=267) regulates calcium channels. Indeed, S36 (a carboxylic acid) is approximately 10 times more potent than JTV-519 in regulating calcium channels (data not shown). Unlike JTV-519, however, the inventors' novel compounds show weak blocking activity of hERGs.

The rapid delayed rectifier (I(Kr)) channel—a potassium channel—is important for repolarization of the cardiac action potential. hERG is the pore-forming subunit of the I(Kr) channel. Suppression of I(Kr) function—as a result of adverse drug effects and/or genetic defects in hERG—can lead to long-QT (LQT) syndrome, which carries increased risk of life-threatening arrhythmias. hERGs, then, are potassium-channel subunits that, when blocked, can cause cardiac arrhythmias and sudden cardiac death.

The inventors' compounds have significantly reduced blocking of hERG (I(Kr)) channels, when compared with JTV-519. As shown in FIGS. 4-7, for example, one of the inventors' compounds, S36, has hERG blocking activity that is approximately 5- to 10-fold lower than the hERG blocking activity of JTV-519. Because the inventors' compounds have weak hERG blocking activity, they are expected to be less toxic than JTV-519.

Based upon the foregoing, the inventors' novel compounds are more potent than JTV-519, and have reduced toxicity. Accordingly, it is believed that the inventors' novel compounds will be particularly useful in any of the above-described methods for limiting or preventing a decrease in the level of RyR2-bound FKBP12.6 in a subject, including a subject who is a candidate for heart failure, atrial fibrillation, or exercise-induced cardiac arrhythmia. It is also believed that the inventors' novel compounds will be particularly useful in methods for treating or preventing heart failure, atrial fibrillation, and exercise-induced cardiac arrhythmia in a subject, and in methods for preventing exercise-induced sudden cardiac death in a subject.

Accordingly, the present invention provides a method for limiting or preventing a decrease in the level of RyR2-bound FKBP12.6 in a subject, comprising administering to the subject an amount of agent effective to limit or prevent a decrease in the level of RyR2-bound FKBP12.6 in the subject, wherein the agent is selected from the group consisting of:

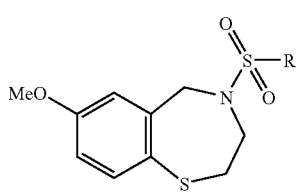
(a)

wherein R=aryl, alkenyl, alkyl, —(CH$_2$)$_n$NR'$_2$, or —(CH$_2$)$_n$SR', and n=0, 1, 2, or 3, and R'=alkyl or cycloalkyl;

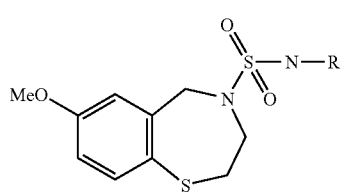
(b)

wherein R=aryl, alkyl, —(CH$_2$)$_n$NR'$_2$, or —(CH$_2$)$_n$SR', and n=0, 1, 2, or 3, and R'=alkyl or cycloalkyl;

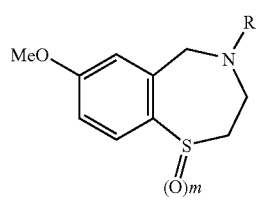
(c)

wherein R=CO(CH$_2$)$_n$XR'$_2$, SO$_2$(CH$_2$)$_n$XR'$_2$, or SO$_2$NH (CH$_2$)$_n$XR'$_2$, and X=N or S, and n=1, 2, or 3, and R'=alkyl or cycloalkyl; and wherein m=1 or 2;

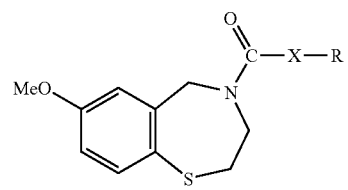
(d)

wherein R=aryl, alkyl, —(CH$_2$)$_n$NR'$_2$, —(CH$_2$)$_n$SR', and n=0, 1, 2, or 3, and R'=alkyl or cycloalkyl; and wherein X=NH or O; and

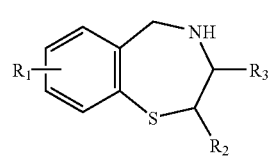
(e)

wherein $R_1$=OR', SR', NR', alkyl, or halide, at position 2, 3, 4, or 5 on the phenyl ring, and R'=alkyl, aryl, or H; wherein $R_2$=H, alkyl, or aryl; and wherein $R_3$=H, alkyl, or aryl. As described above, the subject may be any animal, but is preferably a human. In one embodiment, the subject has catecholaminergic polymorphic ventricular tachycardia (CPVT). In another embodiment, the subject is a candidate for heart failure, atrial fibrillation, or exercise-induced cardiac arrhythmia. In still another embodiment, the agent is selected from the group consisting of S4, S7, S-20, S-24, S-25, S-26, S-27, and S36. Structures for these agents may be found in FIG. 8.

In accordance with the method of the present invention, the decrease in the level of RyR2-bound FKBP12.6 may be limited or prevented in the subject by decreasing the level of phosphorylated RyR2 in the subject. In one embodiment, the amount of the agent effective to limit or prevent a decrease in the level of RyR2-bound FKBP12.6 in the subject is an amount of the agent effective to treat or prevent heart failure, atrial fibrillation, and/or exercise-induced cardiac arrhythmia in the subject. In another embodiment, the amount of the agent effective to limit or prevent a decrease in the level of RyR2-bound FKBP12.6 in the subject is an amount of the agent effective to prevent exercise-induced sudden cardiac death in the subject.

In view of the foregoing, the present invention further provides a method for treating or preventing exercise-induced cardiac arrhythmia in a subject, comprising administering to the subject a novel 1,4-benzothiazepine compound, as disclosed herein, in an amount effective to treat or prevent exercise-induced cardiac arrhythmia in the subject. Similarly, the present invention provides a method for preventing exercise-induced sudden cardiac death in a subject, comprising administering to the subject a novel 1,4-benzothiazepine compound, as disclosed herein, in an amount effective to prevent exercise-induced sudden cardiac death in the subject. Additionally, the present invention provides a method for treating or preventing atrial fibrillation or heart failure in a subject, comprising administering to the subject a novel 1,4-benzothiazepine compound, as disclosed herein, in an amount effective to treat or prevent the atrial fibrillation or heart failure in the subject. In each of these methods, the novel 1,4-benzothiazepine compound may be selected from the group consisting of:

(a)
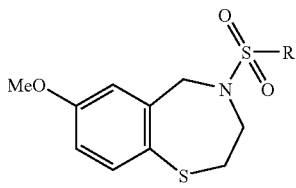

wherein R=aryl, alkenyl, alkyl, —(CH$_2$)$_n$NR'$_2$, or —(CH$_2$)$_n$SR', and n=0, 1, 2, or 3, and R'=alkyl or cycloalkyl;

(b)
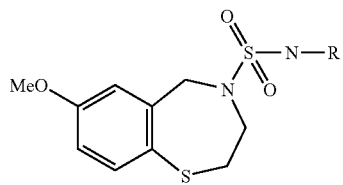

wherein R=aryl, alkyl, —(CH$_2$)$_n$NR'$_2$, or —(CH$_2$)$_n$SR', and n=0, 1, 2, or 3, and R'=alkyl or cycloalkyl;

(c)
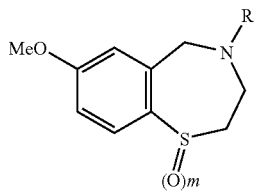

wherein R=CO(CH$_2$)$_n$XR'$_2$, SO$_2$(CH$_2$)$_n$XR'$_2$, or SO$_2$NH(CH$_2$)$_n$XR'$_2$, and X=N or S, and n=1, 2, or 3, and R'=alkyl or cycloalkyl; and wherein m=1 or 2;

(d)
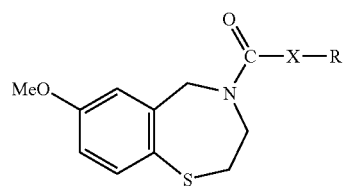

wherein R=aryl, alkyl, —(CH$_2$)$_n$NR'$_2$, —(CH$_2$)$_n$SR', and n=0, 1, 2, or 3, and R'=alkyl or cycloalkyl; and wherein X=NH or O; and (e)
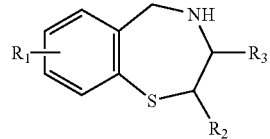

wherein R$_1$=OR', SR', NR', alkyl, or halide, at position 2, 3, 4, or 5 on the phenyl ring, and R'=alkyl, aryl, or H; wherein R$_2$=H, alkyl, or aryl; and wherein R$_3$=H, alkyl, or aryl.

The present invention further provides methods of synthesizing the novel 1,4-benzothiazepine compounds disclosed herein. For example, the present invention provides a method for the synthesis of a compound having formula:

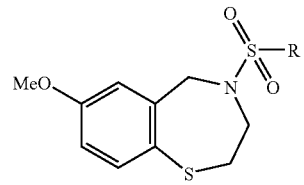

wherein R=aryl, alkenyl, alkyl, —(CH$_2$)$_n$NR'$_2$, or —(CH$_2$)$_n$SR', and n=0, 1, 2, or 3, and R'=alkyl or cycloalkyl, comprising the steps of:

(a) treating a compound having formula:

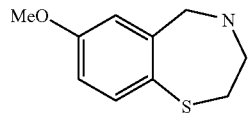

with a sulfonyl chloride compound (including any sulfonyl chloride derivative) and a base, to form a compound having the formula:

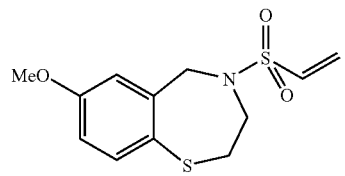

(b) optionally, treating the compound formed in step (a) with a primary or secondary amine, to form a compound having formula:

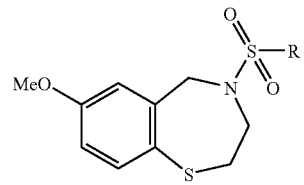

wherein R is as defined above. In one embodiment, the sulfonyl chloride compound in step (a) is selected from the group consisting of alkylsulfonyl chloride and arylsulfonyl chloride. In another embodiment, the base in step (a) is Et$_3$N. In still another embodiment, the primary or secondary amine in step (b) is 4-benzylpiperidine.

The method of the invention may further comprise the step of oxidizing the compound having formula:

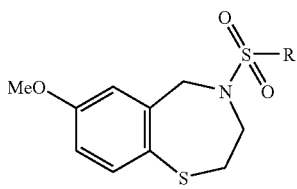

wherein R=aryl, alkenyl, alkyl, —(CH$_2$)$_n$NR'$_2$, or —(CH$_2$)$_n$SR', and n=0, 1, 2, or 3, and R'=alkyl or cycloalkyl, with an oxidizing agent, to form a compound having formula:

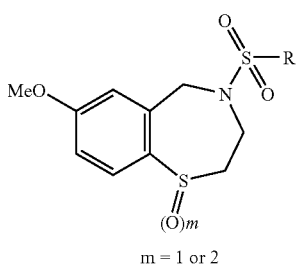

m = 1 or 2 wherein R is as defined above, and wherein m=1 or 2. In one embodiment of the present invention, the oxidizing agent is hydrogen peroxide.

By way of example, and as shown in Example 9 and Scheme 3, the inventors have developed a method of synthesizing compounds having the general structure:

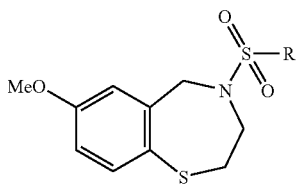

wherein R=aryl, alkenyl, alkyl, —(CH$_2$)$_n$NR'$_2$, or —(CH$_2$)$_n$SR', and n=0, 1, 2, or 3, and R'=alkyl or cycloalkyl. Novel compounds of this general structure may be prepared by reacting 7-methoxy-2,3,4,5-tetrahydro-1,4-benzothiazepine with alkylsulfonyl chloride or arylsulfonyl chloride, in the presence of a base such as Et$_3$N. Additional reactions (e.g., addition of 4-benzyl piperidine) may follow, to extend the side chain as desired. As Scheme 3 demonstrates, 2-chloroethanesulfonyl chloride (e.g., 180 mg; 1.1 mM) and Et$_3$N (e.g., 140 mg; 1.1 mM) may be added to 7-methoxy-2,3,4,5-tetrahydro-1,4-benzothiazepine (1)(e.g., 194 mg; 1 mM) in CH$_2$Cl$_2$ (e.g., 20 ml), at 0° C. The mixture may then be stirred (e.g., at 0° C. for 2 h), and washed (e.g., with H$_2$O and saturated NaHCO$_3$ solution). Removal of the solvent will yield a crude product, which may be purified by chromatography on silica gel. The structure may be confirmed by NMR. Scheme 3 further shows that the resulting compound's side chain may be extended by reacting the compound (e.g., 28 mg; 0.1 mM) with 4-benzyl piperidine (e.g., 21 mg; 0.13 mM) in CH$_2$Cl$_2$. After the reaction goes to completion, the excess amine may be removed by a base scavenger (e.g., 3-(2-succinic anhydride)propylfunctionalized silica gel, 0.5 g).

The present invention also provides a method for the synthesis of a compound of having formula:

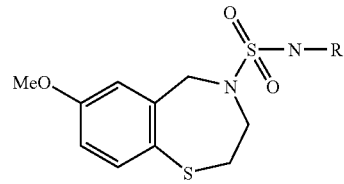

wherein R=aryl, alkyl, —(CH$_2$)$_n$NR'$_2$, or —(CH$_2$)$_n$SR', and n=0, 1, 2, or 3, and R'=alkyl or cycloalkyl, comprising the step of treating a compound having formula:

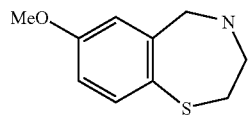

with a sulfuryl chloride and a primary or secondary amine, in the presence of a base, to form a compound having the formula:

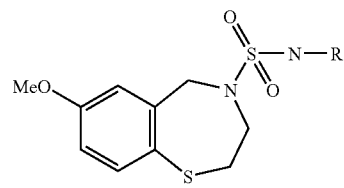

wherein R is as defined above. In one embodiment of the present invention, the base is Et$_3$N. In another embodiment, the primary or secondary amine is 1-piperonylpiperazine.

The method of the present invention may further comprise the step of oxidizing the compound having formula:

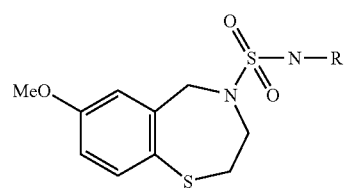

wherein R=aryl, alkyl, —(CH$_2$)$_n$NR'$_2$, or —(CH$_2$)$_n$SR', and n=0, 1, 2, or 3, and R'=alkyl or cycloalkyl, to form a compound having formula:

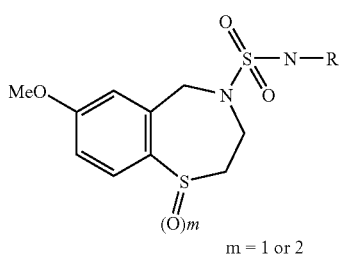

m = 1 or 2 wherein R is as defined above, and wherein m=1 or 2. In one embodiment, the oxidizing agent is hydrogen peroxide.

By way of example, and as shown in Example 9 and Scheme 4, the inventors have developed a method of synthesizing compounds having the general structure:

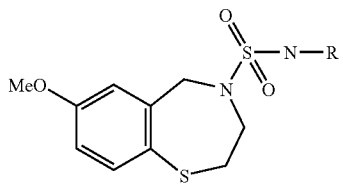

wherein R=aryl, alkyl, —$(CH_2)_nNR'_2$, or —$(CH_2)_nSR'$, and n=0, 1, 2, or 3, and R'=alkyl or cycloalkyl. Novel compounds of this general structure may be prepared by a one-pot reaction of 7-methoxy-2,3,4,5-tetrahydro-1,4-benzothiazepine with sulfuryl chloride, in the presence of a base (e.g., $Et_3N$), followed by a primary or secondary amine. As Scheme 4 demonstrates, sulfuryl chloride (e.g., 15.0 mg; 0.111 mM) and $Et_3N$ (e.g., 28.0 mg; 0.22 mM) may be added to 7-methoxy-2,3,4,5-tetrahydro-1,4-benzothiazepine (e.g., 19.4 mg; 0.1 mM) in $CH_2Cl_2$ (e.g., 20 ml), at 0° C. After stirring the mixture (e.g., for 2 h at 0° C.), 1-piperonylpiperazine (e.g., 27 mg; 0.12 mM) may be added. The mixture may be stirred for another 2 h, and then washed (e.g., with $H_2O$ and a saturated $NaHCO_3$ solution). The excess amine may be removed by addition of a base scavenger (e.g., 3-(2-succinic anhydride) propylfunctionalized silica gel, 0.2 g).

The present invention further provides a method for the synthesis of a compound of having formula:

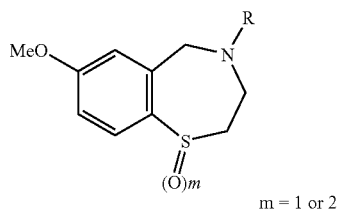

m = 1 or 2 wherein R=$CO(CH_2)_nXR'_2$, $SO_2(CH_2)_nXR'_2$, or $SO_2NH(CH_2)_nXR'_2$, and X=N or S, and n=1, 2, or 3, and R'=alkyl or cycloalkyl; and wherein m=1 or 2, comprising the step of treating a compound having formula:

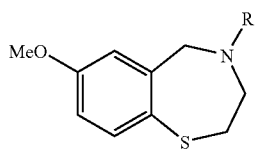

wherein R is as defined above, with an oxidizing agent, to form a compound having formula:

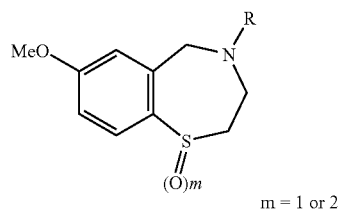

m = 1 or 2 wherein R and m are as defined above. In one embodiment, the oxidizing agent is hydrogen peroxide. This method may also be used to oxidize JTV-519.

The present invention further provides a method for the synthesis of a compound of having formula:

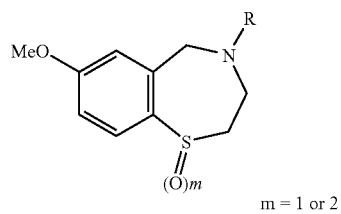

m = 1 or 2 wherein R=$CO(CH_2)_nXR'_2$, $SO_2(CH_2)_nXR'_2$, or $SO_2NH(CH_2)_nXR'_2$, and X=N or S, and n=1, 2, or 3, and R'=alkyl or cycloalkyl; and wherein m=1 or 2, comprising the step of treating a compound having formula:

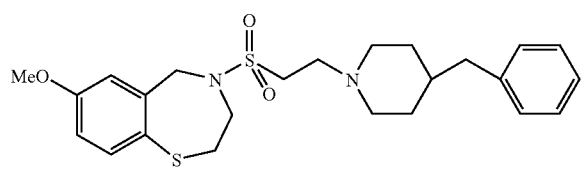

with an oxidizing agent, to form a compound having formula:

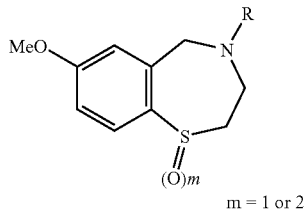

m = 1 or 2 wherein R and m are as defined above. In one embodiment, the oxidizing agent is hydrogen peroxide. This method may also be used to oxidize JTV-519.

By way of example, and as shown in Example 9 and Scheme 5, the inventors have developed a method of synthesizing compounds having the general structure:

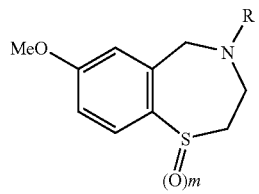

wherein R=CO(CH$_2$)$_n$XR'$_2$, SO$_2$(CH$_2$)$_n$XR'$_2$, or SO$_2$NH(CH$_2$)$_n$XR'$_2$, and X=N or S, and n=1, 2, or 3, and R'=alkyl or cycloalkyl; and wherein m=1 or 2. Novel compounds of this general structure may be prepared by oxidation of JTV-5 19, or one of the novel 1,4-benzothiazepine derivatives disclosed herein, with hydrogen peroxide. As Scheme 5 shows, the 1,4-benzothiazepine compound of interest (e.g., 21 mg; 0.05 mM) in MeOH (e.g., 5 ml) may be added to H$_2$O$_2$ (e.g., 0.1 ml, excess). The mixture may be stirred (e.g., for 2 days), and the resulting product may be purified by chromatography on silica gel (e.g., CH$_2$Cl$_2$:MeOH=10:1)

Additionally, the present invention provides a method for the synthesis of a compound having formula:

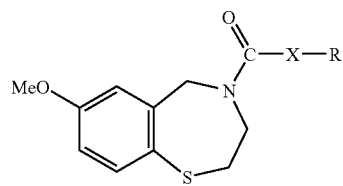

wherein R=aryl, alkyl, —(CH$_2$)$_n$NR'$_2$, or —(CH$_2$)$_n$SR', and n=0, 1, 2, or 3, and R'=alkyl or cycloalkyl; and wherein X=NH or O, comprising the step of treating a compound having formula:

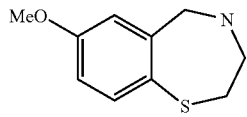

with a carbonyl chloride compound, in the presence of a base, and with a primary or secondary amine or an alcohol, to form a compound having the formula:

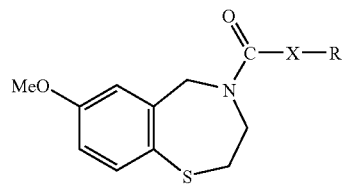

wherein R and X are as defined above. In one embodiment, the carbonyl chloride compound is triphosgene. In another embodiment, the base is Et$_3$N. In yet another embodiment, the primary or secondary amine is 4-benzylpiperidine.

By way of example, and as shown in Example 9 and Scheme 6, the inventors have developed a method of synthesizing compounds having the general structure:

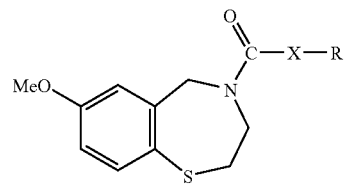

wherein R=aryl, alkyl, —(CH$_2$)$_n$NR'$_2$, —(CH$_2$)$_n$SR', and n=0, 1, 2, or 3, and R'=alkyl or cycloalkyl; and wherein X=NH or O. Novel compounds of this general structure may be prepared by reacting 7-methoxy-2,3,4,5-tetrahydro-1,4-benzothiazepine with triphosgene, in the presence of a base (e.g., Et$_3$N), followed by addition of a primary or secondary amine or an alcohol.

The present invention further provides a method for the synthesis of 2,3,4,5-tetrahydro-1,4-benzothiazepine compounds having formula:

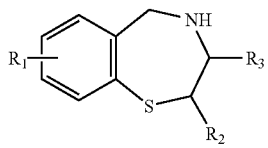

wherein R$_1$=OR', SR', NR', alkyl, or halide, at position 2, 3, 4, or 5 on the phenyl ring, and R'=alkyl, aryl, or H; wherein R$_2$=H, alkyl, or aryl; and wherein R$_3$=H, alkyl, or aryl, comprising the steps of:

(a) treating a compound having formula:

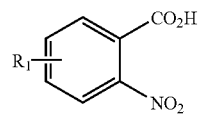

wherein R$_1$ is as defined above, with a reducing agent, in the presence of an optional catalyst, to form a compound having formula:

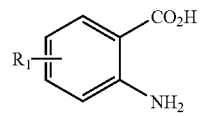

wherein R$_1$ is as defined above;

(b) treating the compound formed in step (a) with a diazotizing agent and a disulfide, to form a compound having formula:

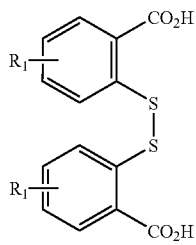

wherein $R_1$ is as defined above;

(c) treating the compound formed in step (b) with an activating agent and chloroethylamine, to form a compound having formula:

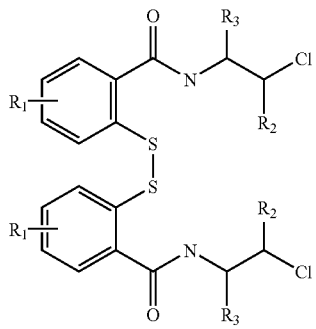

wherein $R_1$, $R_2$, and $R_3$ are as defined above;

(d) treating the compound formed in step (c) with a reducing agent and a base to form a compound having formula:

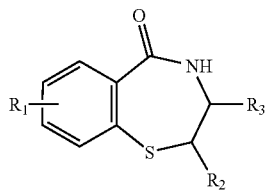

wherein $R_1$, $R_2$, and $R_3$ are as defined above; and (e) treating the compound formed in step (d) with a reducing agent, to form a compound having formula:

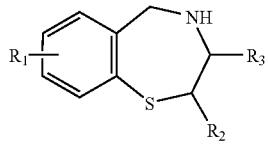

wherein $R_1$, $R_2$, and $R_3$ are as defined above.

The present invention also provides novel assays for regular or high-through-put screening of biologically-active small molecules, based upon rebinding of FKBP12.6 and RyR2. In particular, the present invention provides a method for identifying an agent that enhances binding of RyR2 and FKBP12.6, comprising the steps of: (a) obtaining or generating a source of RyR2; (b) exposing the RyR2 to FKBP12.6, in the presence of a candidate agent; and (c) determining if the agent enhances the binding of RyR2 and FKBP12.6. In one embodiment, the RyR2 is PKA-phosphorylated. In another embodiment, the RyR2 is PKA-hyperphosphorylated. In yet another embodiment, the RyR2 is unphosphorylated.

In the method of the present invention, the RyR2 is immobilized to a solid phase, such as a plate or beads. To facilitate detection of RyR2-FKBP12.6 binding, the FKBP12.6 may be radio-labeled (e.g., with $^{32}S$). Furthermore, enhanced binding of RyR2 and FKBP12.6 may be detected using an FKBP12.6-binding agent. In one embodiment, the FKBP12.6-binding agent is an anti-FKBP12.6 antibody. The present invention also provides an agent identified by this method, as well as uses of this agent in methods for limiting or preventing a decrease in the level of RyR2-bound FKBP12.6 in a subject; in methods for treating or preventing heart failure, atrial fibrillation, or exercise-induced cardiac arrhythmia in a subject; and in methods for preventing exercise-induced sudden cardiac death in a subject.

Additionally, the present invention provides a method for identifying an agent for enhancing the binding of RyR2 and FKBP12.6, comprising the steps of: (a) obtaining or generating a source of FKBP12.6; (b) exposing the FKBP12.6 to RyR2, in the presence of a candidate agent; and (c) determining if the agent enhances the binding of RyR2 and FKBP12.6. In one embodiment, the RyR2 is PKA-phosphorylated. In another embodiment, the RyR2 is PKA-hyperphosphorylated. In yet another embodiment, the RyR2 is unphosphorylated.

In the method of the present invention, the FKBP12.6 is immobilized to a solid phase, such as a plate or beads. To facilitate detection of RyR2-FKBP12.6 binding, the RyR2 may be radio-labeled (e.g., with $^{32}P$). Furthermore, enhanced binding of RyR2 and FKBP12.6 may be detected using an RyR2-binding agent. In one embodiment, the RyR2-binding agent is an anti-RyR2 antibody. The present invention also provides an agent identified by this method, as well as uses of this agent in methods for limiting or preventing a decrease in the level of RyR2-bound FKBP12.6 in a subject; in methods for treating or preventing heart failure, atrial fibrillation, or exercise-induced cardiac arrhythmia in a subject; and in methods for preventing exercise-induced sudden cardiac death in a subject.

By way of example, and as shown in Example 10 below, a highly-efficient assay for high-throughput screening for small molecules may be developed by immobilizing FKBP12.6 (e.g., wild-type FKBP12.6 or a fusion protein, such as GST-FKBP12.6) onto a 96-well plate coated with glutathione, using standard procedures. PKA-phosphorylated ryanodine receptor type 2 (RyR2) may be loaded onto the FKBP12.6-coated plate, and incubated with JTV-519 analogues and other 1,4-benzothiazepene derivatives at various concentrations (10-100 nM) for 30 min. Thereafter, the plate may be washed to remove the unbound RyR2, and then incubated with anti-RyR2 antibody (e.g., for 30 min). The plate may be washed again to remove unbound anti-RyR2 antibody, and then treated with florescent-labeled secondary antibody. The plate may be read by an automatic fluorescent plate reader for binding activity.

Alternatively, RyR2 may be PKA-phosphorylated in the presence of $^{32}P$-ATP. Radioactive PKA-phosphorylated RyR2 may be loaded onto an FKBP12.6-coated, 96-well plate, in the presence of JTV-519 analogues and other 1,4-benzothiazepene derivatives at various concentrations (10-100 nM) for 30 min. The plate may be washed to remove the unbound radiolabeled RyR2, and then read by an automatic plate reader. PKA-phosphorylated RyR2 also may be coated to the plate, and incubated with $^{32}$S-labeled FKBP12.6 in the presence of the analogues and derivatives.

The present invention is described in the following Examples, which are set forth to aid in the understanding of the invention, and should not be construed to limit in any way the scope of the invention as defined in the claims which follow thereafter.

EXAMPLES

Example 1

FKBP12.6-Deficient Mice

FKBP12.6-deficient mice were generated, as previously described (Wehrens et al., FKBP12.6 deficiency and defective calcium release channel (ryanodine receptor) function linked to exercise-induced sudden cardiac death. *Cell,* 113: 829-40, 2003). Briefly, mouse genomic λ-phage clones for the murine orthologue of the human FK506 binding protein 12.6 (FKBP12.6) were isolated from a DBA/1lacJ library, using a full-length murine cDNA probe. The targeting vector was designed to delete exons 3 and 4, which contain the entire coding sequences for murine FKBP12.6 (Bennett et al., Identification and characterization of the murine FK506 binding protein (FKBP) 12.6 gene. *Mamm. Genome,* 9:1069-71, 1998), by replacing 3.5 kb of murine genomic DNA with a PGK-neo selectable marker. A 5.0-kb 5' fragment and a 1.9-kb 3' fragment were cloned into pJNS2, a backbone vector with PGK-neo and PGK-TK cassettes. The DBA/lacJ embryonic stem (ES) cells were grown and transfected, using established protocols. Targeted ES cells were first screened by Southern analysis, and 5 positive ES cell lines were analyzed by PCR to confirm homologous recombination. Male chimeras were bred to DBA/1lacJ females, and germline offspring identified by brown coat color. Germline offspring were genotyped using 5' Southern analysis. Positive FKBP12.6$^{+/-}$ males and females were intercrossed, and offspring resulted in FKBP12.6$^{-/-}$ mice at approximately 25% frequency. FKBP12.6$^{-/-}$ mice were fertile.

All studies performed with FKBP12.6$^{-/-}$ mice used age- and sex-matched FKBP12.6$^{+/+}$ mice as controls. No differences were observed between FKBP12.6$^{-/-}$ mice raised on the following backgrounds: DBA/C57BL6 mixed, pure DBA, and pure C57BL6.

Example 2

Telemetry Recording and Exercise Testing in Mice

FKBP12.6$^{+/+}$ and FKBP12.6$^{-/-}$ mice were maintained and studied according to protocols approved by the Institutional Animal Care and Use Committee of Columbia University. Mice were anaesthetized using 2.5% isoflurane inhalation anesthesia. ECG radiotelemetry recordings of ambulatory animals were obtained >7 days after intraperitoneal implantation (Data Sciences International, St. Paul, Minn.)(Wehrens et al., FKBP12.6 deficiency and defective calcium release channel (ryanodine receptor) function linked to exercise-induced sudden cardiac death. *Cell,* 113:829-40, 2003). For stress tests, mice were exercised on an inclined treadmill until exhaustion, and then intraperitoneally injected with epinephrine (0.5-2.0 mg/kg)(Wehrens et al., FKBP12.6 deficiency and defective calcium release channel (ryanodine receptor) function linked to exercise-induced sudden cardiac death. *Cell,* 113:829-40, 2003). Resting heart rates of ambulatory animals were averaged over 4 h.

Example 3

Expression of Wild-Type and RyR2-S2809D Mutants

Mutagenesis of the PKA target site on RyR2 (RyR2-S2809D) was performed, as previously described (Wehrens et al., FKBP12.6 deficiency and defective calcium release channel (ryanodine receptor) function linked to exercise-induced sudden cardiac death. *Cell,* 113:829-40, 2003). HEK293 cells were co-transfected with 20 µg of RyR2 wild-type (WT) or mutant cDNA, and with 5 µg of FKBP12.6 cDNA, using $Ca^{2+}$ phosphate precipitation. Vesicles containing RyR2 channels were prepared, as previously described (Wehrens et al., FKBP12.6 deficiency and defective calcium release channel (ryanodine receptor) function linked to exercise-induced sudden cardiac death. *Cell,* 113:829-40, 2003).

Example 4

RyR2 PKA Phosphorylation and FKBP12.6 Binding

Cardiac SR membranes were prepared, as previously described (Marx et al., PKA phosphorylation dissociates FKBP12.6 from the calcium release channel (ryanodine receptor): defective regulation in failing hearts. *Cell,* 101: 365-76, 2000; Kaftan et al., Effects of rapamycin on ryanodine receptor/$Ca^{(2+)}$-release channels from cardiac muscle. *Circ. Res.,* 78:990-97, 1996). $^{35}$S-labelled FKBP12.6 was generated using the TNT™ Quick Coupled Transcription/Translation system from Promega (Madison, Wis.). [$^{3}$H] ryanodine binding was used to quantify RyR2 levels. 100 µg of microsomes were diluted in 100 µl of 10-mM imidazole buffer (pH 6.8), incubated with 250-nM (final concentration) [$^{35}$S]-FKBP12.6 at 37° C. for 60 min, then quenched with 500 µl of ice-cold imidazole buffer. Samples were centrifuged at 100,000 g for 10 min, and washed three times in imidazole buffer. The amount of bound [$^{35}$S]-FKBP12.6 was determined by liquid scintillation counting of the pellet.

Example 5

Immunoblots

Immunoblotting of microsomes (50 µg) was performed as described, with anti-FKBP12/12.6 (1:1,000), anti-RyR-5029 (1:3,000)(Jayaraman et al., FK506 binding protein associated with the calcium release channel (ryanodine receptor). *J. Biol. Chem.,* 267:9474-77, 1992), or anti-phosphoRyR2-P2809 (1:5,000) for 1 h at room temperature (Reiken et al., Beta-blockers restore calcium release channel function and improve cardiac muscle performance in human heart failure. *Circulation,* 107:2459-66, 2003). The P2809-phospho-epitope-specific anti-RyR2 antibody is an affinity-purified polyclonal rabbit antibody, custom-made by Zymed Laboratories (San Francisco, Calif.) using the peptide, CRTRRI-(pS)-QTSQ, which corresponds to RyR2 PKA-phosphorylated at $Ser^{2809}$. After incubation with HRP-labeled antirabbit IgG (1:5,000 dilution; Transduction Laboratories, Lexington, Ky.), the blots were developed using ECL (Amersham Pharmacia, Piscataway, N.J.).

Example 6

Single-Channel Recordings

Single-channel recordings of native RyR2 from mouse hearts, or recombinant RyR2, were acquired under voltage-clamp conditions at 0 mV, as previously described (Marx et al., PKA phosphorylation dissociates FKBP12.6 from the calcium release channel (ryanodine receptor): defective regulation in failing hearts. *Cell*, 101:365-76, 2000). Symmetric solutions used for channel recordings were: trans compartment—HEPES, 250 mmol/L; Ba(OH)$_2$, 53 mmol/L (in some experiments, Ba(OH)$_2$ was replaced by Ca(OH)$_2$); pH 7.35; and cis compartment—HEPES, 250 mmol/L; Tris-base, 125 mmol/L; EGTA, 1.0 mmol/L; and CaCl$_2$, 0.5 mmol/L; pH 7.35. Unless otherwise indicated, single-channels recordings were made in the presence of 150-nM [Ca$^{2+}$] and 1.0-mM [Mg$^{2+}$] in the cis compartment. Ryanodine (5 mM) was applied to the cis compartment to confirm identity of all channels. Data were analyzed from digitized current recordings using Fetchan software (Axon Instruments, Union City, Calif.). All data are expressed as mean±SE. The unpaired Student's t-test was used for statistical comparison of mean values between experiments. A value of p<0.05 was considered statistically significant.

Figure 1:
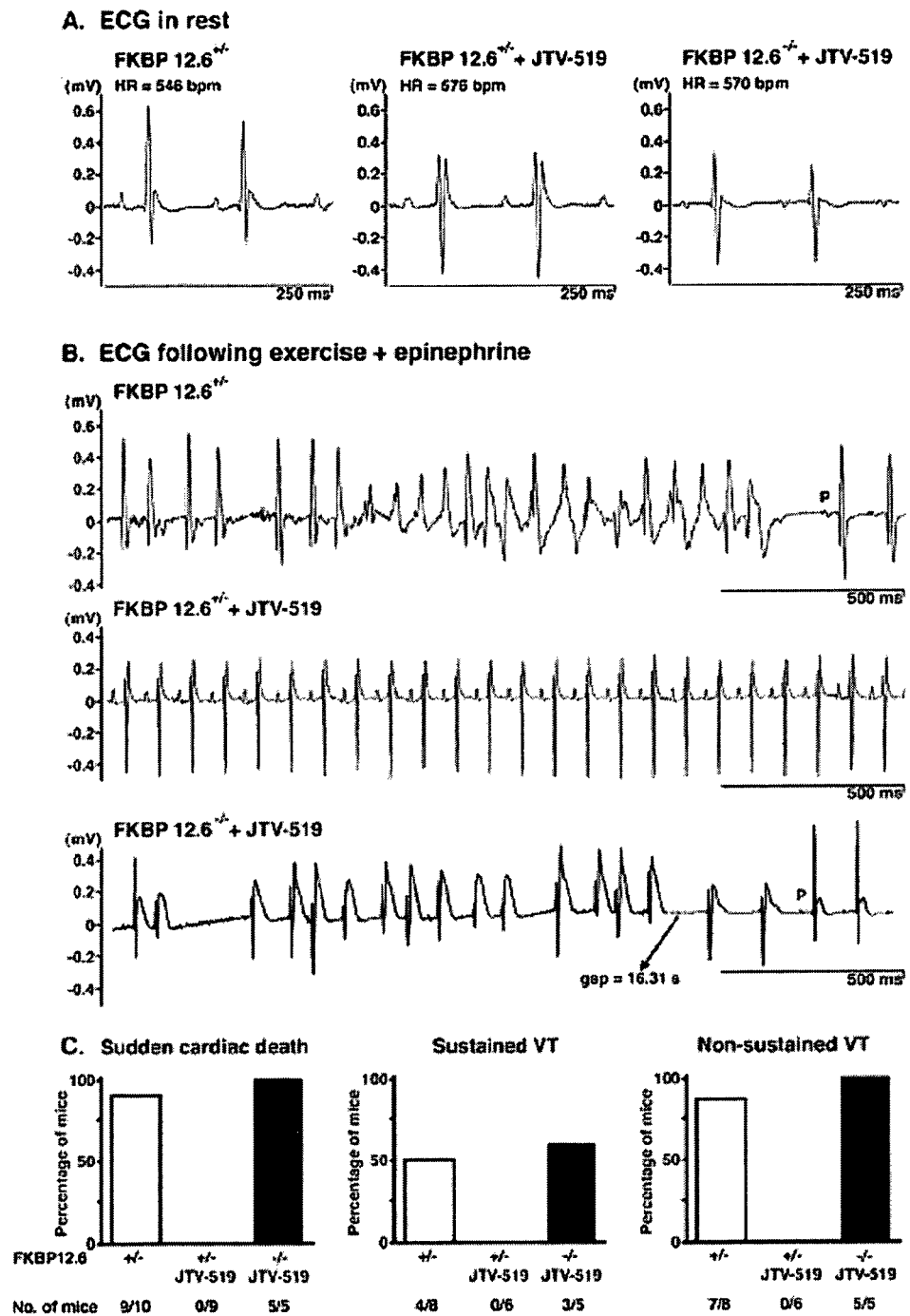
FIG. 1 demonstrates that JTV-519 prevents exercise-induced ventricular arrhythmias in FKBP12.6$^{+/-}$ mice. (A) Representative ambulatory electrocardiograms of an untreated FKBP12.6$^{+/-}$ mouse, an FKBP12.6$^{+/-}$ mouse treated with JTV-519, and an FKBP12.6$^{-/-}$ mouse treated with JTV-519. There were no significant differences in heart rate, or in any of the measured ECG parameters. (B) upper tracing: Example of sustained polymorphic ventricular tachycardia, recorded in an untreated FKBP12.6$^{+/-}$ mouse subjected to exercise testing and injection with 1.0 mg/kg epinephrine middle tracing: Electro-cardiogram of a JTV-519-treated FKBP12.6$^{+/-}$ mouse following the same protocol; no arrhythmias were detected bottom tracing: Exercise-induced ventricular tachycardia (VT) in an FKBP12.6$^{-/-}$ mouse treated with JTV-519. The dotted line represents 16.31 seconds of VT that are not shown in the figure. 'P' indicates a P-wave, which is indicative of sinus rhythm following ventricular tachycardia. (C) Bar graph showing quantification of sudden cardiac death (left), sustained ventricular tachycardias (>10 beats, middle), and non-sustained ventricular tachycardias (3-10 abnormal beats, right) in FKBP12.6$^{+/-}$ and FKBP12.6$^{-/-}$ mice, either treated or not treated with JTV-519, respectively. It should be noted that treatment with JTV-519 completely prevented exercise- and epinephrine-induced arrhythmias in FKBP12.6$^{+/-}$ mice treated with JTV-519 (n=9), as compared with untreated FKBP12.6$^{+/-}$ mice (n=10) or JTV-519-treated FKBP12.6$^{-/-}$ mice (n=5), suggesting that JTV-519 prevents arrhythmias and sudden death in FKBP12.6$^{+/-}$ mice by rebinding FKBP12.6 to RyR2.
Figure 2:
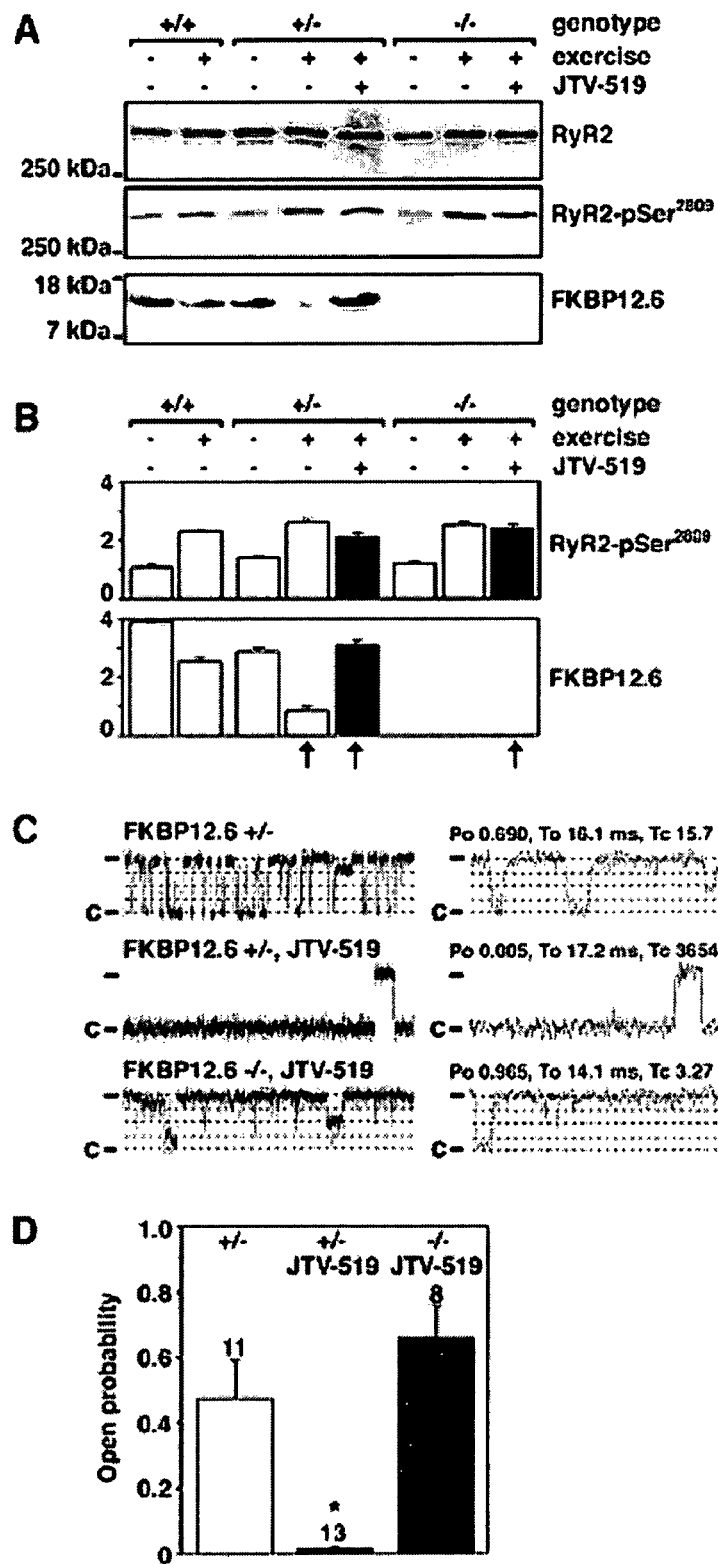
FIG. 2 shows that JTV-519 prevents exercise-induced sudden cardiac death (SCD) by increasing the affinity of FKBP12.6 for RyR2 in FKBP12.6$^{+/-}$ mice. (A-B) Cardiac ryanodine receptors (RyR2) were immunoprecipitated using RyR2-5029 antibody. Shown are immunoblots (A) and bar graphs (B) representing the quantified amounts of RyR2, PKA-phosphorylated RyR2 (RyR2-pSer$^{2809}$ antibody), and FKBP12.6 in wild-type (FKBP12.6$^{+/+}$) mice, FKBP12.6$^{+/-}$ mice, and FKBP12.6$^{-/-}$ under resting conditions, and following exercise, either in the absence or presence of JTV-519, respectively. Under resting conditions, ~70% of FKBP12.6 is associated with RyR2 in FKBP12.6$^{+/-}$ mice. Following exercise testing, the amount of FKBP12.6 associated with the RyR2 complex was dramatically decreased in FKBP12.6$^{+/-}$ mice, but this could be rescued by treatment with JTV-519. (C) RyR2 single channels were isolated from hearts obtained following exercise testing and epinephrine injection. Shown are channels from FKBP12.6$^{+/-}$ mice, with and without pre-treatment with JTV-519, and channels from FKBP12.6$^{-/-}$ mice following JTV-519 pre-treatment. It should be noted that RyR2-channel function was normalized in the exercised FKBP12.6$^{+/-}$ mouse treated with JTV-519. The representative single channel from an exercised FKBP12.6$^{-/-}$ mouse after JTV-519 treatment shows that FKBP12.6 in the heart is required for the action of JTV-519. The dotted lines represent incomplete channel openings, or 'subconductance' openings, and are indicative of FKBP12.6-depleted RyR2 channels. Tracings on the left represent 5.0 sec, while tracings on the right represent 500 msec. In the figure, Po=open probability; To=average open times; Tc=average closed times; and c=closed state of the channel. (D) Summary bar graph showing average open probabilities of single RyR2 channels (see above). JTV-519 dramatically reduces the open probability of RyR2 from FKBP12.6$^{+/-}$ mice following exercise testing at diastolic calcium concentrations (150 nM).
Figure 3:
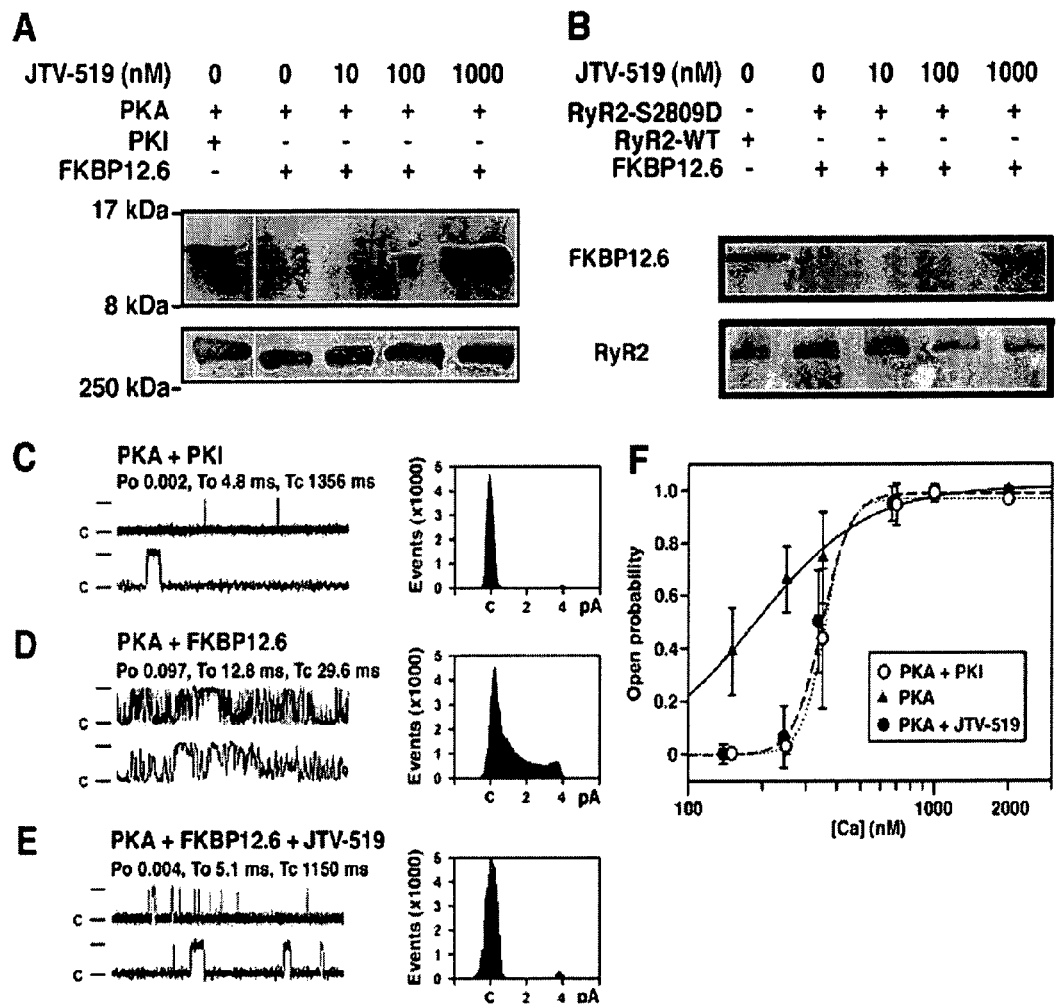
FIG. 3 illustrates JTV-519 normalizes RyR2-channel gating by increased FKBP12.6 binding affinity to PKA-phosphorylated RyR2 channels. (A, B) Canine cardiac SR membranes (A) and recombinantly-expressed RyR2 channels (B) were prepared as described previously (Kaftan et al., Effects of rapamycin on ryanodine receptor/Ca$^{(2+)}$-release channels from cardiac muscle. Circ. Res., 78:990-97, 1996). (A) Ryanodine receptors (RyR2) were phosphorylated with PKA catalytic subunit (40 U; Sigma Chemical Co., St. Louis, Mo.), in the presence or absence of the PKA inhibitor, PKI$_{5-24}$, in phosphorylation buffer (8 mM MgCl$_2$, 10 mM EGTA, and 50 mM Tris/PIPES; pH 6.8). Samples were centrifuged at 100,000×g for 10 min, and washed three times in imidazole buffer (10 mM imidazole; pH 7). Recombinantly-expressed FKBP12.6 (final concentration=250 nM) was added to the samples, in the absence or presence of different concentrations of JTV-519. After a 60-min incubation, samples were centrifuged at 100,000×g for 10 min, and washed twice in imidazole buffer. Samples were heated to 95° C., and size-fractionated using SDS-PAGE. Immunoblotting of the SR microsomes was performed, as previously described (Jayaraman et al., FK506 binding protein associated with the calcium release channel (ryanodine receptor). J. Biol. Chem., 267: 9474-77, 1992), with anti-FKBP12.6 antibody (1:1,000) and anti-RyR2-5029 antibody (1:3,000). The figure demonstrates that JTV-519 enables FKBP12.6 to bind to: (A) PKA-phosphorylated RyR2 (partial binding at 100 nM; complete binding at 1000 nM) or (B) RyR2-S2809D mutant channels, which are constitutively PKA-phosphorylated RyR2 channels. (C-E) Single-channel studies showing increased open probability of RyR2 following PKA phosphorylation (D), as compared with PKA phosphorylation in the presence of the specific PKA inhibitor, PKI$_{5-24}$ (C). Single-channel function was normalized in PKA-phosphorylated RyR2 incubated with FKBP12.6 in the presence of JTV-519 (E). Channel openings are upward, the dash indicates the level of full openings (4 pA), and the letter 'c' indicates the closed state. Channels are shown at compressed (5 sec, upper tracing) and expanded (500 msec, lower tracing) time scales, and recordings are at 0 mV. Amplitude histograms (right) revealed increased activity and subconductance openings in PKA-phosphorylated RyR2, but not following treatment with JTV-519 and FKBP12.6. (F) Normalized plot of open probability as a function of cytosolic [Ca$^{2+}$]. Incubation of PKA-phosphorylated RyR2 with FKBP12.6 in the presence of JTV-519 shifted the Ca$^{2+}$-dependence of RyR2 activation towards the right, making it similar to the Ca$^{2+}$-dependence of unphosphorylated channels.

The effects of JTV-519 on RyR2 channels are set forth in FIGS. 1-3 and Table 1 (below). As demonstrated in FIG. 3, the single-channel studies showed increased open probability of RyR2 following PKA phosphorylation (D), as compared to PKA phosphorylation in the presence of the specific PKA inhibitor, PKI$_{5-24}$ (C). Single-channel function was normalized in PKA-phosphorylated RyR2 incubated with FKBP12.6 in the presence of JTV-519 (E). Amplitude histograms (right) revealed increased activity and subconductance openings in PKA-phosphorylated RyR2, but not following treatment with JTV-519 and FKBP12.6. FIG. 3F shows that incubation of PKA-phosphorylated RyR2 with FKBP12.6, in the presence of JTV-519, shifted the Ca$^{2+}$-dependence of RyR2 activation towards the right, making it similar to the Ca$^{2+}$-dependence of unphosphorylated channels.

TABLE 1

Ambulatory ECG data before, during exercise, and following exercise and injection with epinephrine.

|  | SCL (ms) | HR (bpm) | PR (ms) | QRS (ms) | QT (ms) | QTc (ms) |
|---|---|---|---|---|---|---|
| Baseline |  |  |  |  |  |  |
| FKBP12.6$^{+/-}$ | 104 ± 6 | 586 ± 36 | 32 ± 1.5 | 9.9 ± 0.4 | 30 ± 1.0 | 29 ± 0.6 |
| FKBP12.6$^{+/-}$ + JTV-519 | 99 ± 5 | 608 ± 32 | 33 ± 0.6 | 9.3 ± 0.3 | 32 ± 2.7 | 32 ± 1.9 |
| FKBP12.6$^{-/-}$ + JTV-519 | 116 ± 9 | 527 ± 43 | 33 ± 0.4 | 10.0 ± 0.3 | 33 ± 1.3 | 30 ± 1.1 |
| Maximum exercise |  |  |  |  |  |  |
| FKBP12.6$^{+/-}$ | 80 ± 2 | 752 ± 18 | 28 ± 0.7 | 8.7 ± 0.4 | 30 ± 1.7 | 33 ± 1.6 |
| FKBP12.6$^{+/-}$ + JTV-519 | 90 ± 7 | 676 ± 49 | 29 ± 1.8 | 9.6 ± 0.4 | 34 ± 2.0 | 36 ± 0.9 |
| FKBP12.6$^{-/-}$ + JTV-519 | 83 ± 3 | 729 ± 22 | 29 ± 2 | 9.3 ± 0.3 | 30 ± 1.2 | 33 ± 0.9 |
| Post-exercise epinephrine |  |  |  |  |  |  |
| FKBP12.6$^{+/-}$ | 94 ± 4 | 645 ± 28 | 35 ± 2.6 | 9.3 ± 0.4 | 33 ± 1.8 | 34 ± 1.9 |
| FKBP12.6$^{+/-}$ + JTV-519 | 102 ± 4 | 592 ± 21 | 37 ± 2.6 | 9.9 ± 0.6 | 32 ± 2.3 | 32 ± 1.7 |
| FKBP12.6$^{-/-}$ + JTV-519 | 103 ± 4 | 585 ± 20 | 35 ± 3.8 | 11.1 ± 0.5 | 36 ± 1.2 | 36 ± 1.3 |

Summary of ambulatory ECG data in FKBP12.6$^{+/-}$ mice treated with JTV-519 (n = 8) or control (n = 6), and FKBP12.6$^{-/-}$ mice treated with JTV-519 (n = 5).
SCL = sinus cycle length;
HR = heart rate;
ms = millisecond;
bpm = beats per minute;
FKBP12.6$^{+/-}$ = FKBP12.6 heterozygous mice;
FKBP12.6$^{-/-}$ = FKBP12.6 deficient mice Example 7

Synthesis of 1,4-Benzothiazepine Intermediate and JTV-519

For the in vivo experiments, the inventors required a gram quantity of JTV-519. However, initial attempts to prepare this compound via the reported 1,4-benzothiazepine intermediate, 7-methoxy-2,3,4,5-tetrahydro-1,4-benzothiazepine (compound 6 in Scheme 1, below), were unsuccessful. The thio group of this intermediate is easily oxidized by air to a disulfide compound, which makes the synthesis of cyclized product (5) impossible. To overcome this problem, the inventors developed a novel process that starts with the readily-available and inexpensive 2-nitro-5-methoxybenzoic acid (1). This process is depicted in Scheme 1 below.

Reduction of the nitro group of compound (1), using H$_2$ with Pd/C as a catalyst, gave 2-amino-5-methoxybenzoic acid (2) in quantitative yield. Compound (2) was diazotized with NaNO$_2$, and then treated with Na$_2$S$_2$ to provide the stable disulfide compound (3) with 80% yield. Without further purification, the stable disulfide (3) was treated with SOCl$_2$, and then reacted with 2-chloroethylamine, in the presence of Et$_3$N, to give an amide (4) in 90% yield. Compound (4) was converted to cyclized compound (5) via a one-pot procedure by reflux with trimethylphosphine and Et$_3$N in THF. The cyclized amide (5) was then reduced with LiAlH$_4$ to yield 7-methoxy-2,3,4,5-tetrahydro-1,4-benzothiazepine (6).

JTV-519 was prepared by reacting compound (6) with 3-bromopropionic chloride, and then reacting the resulting product with 4-benzyl piperidine. The structure of JTV-519 was established by ¹H NMR.

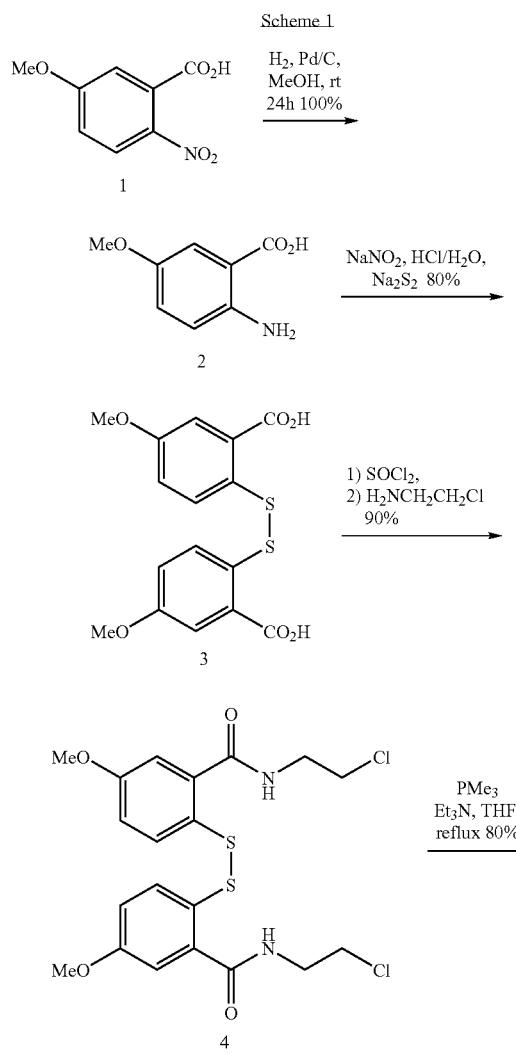

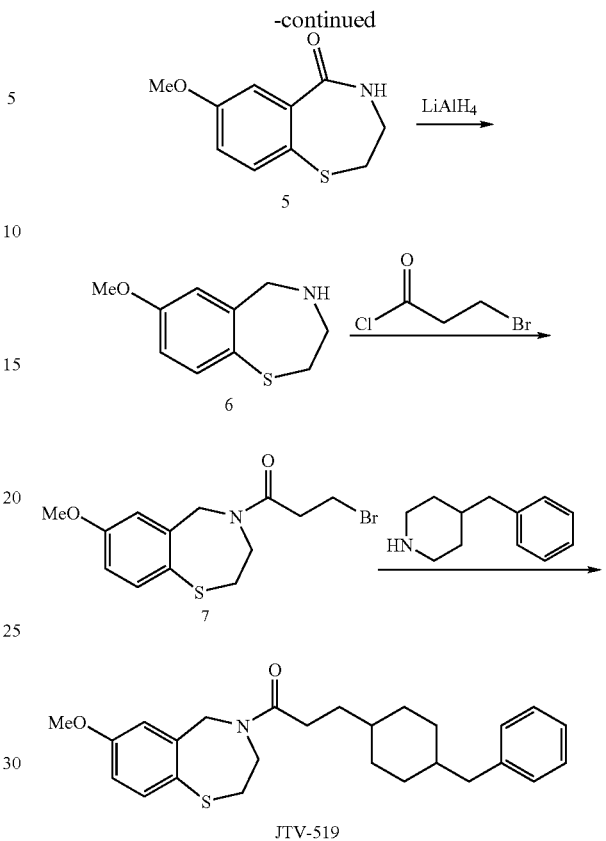

Example 8

Synthesis of Radio-Labeled JTV-519

The inventors' novel process for synthesizing radio-labeled JTV-519 is depicted in Scheme 2 below. To prepare radio-labeled JTV-519, JTV-519 was demethylated at the phenyl ring using BBr₃, to give phenol compound (21). The phenol compound (21) was re-methylated with a radio-labeled methylating agent (³H-dimethyl sulfate) in the presence of a base (NaH) to provide ³H-labeled JTV-519 (Scheme 2).

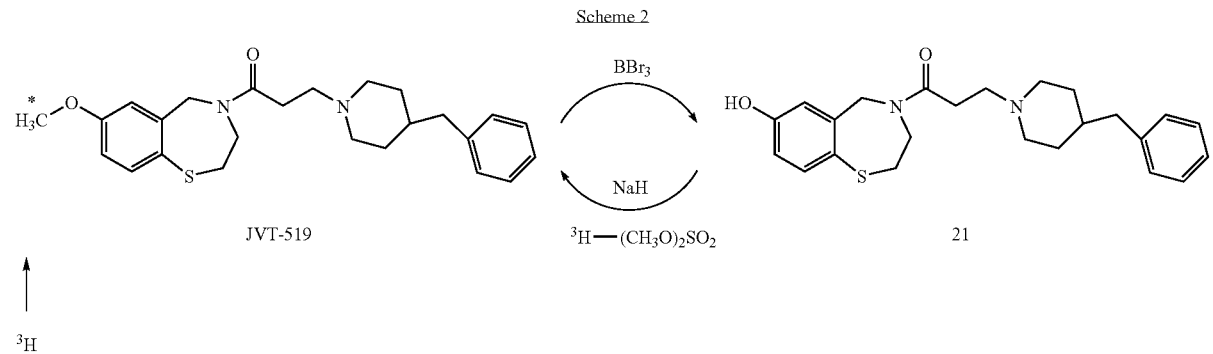

Example 9

Novel 1,4-Benzothiazepine Derivatives and Methods for Their Synthesis

The inventors also developed novel 1,4-benzothiazepine derivatives for use in treating and preventing cardiac arrhythmias. In particular, the inventors produced compounds having the following general structure:

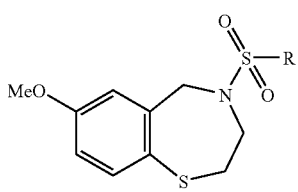

wherein R=aryl, alkenyl, alkyl, —(CH$_2$)$_n$NR'$_2$, or —(CH$_2$)$_n$SR', and n=0, 1, 2, or 3; and wherein R'=alkyl or cycloalkyl. Novel compounds of this general structure were prepared by reacting 7-methoxy-2,3,4,5-tetrahydro-1,4-benzothiazepine with alkylsulfonyl chloride or arylsulfonyl chloride, in the presence of a base such as Et$_3$N. Additional reactions (e.g., addition of 4-benzyl piperidine) may follow, to extend the side chain as desired. A representative synthesis of this general process is depicted in Scheme 3 below.

As Scheme 3 demonstrates, 2-chloroethanesulfonyl chloride (180 mg; 1.1 mM) and Et$_3$N (140 mg; 1.1 mM) were added to 7-methoxy-2,3,4,5-tetrahydro-1,4-benzothiazepine (1)(194 mg; 1 mM) in CH$_2$Cl$_2$ (20 ml), at 0° C. The mixture was stirred at 0° C. for 2 h, and washed with H$_2$O and saturated NaHCO$_3$ solution. Removal of the solvent gave crude product (Ia), which was purified by chromatography on silica gel (petroleum ether:ethyl acetate=3:1). The yield from this synthesis was 280 mg, or 95%. The structure was confirmed by NMR.

Scheme 3 further shows that the side chain of compound (Ia) was extended by reacting compound (Ia)(28 mg; 0.1 mM) with 4-benzyl piperidine (21 mg; 0.13 mM) in CH$_2$Cl$_2$. After the reaction went to completion (by TLC), the excess amine was removed by a base scavenger (3-(2-succinic anhydride)propylfunctionalized silica gel, 0.5 g). $^1$HNMR and HPLC showed that the purity of product (Ib) was >98%.

Scheme 3

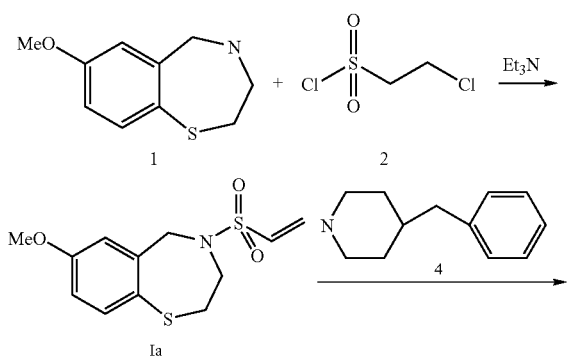

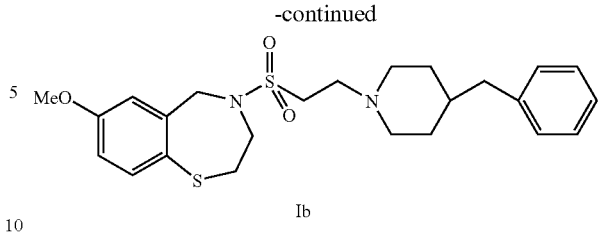

Additionally, the inventors produced compounds having the following general structure:

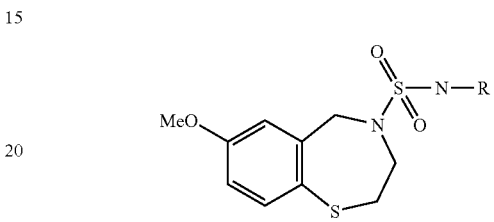

wherein R=aryl, alkyl, —(CH$_2$)$_n$NR'$_2$, or —(CH$_2$)$_n$SR', and n=0, 1, 2, or 3; and wherein R'=alkyl or cycloalkyl. Novel compounds of this general structure were prepared by a one-pot reaction of 7-methoxy-2,3,4,5-tetrahydro-1,4-benzothiazepine (1) with sulfuryl chloride, in the presence of a base (Et$_3$N), followed by a primary or secondary amine. A representative synthesis of this general process is depicted in Scheme 4 below.

As Scheme 4 demonstrates, sulfuryl chloride (15.0 mg; 0.111 mM) and Et$_3$N (28.0 mg; 0.22 mM) were added to 7-methoxy-2,3,4,5-tetrahydro-1,4-benzothiazepine (1) (19.4 mg; 0.1 mM) in CH$_2$Cl$_2$ (20 ml), at 0° C. After stirring the mixture for 2 h at 0° C., 1-piperonylpiperazine (27 mg; 0.12 mM) was added. The mixture was stirred for another 2 h, and then washed with H$_2$O and a saturated NaHCO$_3$ solution. The excess amine was removed by addition of a base scavenger (3-(2-succinic anhydride)propylfunctionalized silica gel, 0.2 g). The yield from this synthesis was 36 mg, or 77%.

Scheme 4

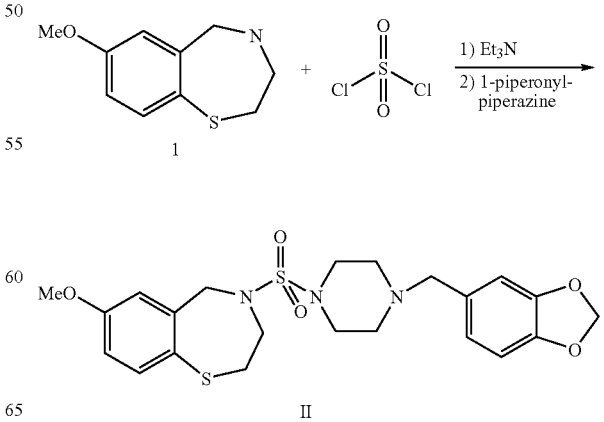

The inventors also produced compounds having the following general structure:

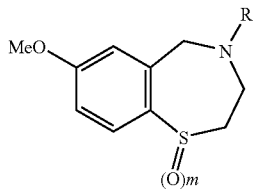

wherein R=CO(CH$_2$)$_n$XR'$_2$, SO$_2$(CH$_2$)$_n$XR'$_2$, or SO$_2$NH(CH$_2$)$_n$XR'$_2$, and X=N or S, and n=1, 2, or 3, and R'=alkyl or cycloalkyl; and wherein m=1 or 2. Novel compounds of this general structure were prepared by oxidation of JTV-519, or one of the novel 1,4-benzothiazepine derivatives described above, with hydrogen peroxide. A representative synthesis of this general process is depicted in Scheme 5 below.

As Scheme 5 shows, compound (Ib)(21 mg; 0.05 mM) in MeOH (5 ml) was added to H$_2$O$_2$ (0.1 ml, excess). The mixture was stirred for 2 days, and the product III was purified by chromatography on silica gel (CH$_2$Cl$_2$:MeOH=10:1). The yield from this synthesis was 19 mg, or 91%.

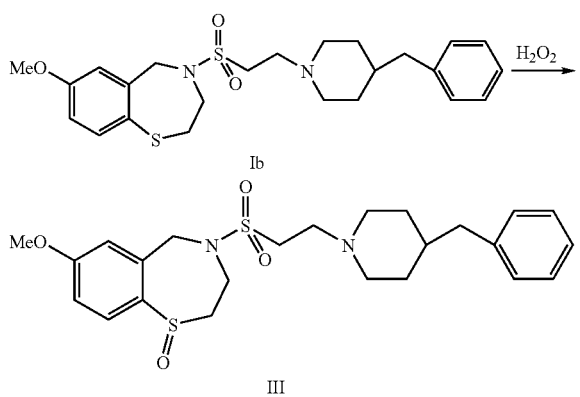

Scheme 5

Finally, the inventors produced compounds having the following general structure:

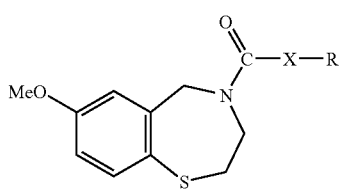

wherein R=aryl, alkyl, —(CH$_2$)$_n$NR'$_2$, —(CH$_2$)$_n$SR', and n=0, 1, 2, or 3, and R'=alkyl or cycloalkyl; and wherein X=NH or O. Novel compounds of this general structure were prepared by reacting 7-methoxy-2,3,4,5-tetrahydro-1,4-benzothiazepine (1) with triphosgene, in the presence of a base (Et$_3$N), followed by addition of a primary or secondary amine or an alcohol. A representative synthesis of this general process is depicted in Scheme 6 below.

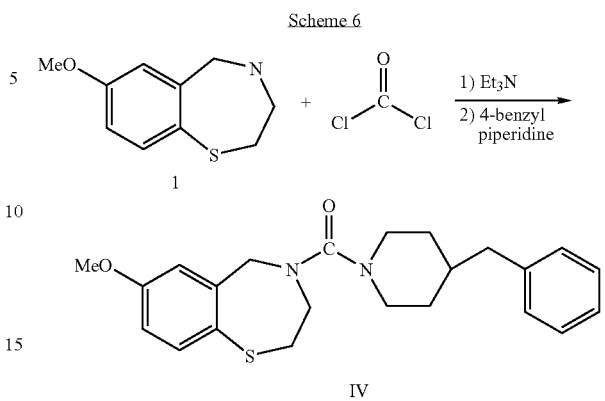

Scheme 6

Example 10

Assay for High-Throughput Screening

The inventors have developed assays for screening biologically-active small molecules. These assays are based on rebinding of FKBP12 protein to RyR2.

A highly-efficient assay for high-throughput screening for small molecules may be developed by immobilization of FKBP12.6 (GST-fusion protein) onto a 96-well plate coated with glutathione. PKA-phosphorylated ryanodine receptor type 2 (RyR2) is loaded onto the FKBP12.6-coated plate, and incubated with JTV-519 analogues at various concentrations (10-100 nM) for 30 min. Thereafter, the plate is washed to remove the unbound RyR2, and then incubated with anti-RyR2 antibody for 30 min. The plate is again washed to remove unbound anti-RyR2 antibody, and then treated with florescent-labeled secondary antibody. The plate is read by an automatic fluorescent plate reader for binding activity.

In an alternative assay, RyR2 is PKA-phosphorylated in the presence of $^{32}$P-ATP. Radioactive PKA-phosphorylated RyR2 is loaded onto an FKBP12.6-coated, 96-well plate, in the presence of JTV-519 analogues at various concentrations (10-100 nM) for 30 min. The plate is washed to remove the unbound radiolabeled RyR2, and then read by an automatic plate reader.

While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. The compound S36:

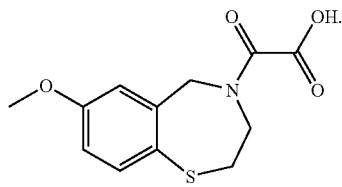

2. A composition comprising S36 and a pharmaceutically acceptable carrier.

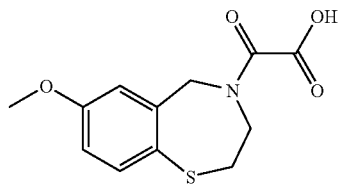

3. The composition of claim 2 wherein the carrier comprises carboxymethyl cellulose, crystalline cellulose, glycerin, gum arabic, lactose, magnesium stearate, methyl cellulose, saline, sodium alginate, sucrose, starch, talc or water.

4. The composition of claim 2 which further includes one or more of an antioxidant, colorant, flavor improving agent, preservative, sweetener, binder or lubricant.

5. The composition of claim 2 in the form of a capsule, tablet, powder, granule, or suspension.

* * * * *

UNITED STATES PATENT AND TRADEMARK OFFICE
CERTIFICATE OF CORRECTION

PATENT NO. : 7,544,678 B2  Page 1 of 1
APPLICATION NO. : 11/088058
DATED : June 9, 2009
INVENTOR(S) : Marks et al.

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by 499 days Delete the phrase "by 499 days" and insert -- by 942 days --

Signed and Sealed this

Thirteenth Day of April, 2010

David J. Kappos
*Director of the United States Patent and Trademark Office*